(12) United States Patent
Player et al.

(10) Patent No.: US 7,790,724 B2
(45) Date of Patent: Sep. 7, 2010

(54) C-FMS KINASE INHIBITORS

(75) Inventors: Mark R. Player, Phoenixville, PA (US);
Nand Baindur, Kendall Park, NJ (US);
Benjamin Brandt, Philadelphia, PA (US); Naresh Chadha, Montville, NJ (US); Raymond J. Patch, Yardley, PA (US); Davoud Asgari, Tehran (IR);
Taxiarchis M. Georgiadis, Carmel, IN (US)

(73) Assignee: Janssen Pharmaceutica N.V., Beerse (BE)

( * ) Notice: Subject to any disclaimer, the term of this patent is extended or adjusted under 35 U.S.C. 154(b) by 1149 days.

(21) Appl. No.: 11/407,605

(22) Filed: Apr. 20, 2006
(Under 37 CFR 1.47)

(65) Prior Publication Data

US 2006/0258666 A1 Nov. 16, 2006

Related U.S. Application Data

(63) Continuation-in-part of application No. 10/831,216, filed on Apr. 26, 2004, now Pat. No. 7,429,603.

(60) Provisional application No. 60/465,204, filed on Apr. 25, 2003.

(51) Int. Cl.
A61K 31/4439 (2006.01)
C07D 403/02 (2006.01)

(52) U.S. Cl. .................. 514/252.05; 514/326; 514/341; 514/400; 544/238; 546/210; 546/272.7; 548/335.5

(58) Field of Classification Search ........................ None
See application file for complete search history.

(56) References Cited

U.S. PATENT DOCUMENTS

| | | | |
|---|---|---|---|
| 3,717,579 A | 2/1973 | Hoffman et al. | |
| 3,862,152 A | 1/1975 | Kuwada et al. | |
| 4,172,947 A | 10/1979 | Warner, Jr. et al. | |
| 4,186,199 A | 1/1980 | Gllamkowski et al. | |
| 5,258,357 A | 11/1993 | Muenster et al. | |
| 5,854,285 A | 12/1998 | Sriram et al. | |
| 6,348,480 B1 * | 2/2002 | Kubota et al. | 514/361 |
| 6,380,247 B2 | 4/2002 | Konishi et al. | |
| 6,420,567 B1 | 7/2002 | Wu et al. | |
| 6,545,161 B2 | 4/2003 | Gupta et al. | |
| 6,936,736 B2 | 8/2005 | Ikeda et al. | |
| 7,012,094 B1 | 3/2006 | Bertenshaw et al. | |
| 7,019,024 B2 | 3/2006 | Ognyanov et al. | |
| 7,037,937 B2 | 5/2006 | Uckun et al. | |
| 7,041,702 B1 | 5/2006 | Durant et al. | |
| 7,045,551 B2 | 5/2006 | Wu et al. | |
| 7,087,604 B2 | 8/2006 | Cherney | |
| 7,098,240 B2 | 8/2006 | Griffiths et al. | |
| 7,105,564 B1 | 9/2006 | Honma et al. | |
| 7,109,243 B2 | 9/2006 | Liu et al. | |
| 7,115,660 B2 | 10/2006 | Boger et al. | |
| 7,179,840 B2 | 2/2007 | Rieck et al. | |
| 2005/0004112 A1 | 1/2005 | Player et al. | |
| 2005/0113566 A1 | 5/2005 | Player et al. | |
| 2005/0131022 A1 | 6/2005 | Player et al. | |

FOREIGN PATENT DOCUMENTS

| | | |
|---|---|---|
| DE | 26 35 818 A1 | 11/1977 |
| EP | 1 193 246 A1 | 4/2002 |
| GB | 1 508 947 | 4/1978 |
| WO | WO 95/19169 A2 | 7/1995 |
| WO | WO 00/27820 A | 5/2000 |
| WO | WO 00/62778 A1 | 10/2000 |
| WO | WO 02/28825 A | 4/2002 |
| WO | WO 02/068406 A | 9/2002 |
| WO | WO 03/103648 A1 | 12/2003 |
| WO | WO 03/103658 A1 | 12/2003 |
| WO | WO 2004/22525 A | 3/2004 |
| WO | WO 2004/184461 A | 3/2004 |
| WO | WO 2004/96795 A | 11/2004 |
| WO | WO 2006/047277 A2 | 5/2006 |
| WO | WO 2006/047504 A1 | 5/2006 |

OTHER PUBLICATIONS

West, Anthony R., Solid State Chemistry and its Applications, Wiley, New York, 1988, pp. 358 & 365.*

Blankley et al, "Antihypertensive Activity of 6-Arylpyrido[2,3-d]pyrimidin-7-amine Derivatives. 2. 7-Acyl Amide Analogues", *Journal of Medicinal Chemistry*, vol. 26, No. 3, Mar. 1, 1983, pp. 403-411, ISSN: 0022-2623 (XP002000852).

Chan et al, "Halogen Substitution at the Isoxazole Ring Enhances the Activity of N-(Isoxazolyl)sulfonamide Endothelin Antagonists", *Bioorganic & Medicinal Chemistry Letters*, vol. 6, No. 20, 1996, pp. 2393-2398, ISSN: 0960-894X (XP002314441).

Contreras et al, "Aminopyridazines as Acetylcholinesterase Inhibitors", *Journal of Medicinal Chemistry*, vol. 42, No. 4, Feb. 25, 1999, pp. 730-741, ISSN: 0022-2623 (XP002353008).

(Continued)

*Primary Examiner*—Zinna N Davis

(57) ABSTRACT

The invention is directed to compounds of Formula II:

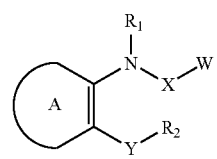

wherein A, $R_1$, $R_2$, $R_3$, $R_4$, X, Y and W are set forth in the specification, as well as solvates, hydrates, tautomers or pharmaceutically acceptable salts thereof, that inhibit protein tyrosine kinases, especially c-fms kinase.

9 Claims, No Drawings

OTHER PUBLICATIONS

Moffett et al, "Antiulcer Agents. p-Aminobenzamido Aromatic Compounds", *Journal of Medicinal Chemistry*, vol. 14, No. 10, Oct. 1971, pp. 963-968, ISSN: 0022-2623 (XP002057311).

Robert-Piessard et al, "Non-acidic Anti-inflammatory Compounds: Activity of N-(4,6-dimethyl-2-pyridinyl) Benzamides and Derivatives", *European Journal of Medicinal Chemistry*, vol. 25, No. 1, 1990, pp. 9-19, ISSN: 0223-5234 (XP001062115).

Seydel et al, "Quantitative Structure-Pharmacokinetic Relationships Derived on Antibacterial Sulfonamides in Rats and Its Comparison to Quantitative Structure-Activity Relationships", *Journal of Medicinal Chemistry*, vol. 23, No. 6, Jun. 1980, pp. 607-613, ISSN: 0022-2623 (XP002392659).

Stein et al, "Discovery and Structure-Activity Relationships of Sulfonamide $Et_A$- Selective Antagonists", *Journal of Medicinal Chemistry*, vol. 38, No. 8, 1995, pp. 1344-1354, ISSN: 0022-2623 (XP002314442).

Database Beilstein, Beilstein Crossfire Institut Zur Foerderung Der Chemischen Wissenschaften, DE; BRN 316474 1954 (XP0023922714).

Database Beilstein, Beilstein Crossfire Institut Zur Foerderung Der Chemischen Wissenschaften, DE; BRN 393777 1966 (XP002392715).

Database Beilstein, Beilstein Crossfire Institut Zur Foerderung Der Chemischen Wissenschaften, DE; BRN 5344832 1922 (XP002392716).

Database Beilstein, Beilstein Crossfire Institut Zur Foerderung Der Chemischen Wissenschaften, DE; BRN 7604813 1996 (XP002392717).

Database Beilstein, Beilstein Crossfire Institut Zur Foerderung Der Chemischen Wissenschaften, DE; BRN 8848189 2001 (XP002392718).

Database Beilstein, Beilstein Crossfire Institut Zur Foerderung Der Chemischen Wissenschaften, DE; BRN 7600437 1996 (XP002392719).

Database Beilstein, Beilstein Crossfire Institut Zur Foerderung Der Chemischen Wissenschaften, DE; BRN 5448817 1991 (XP002392720).

Database Beilstein, Beilstein Crossfire Institut Zur Foerderung Der Chemischen Wissenschaften, DE; BRN 6975717 1985 (XP002392721).

Database Beilstein, Beilstein Crossfire Institut Zur Foerderung Der Chemischen Wissenschaften, DE; BRN 7036362 1994 (XP002392722).

Database Beilstein, Beilstein Crossfire Institut Zur Foerderung Der Chemischen Wissenschaften, DE; BRN 410569 1971 (XP002392723).

Database Beilstein, Beilstein Crossfire Institut Zur Foerderung Der Chemischen Wissenschaften, DE; BRN 438575 1973 (XP002392724).

Database Beilstein, Beilstein Crossfire Institut Zur Foerderung Der Chemischen Wissenschaften, DE; BRN622512 1974 (XP002392725).

Database Beilstein, Beilstein Crossfire Institut Zur Foerderung Der Chemischen Wissenschaften, DE; BRN4209696 1990 (XP002392726).

Database Beilstein, Beilstein Crossfire Institut Zur Foerderung Der Chemischen Wissenschaften, DE; BRN 309332 1946 (XP002392727).

Database Beilstein, Beilstein Crossfire Institut Zur Foerderung Der Chemischen Wissenschaften, DE; BRN 253307 1959 (XP002392728).

Database Beilstein, Beilstein Crossfire Institut Zur Foerderung Der Chemischen Wissenschaften, DE; BRN308560 1948 (XP002392729).

Beier et al, CA122:132943 (1995).

Freund et al, CA63:1170b (1982).

Snyder, Journal of Medicinal Chemistry (1967) 10(4):737-739.

Nilsson et al, J. Comb. Chem (2001) 3:546-553.

Database Chemcats, Chemical Abstracts Service, Columbus, Ohio, US; XP002307086, Order Nos. t0370-0639, t0369-0732. &

"Ambinter Stock Screening Collection", Jan. 1, 2004, Ambinter, 46 Quai Loius Bleriot, F-75016 Paris, France.

WO 03/103648A (Muto et al; Inst of Medicinal Molecular) Dec. 18, 2003, Abstract; & Database Chemabs 'Online! Chemical Abstracts Service, Columbus, Ohio, US; XP002307087, retrieved from STN Database accession No. 140:27850 Abstract; and RN's 439144-91-9, 634185-05-0, 634185-10-7, 634185-14-1.

WO 03/103658A (Muto et al; Inst of Medicinal Molecular) Dec. 18, 2003, Abstract; & Database Chemabs 'Online! Chemical Abstracts Service, Columbus, Ohio, US; XP002307891, retrieved from STN Database accession No. 140:42204 Abstract; and RN's 439144-91-9, 634185-05-0, 634185-10-7, 634185-14-1.

Database Chemcats, Chemical Abstracts Service, Columbus, Ohio, US; XP002307088, Order No. CHS2296111. & "ChemStar Product List" Apr. 24, 2003, Chemstar Ltd, Leningradskii Prospekt 47, Office 465, Moskow, 125167, Russia.

Database Beilstein, Beilstein Institute for Organic Chemistry, Frankfurt-Main, DE; XP002307089, Database Accession No. 290139 (BRN). & Chem. Ber., vol. 24, 1891, p. 2101.

Database Beilstein, Beilstein Institute for Organic Chemistry, Frankfurt-Main, DE; XP002307090, Database Accession Nos. 1012247, 1257241, 1319746, 1322924 (BRN's). & J. Chem. Soc., 1963, pp. 4666-4669.

Database Beilstein, Beilstein Institute for Organic Chemistry, Frankfurt-Main, DE; XP002307091, Database Accession Nos. 551856, 578613, 1257241, 1322924, 1324197 (BRN's). & J. Chem. Soc., 1964, p. 2609.

Database Beilstein, Beilstein Institute for Organic Chemistry, Frankfurt-Main, DE; XP002307092, Database Accession Nos. 1601543, 2983204, 2982987 (BRN's). & J. Chem. Soc. C, 1969, pp. 1444-1448.

Database Beilstein, Beilstein Institute for Organic Chemistry, Frankfurt-Main, DE; XP002307093, Database Accession Nos. 702242, 705174, 715898 (BRN's). & Justus Liebigs Ann. Chem., vol. 699, 1966, p. 88.

Database Beilstein, Beilstein Institute for Organic Chemistry, Frankfurt-Main, DE; XP002307094, Database Accession Nos. 126414, 1662045 (BRN's). & J. Chem. Soc. B, 1971, p. 696.

Database Beilstein, Beilstein Institute for Organic Chemistry, Frankfurt-Main, DE; XP002307095, Database Accession Nos. 5608933, 5609095 (BRN's). & Chem. Pharm. Bull., vol. 31, No. 9, 1983, pp. 3160-3167.

Database Beilstein, Beilstein Institute for Organic Chemistry, Frankfurt-Main, DE; XP002307096, Database Accession No. 5966001 (BRN). & Chem. Pharm. Bull., vol. 36, No. 9, 1988, pp. 3248-3252.

Melik-Organdzhanyan et al.: "New Method for the Synthesis of Polyfunctional 5-Aminopyrimidines", Chem. Heterocycl. Compd. Engl. Transl., 1983, pp. 100-102, XP009040286.

Yoshino et al: "Novel Sulfonamides as Potential, Systematically Active Antitumor Agents", J. Med. Chem., vol. 35, 1992, pp. 2496-2497, XP002307084.

Hodson et al.: "Alphal-Adrenoceptor Activation: A Comparison of 4-(Anilinomethyl)imidazoles and 4-(Phenoxymethyl)imidazoles to Related 2-Imidazolines", Bioorg. Med. Chem. Lett., vol. 12, 2002, pp. 3449-3452, XP002307084.

Database Beilstein, Beilstein Institute for Organic Chemistry, Frankfurt-Main, DE; XP002307097, Database Accession Nos. 282633, 402265, 403511 (BRN's). & Helv. Chim. Acta, vol. 61, 1978, p. 2887.

Database Beilstein, Beilstein Institute for Organic Chemistry, Frankfurt-Main, DE; XP002307098, Database Accession Nos. 6972518, 6973696, 6974212, 6975313, 6975875 (BRN's). & Farmaco Ed. Sci., vol. 42, No. 3, 1987, pp. 231-236.

Database Beilstein, Beilstein Institute for Organic Chemistry, Frankfurt-Main, DE; XP002307099, Database Accession Nos. 1112966, 1378557, 1384830, 2732875, 2743259, 2743836, 2746021, 2752729, 2755871, 2774906 (BRN's). & Bull. Soc. Chim. Fr., 1973, pp. 3017-2018.

Database Beilstein, Beilstein Institute for Organic Chemistry, Frankfurt-Main, DE; XP002307100, Database Accession Nos. 4875002, 4878430, 4878634, 4880771, 4881664, 4884524, (BRN's). & J. Med. Chem., vol. 35, No. 5, 1992, pp. 804-807.

Database Beilstein, Beilstein Institute for Organic Chemistry, Frankfurt-Main, DE; XP002307101, Database Accession No. 177103 (BRN). & Arh. Chem., vol. 27, 1955, p. 33.

Database Beilstein, Beilstein Institute for Organic Chemistry, Frankfurt-Main, DE; XP002307102, Database Accession Nos. 28308, 252444 (BRN's). & Proc.-Indian Acad. Sci. Sect. A, vol. 38, 1953, p. 58.

Database Beilstein, Beilstein Institute for Organic Chemistry, Frankfurt-Main, DE; XP002307103, Database Accession Nos. 22169, 3751528 (BRN's). & J. Am. Chem. Soc., vol. 40, 1980, p. 566.

Database Beilstein, Beilstein Institute for Organic Chemistry, Frankfurt-Main, DE; XP002307104, Database Accession Nos. 197306, 3795001 (BRN's). & Gazz. Chim. Ital., vol. 80, 1950, p. 456.

Database Chemcats 'Online!, Chemical Abstracts Service, Columbus, Ohio, US; XP002307105, retrieved from STN, Order No. 2022-2088. & "Interchim Intermediates" Jul. 9, 2002, Interchim, 213 Avenue Kennedy, BP 1140, Montlucon, Cedex, 03103, France.

Klunder et al.: "Novel Non-Nucleoside Inhibitors of HIV-1 Reverse Transcriptase. 2. Tricyclic Pyridobenzoxazepinones and Dibenzoxazephinones.", J. Med. Chem., vol. 35, 1992, pp. 1887-1897, XP002307085.

Traxler: "Tyrosine Kinase Inhibitors in Cancer Treatment (Part II)" Expert Opinion on Therapeutic Patents, Ashley Publications, GB, vol. 8, No. 12, 1998, pp. 1599-1625, XP001183544, ISSN: 1354-3776.

Showalter et al: "Tyrosine Kinase Inhibitors. 16. 6,5,6-Tricyclic Benzothieno [3,2-*d*]pyrimidines and Pyrimido[5,4-*b*]- and -[4,5-*b*]indoles as Potent Inhibitors of the Epidermal Growth Factor Receptor Tyrosine Kinase" Journal of Medicinal Chemistry, American Chemical Society. Washington, US, vol. 42, 1999, pp. 5464-5474, XP002210181, ISSN: 0022-2633.

Dhanoa et al, "Serine Proteases-Directed Small Molecule Probe Libraries", Medicinal Chemistry Research, vol. 8, No. 4/5 (1998) pp. 187-205 (XP009016618) ISSN: 1054-2523.

Database Beilstein, Beilstein Crossfire Institut Zur Foerderung Der Chemischen Wissenschaften, DE; BRN 214943, BRN 214944, BRN 303350 (XP002378023).

CAS Accerssion No. 1973:132353, Registry No. 41235-81-8.

Database CA. Chemical Abstracts Service. Vostrova, L.N. 'Nitrogen Heterocycles Based on Derivatives of Diimidazo [1,5-a;1',5'-d]pyrazine-5,10-diones' Database Accession No. 1983:126026. XP002401298. Abstract. Ukrainskii Khimicheskii Zhurnal (Russian Edition)(1982) 48(10)1074-7.

Database Chemcats. Chemical Abstracts Service. XP002307105. 'Interchim Intermediates' Jul. 9, 2002.

Database Chemcats. Chemical Abstracts Service. XP002401299. 'Enamine Screening Library' Jan. 24, 2006.

Dumas, J. 'Protein Kinase Inhibitors: Emerging Pharmacophores 1997-2000' Expert Opinion on Therapeutic Patents vol. 11 No. 3 pp. 405-429. XP002206851.

International Search Report re: PCT/US2005/038307 dated Oct. 19, 2006.

International Search Report re: PCT/US2006/014886 dated Nov. 2, 2006.

* cited by examiner

C-FMS KINASE INHIBITORS

RELATIONSHIP TO OTHER APPLICATIONS AND PRIORITY CLAIM

This application is a continuation-in-part of U.S. Ser. No. 10/831,216, filed Apr. 26, 2004, now U.S. Pat. No. 7,429,603, issued Sep. 30, 2008; which in turn claimed benefit under 35 U.S.C. §119(e) to Provisional Application No. 60/465,204, filed Apr. 25, 2003.

FIELD OF THE INVENTION

The invention relates to novel compounds that function as protein tyrosine kinase inhibitors. More particularly, the invention relates to novel compounds that function as inhibitors of c-fms kinase.

BACKGROUND OF THE INVENTION

Protein kinases are enzymes that serve as key components of signal transduction pathways by catalyzing the transfer of the terminal phosphate from ATP to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R over-expression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. One embodiment of the invention is directed to the novel compounds of Formula I:

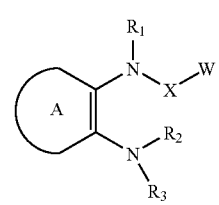

or a solvate, hydrate, tautomer or pharmaceutically acceptable salt thereof, wherein A is
  phenyl, naphthyl or biphenyl, each of which may be optionally substituted with one or more of —$C_{1-6}$ alkyl, —$C_{2-6}$ alkenyl, amino, aminoalkyl, hydroxyalkyl, alkoxyalkyl, sulfonamidoalkyl, alkylsulfonamidoalkyl, guanidinoalkyl, heteroaryl, alkoxyheteroaryl, aminoheteroaryl, halogen, hydroxy, —$CF_3$, alkoxy, aryl, aminoaryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$; -arylN$SO_2R_a$; or
  a 5- to 7-membered mono- or a 8- to 10-membered bicyclic heteroaromatic ring or bicyclic heterocyclic ring having from one to four heteroatoms selected from N, O or S, and may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$;

$R_1$ is
—H, aryl, —$COR_a$, —$COR_a$, —$COOR_a$, —$CONR_aR_b$, —$SO_2R_a$ or —$SO_2NR_aR_b$;

X is
—CO—, —C(=NH)—, —CS—, —CON($R_a$)—, —CS(N$R_a$)—, —$SO_2$— or —$CR_aR_b$—;

$R_2$ and $R_3$ are independently
—H, —$C_{1-6}$ alkyl, aryl, cycloalkyl, heterocyclyl, heteroaryl, —$COR_a$, —$COR_a$, —$COOR_a$, —$CONR_aR_b$, —$SO_2R_a$ or —$SO_2NR_aR_b$; or $R_2$ and $R_3$, taken together with the attached nitrogen, form
a 5- to 7-membered heterocyclic or heteroaromatic ring containing from one to three heteroatoms selected from N, O or S, which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$COOR_a$, —$CONR_aR_b$, —N($R_a$)$COR_b$, —$NO_2$, —$SO_2R_a$, —$SO_3R_a$ or —$SO_2NR_aR_b$; and W is
phenyl, naphthyl or biphenyl, each of which may be optionally substituted with one or more of $C_{1-4}$ alkyl, amino, aminoalkyl, alkylaminoalkyl, dialkylaminoalkyl, hydroxyalkyl, alkoxyalkyl, halogen, hydroxy, —$CF_3$, alkoxy, aryloxy, arylalkoxy, —$OCF_3$, —$COR_a$, —CN, —C(NH)$NH_2$, —$COOR_a$, —$CONR_aR_b$, —NH$COR_aR_b$, —$NHSO_2R_a$, —$NO_2$, —$SOR_a$, —$SO_3R_a$ or —$SO_2NR_aR_b$; or a 5- to 6-membered mono- or a 8- to 10-membered bicyclic heterocyclic or heteroaromatic ring having from one to four heteroatoms selected from N, O or S, and may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —C(NH)$NH_2$, —$COOR_a$, —$CONR_aR_b$, —N($R_a$)$COR_b$, —$NO_2$, —$SO_2R_a$, —$SO_3R_a$ or —$SO_2NR_aR_b$, wherein $R_a$ and $R_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

In another embodiment, the invention is directed to the novel compounds of Formula II:

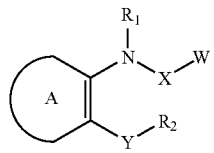

II or a solvate, hydrate, tautomer or pharmaceutically acceptable salt thereof, wherein A is
phenyl, naphthyl or biphenyl, each of which may be optionally substituted with one or more of —$C_{1-6}$ alkyl, —$C_{2-6}$ alkenyl, amino, aminoalkyl, hydroxyalkyl, alkoxyalkyl, sulfonamidoalkyl, alkylsulfonamidoalkyl, guanidinoalkyl, heteroaryl, alkoxyheteroaryl, aminoheteroaryl, halogen, hydroxy, —$CF_3$, alkoxy, aryl, aminoaryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —N($R_a$)$COR_b$, —$NO_2$, —$SO_2R_a$, —$SO_3R_a$ or —$SO_2NR_aR_b$; -arylNS$O_2R_a$; or a 5- to 7-membered mono- or a 8- to 10-membered bicyclic heteroaromatic ring or bicyclic heterocyclic ring having from one to four heteroatoms selected from N, O or S, and may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —N($R_a$)$COR_b$, —$NO_2$, —$SO_2R_8$, —$SO_3R_a$ or —$SO_2NR_aR_b$;

$R_1$ is
—H, aryl, —$COR_a$, —$COR_a$, —$COOR_a$, —$CONR_aR_b$, —$SO_2R_8$ or —$SO_2NR_aR_b$;

X is
—CO—, —C(=NH)—, —CS—, —CON($R_a$)—, —CS(N$R_a$)—, —$SO_2$— or —$CR_aR_b$—;

Y is
—S—, —SO—, —$SO_2$—, —O— or direct link;

$R_2$ is
alkyl, cycloalkyl, heterocyclyl, aryl or heteroaryl, each of which may be optionally substituted with one or more halogens or lower alkyl groups, preferably 1 or 2 methyl groups; and W is
phenyl, naphthyl or biphenyl, each of which may be optionally substituted with one or more of $C_{1-4}$ alkyl, amino, aminoalkyl, alkylaminoalkyl, dialkylaminoalkyl, hydroxyalkyl, alkoxyalkyl, halogen, hydroxy, —$CF_3$, alkoxy, aryloxy, arylalkoxy, —$OCF_3$, —$COR_a$, —CN, —C(NH)$NH_2$, —$COOR_a$, —$CONR_aR_b$, —NH$COR_aR_b$, —$NHSO_2R_a$, —$NO_2$, —$SOR_a$, —$SO_3R_a$ or —$SO_2NR_aR_b$; or a 5- to 6-membered mono- or a 8- to 10-membered bicyclic heterocyclic or heteroaromatic ring having from one to four heteroatoms selected from N, O or S, and may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —C(NH)$NH_2$, —$COOR_a$, —$CONR_aR_b$, —N($R_a$)$COR_b$, —$NO_2$, —$SO_2R_a$, —$SO_3R_a$ or —$SO_2NR_aR_b$, $R_a$ and $R_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

Yet another embodiment of the invention is directed to the compounds of Formula III:

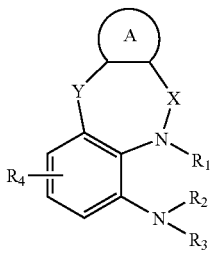

or a solvate, hydrate, tautomer or pharmaceutically acceptable salt thereof, wherein A is
  phenyl, naphthyl or biphenyl, each of which may be optionally substituted with one or more of —$C_{1-6}$ alkyl, —$C_{2-6}$ alkenyl, amino, aminoalkyl, hydroxyalkyl, alkoxyalkyl, sulfonamidoalkyl, alkylsulfonamidoalkyl, guanidinoalkyl, heteroaryl, alkoxyheteroaryl, aminoheteroaryl, halogen, hydroxy, —$CF_3$, alkoxy, aryl, aminoaryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$; -aryl$NSO_2R_a$;

X is
  —CO—, —C(=NH)—, —$SO_2$— or —CS—;

Y is
  direct bond, —$CH_2$—, —$CH_2CH_2$—, —CH=CH—, —$NR_a$—, —O—, —S—, —SO—, —$SO_2$—, —$CH_2O$—, —$OCH_2$—, —$NR_aCH_2$—, —$CH_2NR_a$—, —$CONR_a$— or —$NR_aCO$—;

$R_1$ is
  —H, aryl, —$COR_a$, —$COR_a$, —$COOR_a$, —$CONR_aR_b$, —$SO_2R_a$ or —$SO_2NR_aR_b$;

$R_2$ and $R_3$ are independently
  —H, —$C_{1-6}$ alkyl, aryl, cycloalkyl, heterocyclyl, heteroaryl, —$COR_a$, —$COR_a$, —$COOR_a$, —$CONR_aR_b$, —$SO_2R_a$ or —$SO_2NR_aR_b$; or $R_2$ and $R_3$, taken together with the attached nitrogen, form
  a 5- to 7-membered heterocyclic or heteroaromatic ring containing from one to three heteroatoms selected from N, O or S, which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, and $R_4$ is
  one or more of —H, —$C_1$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, $R_a$ and $R_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

The compounds of Formulae I and II are especially potent inhibitors of the c-fms protein tyrosine kinase. The compounds of Formula III are expected to exhibit similar inhibitory potencies.

The invention also relates to methods of inhibiting protein tyrosine kinase activity in a mammal by administration of a therapeutically effective amount of at least one compound of Formula I, II or III.

DETAILED DESCRIPTION OF THE INVENTION

The invention is directed to the novel compounds of Formula I:

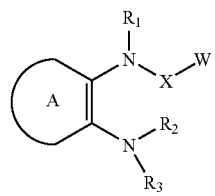

or a solvate, hydrate, tautomer or pharmaceutically acceptable salt thereof, wherein A is
  phenyl, naphthyl or biphenyl, each of which may be optionally substituted with one or more of —$C_{1-6}$ alkyl, —$C_{2-6}$ alkenyl, amino, aminoalkyl, hydroxyalkyl, alkoxyalkyl, sulfonamidoalkyl, alkylsulfonamidoalkyl, guanidinoalkyl, heteroaryl, alkoxyheteroaryl, aminoheteroaryl, halogen, hydroxy, —$CF_3$, alkoxy, aryl, aminoaryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$; -aryl$NSO_2R_a$; or
  a 5- to 7-membered mono- or a 8- to 10-membered bicyclic heteroaromatic ring or bicyclic heterocyclic ring having from one to four heteroatoms selected from N, O or S, and may be optionally substituted with one or more of —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$;

$R_1$ is
  —H, aryl, —$COR_a$, —$COR_a$, —$COOR_a$, $CONR_aR_b$, —$SO_2R_a$ or —$SO_2NR_aR_b$;

X is
  —CO—, —C(=NH)—, —CS—, —CON($R_a$)—, —CS(N$R_a$)—, —$SO_2$— or —$CR_aR_b$—;

$R_2$ and $R_3$ are independently
  —H, —$C_{1-6}$ alkyl, aryl, cycloalkyl, heterocyclyl, heteroaryl, —$COR_a$, —$COR_a$, —$COOR_a$, —$CONR_aR_b$, —$SO_2R_a$ or —$SO_2NR_aR_b$; or $R_2$ and $R_3$, taken together with the attached nitrogen, form
  a 5- to 7-membered heterocyclic or heteroaromatic ring containing from one to three heteroatoms selected from N, O or S, which may be optionally substituted with —$C_{1-6}$ alkyl, amino, aminoalkyl, hydroxyalkyl, alkoxyalkyl, heteroaryl, halogen, hydroxy, —CF₃, alkoxy, aryl, aralkyl, heteroaralkyl, aryloxy, arylalkoxy, —OCF₃, —OCO-alkyl, —OCO-alkylamino, —OCO-alkylamido, —COR$_a$, —CN, —COOR$_a$, —CONR$_a$R$_b$, N(R$_a$) COR$_b$, —NO₂, —SO₂R$_a$, —SO₃R$_a$ or —SO₂NR$_a$R$_b$; and W is
phenyl, naphthyl or biphenyl, each of which may be optionally substituted with one or more of C$_{1-4}$ alkyl, amino, aminoalkyl, alkylaminoalkyl, dialkylaminoalkyl, hydroxyalkyl, alkoxyalkyl, halogen, hydroxy, —CF₃, alkoxy, aryloxy, arylalkoxy, —OCF₃, —COR$_a$, —CN, —C(NH)NH₂, —COOR$_a$, —CONR$_a$R$_b$, —NHCOR$_a$R$_b$, —NHSO₂R$_a$, —NO₂, —SOR$_a$, —SO₃R$_a$ or —SO₂NR$_a$R$_b$; or a 5- to 6-membered mono- or a 8- to 10-membered bicyclic heterocyclic or heteroaromatic ring having from one to four heteroatoms selected from N, O or S, and may be optionally substituted with —C$_{1-6}$ alkyl, amino, aminoalkyl, hydroxyalkyl, alkoxyalkyl, heteroaryl, halogen, hydroxy, —CF₃, alkoxy, aryl, aralkyl, heteroaralkyl, aryloxy, arylalkoxy, —OCF₃, —OCO-alkyl, —OCO-alkylamino, —OCO-alkylamido, —COR$_a$, —CN, —C(NH)NH₂, —COOR$_a$, —CONR$_a$R$_b$, —N(R$_a$)COR$_b$, —NO₂, —SO₂R$_a$, —SO₃R$_a$ or —SO₂NR$_a$R$_b$, wherein R$_a$ and R$_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

In another embodiment, the invention is directed to the novel compounds of Formula II:

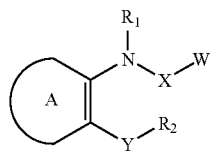

II or a solvate, hydrate, tautomer or pharmaceutically acceptable salt thereof, wherein A is
phenyl, naphthyl or biphenyl, each of which may be optionally substituted with one or more of —C$_{1-6}$ alkyl, —C$_{2-6}$ alkenyl, amino, aminoalkyl, hydroxyalkyl, alkoxyalkyl, sulfonamidoalkyl, alkylsulfonamidoalkyl, guanidinoalkyl, heteroaryl, alkoxyheteroaryl, aminoheteroaryl, halogen, hydroxy, —CF₃, alkoxy, aryl, aminoaryl, aralkyl, heteroaralkyl, aryloxy, arylalkoxy, —OCF₃, —OCO-alkyl, —COR$_a$, —CN, —C(NH)NH₂, —COOR$_a$, —CONR$_a$R$_b$, —N(R$_a$)COR$_b$, —NO₂, —SO₂R$_a$, —SO₃R$_a$ or —SO₂NR$_a$R$_b$; -arylNSO₂R$_a$; or a 5- to 7-membered mono- or a 8- to 10-membered heteroaromatic ring or bicyclic heterocyclic ring having from one to four heteroatoms selected from N, O or S, and may be optionally substituted with one or more of —C$_{1-6}$ alkyl, amino, aminoalkyl, hydroxyalkyl, alkoxyalkyl, sulfonamidoalkyl, guanidinoalkyl, heteroaryl, halogen, hydroxy, —CF₃, alkoxy, aryl, aralkyl, heteroaralkyl, aryloxy, arylalkoxy, —OCF₃, —OCO-alkyl, —COR$_a$, —CN, —C(NH)NH₂, —COOR$_a$, —CONR$_a$R$_b$, —N(R$_a$)COR$_b$, —NO₂, —SO₂R$_a$, —SO₃R$_a$ or —SO₂NR$_a$R$_b$;

R₁ is
—H, aryl, —COR$_a$, —COR$_a$, —COOR$_a$, —CONR$_a$R$_b$, —SO₂R$_a$ or —SO₂NR$_a$R$_b$;

X is
—CO—, —C(=NH)—, —CS—, —CON(R$_a$)—, —CS(NR$_a$)—, —SO₂— or —CR$_a$R$_b$—;

Y is
—S—, —SO—, —SO₂—, —O— or direct link;

R₂ is
alkyl, cycloalkyl, heterocyclyl, aryl or heteroaryl, each of which may be optionally substituted with one or more halogens or lower alkyl groups, preferably 1 or 2 methyl groups; and W is
phenyl, naphthyl or biphenyl, each of which may be optionally substituted with one or more of C$_{1-4}$ alkyl, amino, aminoalkyl, alkylaminoalkyl, dialkylaminoalkyl, hydroxyalkyl, alkoxyalkyl, halogen, hydroxy, —CF₃, alkoxy, aryloxy, arylalkoxy, —OCF₃, —COR$_a$, —CN, —C(NH)NH₂, —COOR$_a$, —CONR$_a$R$_b$, —NHCOR$_a$R$_b$, —NHSO₂R$_a$, —NO₂, —SOR$_a$, —SO₃R$_a$ or —SO₂NR$_a$R$_b$; or a 5- to 6-membered mono- or a 8- to 10-membered bicyclic heterocyclic or heteroaromatic ring having from one to four heteroatoms selected from N, O or S, and may be optionally substituted with —C$_{1-6}$ alkyl, amino, aminoalkyl, hydroxyalkyl, alkoxyalkyl, heteroaryl, halogen, hydroxy, —CF₃, alkoxy, aryl, aralkyl, heteroaralkyl, aryloxy, arylalkoxy, —OCF₃, —OCO-alkyl, —OCO-alkylamino, —OCO-alkylamido, —COR$_a$, —CN, —C(NH)NH₂, —COOR$_a$, —CONR$_a$R$_b$, —N(R$_a$)COR$_b$, —NO₂, —SO₂R$_a$, —SO₃R$_a$ or —SO₂NR$_a$R$_b$, R$_a$ and R$_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

Yet another embodiment of the invention is directed to the compounds of Formula III:

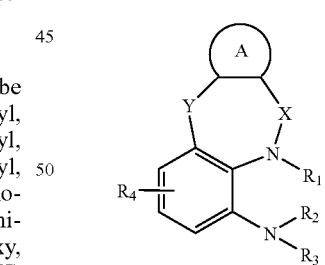

III or a solvate, hydrate, tautomer or pharmaceutically acceptable salt thereof, wherein A is
phenyl, naphthyl or biphenyl, each of which may be optionally substituted with one or more of —C$_{1-6}$ alkyl, —C$_{2-6}$ alkenyl, amino, aminoalkyl, hydroxyalkyl, alkoxyalkyl, sulfonamidoalkyl, alkylsulfonamidoalkyl, guanidinoalkyl, heteroaryl, alkoxyheteroaryl, aminoheteroaryl, halogen, hydroxy, —CF₃, alkoxy, aryl, aminoaryl, aralkyl, heteroaralkyl, aryloxy, arylalkoxy, —OCF₃, —OCO-alkyl, —COR$_a$, —CN, —C(NH)

$NH_2$, —$COOR_a$, —$CONR_aR_b$, —$N(R_a)COR_b$, —$NO_2$, —$SO_2R_a$, —$SO_3R_a$ or —$SO_2NR_aR_b$; -arylN$SO_2R_a$;

X is
—CO—, —C(=NH)—, —$SO_2$— or —CS—;

Y is
direct bond, —$CH_2$—, —$CH_2CH_2$—, —CH=CH—, —$NR_a$—, —O—, —S—, —SO—, —$SO_2$—, —$CH_2O$—, —$OCH_2$—, —$NR_aCH_2$—, —$CH_2NR_a$—, —$CONR_a$— or —$NR_aCO$—;

$R_1$ is
—H, aryl, —$COR_a$, —$COR_a$, —$COOR_a$, —$CONR_aR_b$, —$SO_2R_a$ or —$SO_2NR_aR_b$;

$R_2$ and $R_3$ are independently
—H, —$C_{1-6}$ alkyl, aryl, cycloalkyl, heterocyclyl, heteroaryl, —$COR_a$, —$COR_a$, —$COOR_a$, —$CONR_aR_b$, —$SO_2R_a$ or —$SO_2NR_aR_b$; or $R_2$ and $R_3$, taken together with the attached nitrogen, form
a 5- to 7-membered heterocyclic or heteroaromatic ring containing from one to three heteroatoms selected from N, O or S, which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, and $R_4$ is
one or more of —H, —$C_{1-6}$ alkyl, amino, aminoalkyl, hydroxyalkyl, alkoxyalkyl, sulfonamidoalkyl, guanidinoalkyl, heteroaryl, halogen, hydroxy, —$CF_3$, alkoxy, aryl, aralkyl, heteroaralkyl, aryloxy, arylalkoxy, —$OCF_3$, —OCO-alkyl, —$COR_a$, —CN, —$COOR_a$, —$CONR_aR_b$, —$N(R_a)COR_b$, —$NO_2$, —$SO_2R_a$, —$SO_3R_a$ or —$SO_2NR_8R_b$, $R_a$ and $R_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

Preferred compounds of Formula I are those wherein

A is phenyl;

$R_1$ is —H; and $R_2$ and $R_3$, taken together with the attached nitrogen, form a piperidine, piperazine, morpholine, thiomorpholine, pyrrolidine, pyrroline, pyrazolidine, pyrazoline, imidazolidine or imidazoline ring which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

Particularly preferred compounds of Formula I are those wherein

A is phenyl;

$R_1$ is —H;

$R_2$ and $R_3$, taken together with the attached nitrogen, form a piperidine, piperazine, morpholine, thiomorpholine, pyrrolidine, pyrroline, pyrazolidine, pyrazoline, imidazolidine or imidazoline ring which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$; and W is a phenyl, furan, thiophene, isoxazole, pyrrole, oxazole, thiazole, imidazole, pyrazole, isothiazole, triazole, pyridine, pyridazine, pyrimidine, pyrazine or triazine ring which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

Preferred compounds of Formula II are those wherein

A is phenyl;

$R_1$ is —H; and

W is a phenyl, furan, thiophene, isoxazole, pyrrole, oxazole, thiazole, imidazole, pyrazole, isothiazole, triazole, pyridine, pyridazine, pyrimidine, pyrazine or triazine ring which may be optionally substituted with —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$, wherein $R_a$ and $R_b$ are independently hydrogen, alkyl, cycloalkyl, haloalkyl, aryl, aralkyl, heteroaralkyl or heteroaryl.

Particularly preferred are compounds of Formula II wherein

A is phenyl, pyridinyl, pyridazinyl, or piperidinyl; wherein

A can be optionally substituted with one or more of —$C_{1-6}$ alkyl, —$C_{2-6}$ alkenyl, amino, aminoalkyl, hydroxyalkyl, alkoxyalkyl, sulfonamidoalkyl, alkylsulfonamidoalkyl, guanidinoalkyl, heteroaryl, alkoxyheteroaryl, aminoheteroaryl, halogen, hydroxy, —$CF_3$, alkoxy, aryl, aminoaryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$; -arylN$SO_2R_a$; or -alkyl $SO_2NR_aR_b$;

$R_1$ is —H;

X is —CO—;

Y is a direct link;

$R_2$ is cycloalkyl, heterocyclyl, or heteroaryl; particularly preferred as $R_2$ are the moieties cyclohexenyl, dimethylcyclohexenyl, methylimidazolyl, piperidinyl, and methylpiperidinyl;

W is imidazolyl, optionally substituted with one or two —$C_{1-6}$ alkyl, amino, aminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —COR$_a$, —CN, —C(NH)NH$_2$, —COOR$_a$, —CONR$_a$R$_b$, —N(R$_a$)COR$_b$, —NO$_2$, —SO$_2$R$_a$, —SO$_3$R$_a$ or —SO$_2$NR$_a$R$_b$;

particularly preferred is W is imidazolyl optionally substituted with one or two of the following: —C$_{1-6}$ alkyl, amino, aminoalkyl, alkylaminoalkyl, dialkylaminoalkyl, hydroxyalkyl, alkoxyalkyl, cyano, or —CONR$_a$R$_b$; and R$_a$ and R$_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

Still more preferred are compounds of Formula II wherein

A is phenyl, pyridinyl, pyridazinyl, or piperidinyl; wherein

A can be optionally substituted with one or more of —C$_{1-6}$ alkyl, —C$_{2-6}$ alkenyl, amino, aminoalkyl, hydroxyalkyl, alkoxyalkyl, sulfonamidoalkyl, alkylsulfonamidoalkyl, guanidinoalkyl, heteroaryl, alkoxyheteroaryl, aminoheteroaryl, halogen, hydroxy, —CF$_3$, alkoxy, aryl, aminoaryl, aminoaryl, aralkyl, heteroalkyl, aryloxy, arylalkoxy, —OCF$_3$, —OCO-alkyl, —COR$_a$, —CN, —C(NH)NH$_2$, —COOR$_a$, —CONR$_a$R$_b$, —N(R$_a$)COR$_b$, —NO$_2$, SO$_2$R$_a$, —SO$_3$R$_a$ or —SO$_2$NR$_a$R$_b$; -arylNSO$_2$R$_a$; or -alkyl SO$_2$NR$_a$R$_b$;

R$_1$ is —H;

X is —CO—;

Y is a direct link;

R$_2$ is cyclohexenyl, dimethylcyclohexenyl, methylimidazolyl, piperidinyl, or methylpiperidinyl;

W is imidazolyl optionally substituted with one or two of the following: —C$_{1-6}$ alkyl, amino, aminoalkyl, alkylaminoalkyl, dialkylaminoalkyl, hydroxyalkyl, alkoxyalkyl, cyano, or —CONR$_a$R$_b$; and R$_a$ and R$_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

Even more preferred are compounds of Formula II wherein

A is phenyl, or pyridinyl; wherein

A can be unsubstituted or optionally substituted with bromo, amino, aminoalkyl, aminoaryl, hydroxyalkyl, alkoxyalkyl, pyridinyl, N-oxypyrindinyl, methoxy pyrindinyl, —COR$_a$, —CONR$_a$R$_b$, -arylNSO$_2$R$_a$; -alkyl SO$_2$NR$_a$R$_b$; —SO$_2$R$_a$, tetrazolyl, alkyltetrazolyl, or alkyltetrazolylalkyl NR$_a$R$_b$;

R$_1$ is —H;

X is —CO—;

Y is a direct link;

R$_2$ is cyclohexenyl, dimethylcyclohexenyl, methylimidazolyl, piperidinyl, or methylpiperidinyl;

W is imidazolyl optionally substituted with one or two of the following: —C$_{1-6}$ alkyl, amino, aminoalkyl, alkylaminoalkyl, dialkylaminoalkyl, hydroxyalkyl, alkoxyalkyl, cyano, or —CONR$_a$R$_b$; and R$_a$ and R$_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

It is expected that the preferred compounds of Formula III will have similar or identical R$_2$ and R$_3$ substituents as compared to the preferred compounds of Formulae I and II.

The most preferred compounds of Formula I include, but are not limited to, 5-nitro-furan-2-carboxylic acid (2-piperidin-1-yl-phenyl)-amide; isoxazole-5-carboxylic acid (2-piperidin-1-yl-phenyl)-amide; 5-nitro-furan-2-carboxylic acid (5-hydroxymethyl-2-piperidin-1-yl-phenyl)-amide; 5-nitro-furan-2-carboxylic acid [2-(3-methyl-piperidin-1-yl)-phenyl]-amide; 4-nitro-pyridine-2-carboxylic acid (2-piperidin-1-yl-phenyl)-amide; 5-nitro-furan-2-carboxylic acid (2-morpholin-4-yl-phenyl)-amide; 5-chloro-furan-2-carboxylic acid (2-piperidin-1-yl-phenyl)-amide; 5-nitro-furan-2-carboxylic acid [2-(trans-2,6-dimethyl-morpholin-4-yl)-phenyl]-amide; 3-nitro-N-(2-piperidin-1-yl-phenyl)-benzamide; 5-bromo-furan-2-carboxylic acid (2-piperidin-1-yl-phenyl)-amide; 5-acetyl-thiophene-2-carboxylic acid (2-piperidin-1-yl-phenyl)-amide; 5-nitro-furan-2-carboxylic acid [2-(cis-2,6-dimethyl-morpholin-4-yl)-phenyl]-amide; 4-nitro-2H-pyrazole-3-carboxylic acid (2-piperidin-1-yl-phenyl)-amide; 5-formyl-furan-2-carboxylic acid (2-piperidin-1-yl-phenyl)-amide; 5-(2-piperidin-1-yl-phenylcarbamoyl)-furan-2-carboxylic acid; isoxazole-5-carboxylic acid (2-morpholin-4-yl-phenyl)-amide; 5-cyano-furan-2-carboxylic acid (2-piperidin-1-yl-phenyl)-amide; 5-nitro-furan-2-carboxylic acid [2-(4-methyl-piperidin-1-yl)-phenyl]-amide; 5-nitro-furan-2-carboxylic acid [2-(4-methyl-piperazin-1-yl)-phenyl]-amide; 5-nitro-furan-2-carboxylic acid [2-(4-hydroxy-piperidin-1-yl)-phenyl]-amide; 5-nitro-furan-2-carboxylic acid [2-(4-hydroxymethyl-piperidin-1-yl)-phenyl]-amide; 5-nitro-furan-2-carboxylic acid (2-azepan-1-yl-phenyl)-amide; 5-cyano-furan-2-carboxylic acid (5-hydroxymethyl-2-piperidin-1-yl-phenyl)-amide; 5-cyano-furan 2-carboxylic acid [2-(4-methyl-piperidin-1-yl)-phenyl]-amide; 5-cyano-furan-2-carboxylic acid [2-(4-hydroxymethyl-piperidin-1-yl)-phenyl]-amide; 5-cyano-furan-2-carboxylic acid {2-[4-(2-hydroxy-ethyl)-piperidin-1-yl]-phenyl}-amide; 5-cyano-furan-2-carboxylic acid [5-hydroxymethyl-2-(4-methyl-piperidin-1-yl)-phenyl]-amide; 5-cyano-furan-2-carboxylic acid [5-hydroxymethyl-2-(4-hydroxymethyl-piperidin-1-yl)-phenyl]-amide; 5-cyano-furan-2-carboxylic acid [2-(4-ethyl-piperidin-1-yl)-5-hydroxymethyl-phenyl]-amide; 5-cyano-furan-2-carboxylic acid {2-[4-(2-hydroxy-ethyl)-piperidin-1-yl]-5-hydroxymethyl-phenyl}-amide; 5-cyano-furan-2-carboxylic acid [2-(4-ethyl-piperidin-1-yl)-phenyl]-amide; 4-nitro-1H-pyrrole-2-carboxylic acid [2-(4-ethyl-piperidin-1-yl)-phenyl]-amide; 4-nitro-1H-pyrrole-2-carboxylic acid [2-(4-methyl-piperidin-1-yl)-phenyl]-amide; 4-nitro-1H-pyrrole-2-carboxylic acid [5-hydroxymethyl-2-(4-methyl-piperidin-1-yl)-phenyl]-amide; 4-nitro-1H-pyrrole-2-carboxylic acid [5-hydroxymethyl-2-(4-ethyl-piperidin-1-yl)-phenyl]-amide; 4-nitro-1H-pyrrole-2-carboxylic acid {2-[4-(2-hydroxy-ethyl)-piperidin-1-yl]-5-hydroxymethyl-phenyl}-amide; 4-cyano-1H-pyrrole-2-carboxylic acid (2-piperidin-1-yl-phenyl)-amide; 4-cyano-1H-pyrrole-2-carboxylic acid [2-(4-ethyl-piperidin-1-yl)-phenyl]-amide; 4-cyano-1H-pyrrole-2-carboxylic acid [2-(4-methyl-piperidin-1-yl)-phenyl]-amide; 4-cyano-1H-pyrrole-2-carboxylic acid [5-hydroxymethyl-2-(4-methyl-piperidin-1-yl)-phenyl]-amide; 4-cyano-1H-pyrrole-2-carboxylic acid [5-hydroxymethyl-2-(4-ethyl-piperidin-1-yl)-phenyl]-amide; 4-cyano-1H-pyrrole-2-carboxylic acid {2-[4-(2-hydroxy-ethyl)-piperidin-1-yl]-5-hydroxymethyl-phenyl}-amide; 5-cyano-furan-2-carboxylic acid (5-methylsulfonamidomethyl-2-piperidin-1-yl-phenyl)-amide; 5-cyano-furan-2-carboxylic acid (5-guanidinomethyl-2-piperidin-1-yl-phenyl)-amide; 5-cyano-furan-2-carboxylic acid [5-(4-methyl-piperazin-1-ylmethyl)-2-piperidin-1-yl-phenyl]-amide; 5-cyano-furan-2-carboxylic acid (4-fluoro-2-piperidin-1-yl-phenyl)-amide; 5-cyano-furan-2-carboxylic acid (4-chloro-2-piperidin-1-yl-phenyl)-amide; 5-cyano-furan-2-carboxylic acid (5-cyano-2-piperidin-1-yl-phenyl)-amide; 5-cyano-furan-2-carboxylic acid {5-[(2,3-dihydroxy-propylamino)-methyl]-2-piperidin-1-yl-phenyl}-amide; 5-nitro-2H-pyrazole-3-carboxylic acid (2-piperidin-1-yl-phenyl)-amide and pharmaceutically acceptable salts thereof.

The most preferred compounds of Formula II include 5-nitro-furan-2-carboxylic acid [2-(2-chloro-1,1,2-trifluoro-ethylsulfanyl)-phenyl]-amide; 5-nitro-furan-2-carboxylic acid (2-ethoxyphenyl)-amide and pharmaceutically acceptable salts thereof.

Even more preferred compounds of Formula II include 4-Cyano-1H-imidazole-2-carboxylic acid (4-bromo-2-cyclohex-1-enyl-phenyl)-amide; 4-Cyano-1H-imidazole-2-carboxylic acid [2-cyclohex-1-enyl-4-(1-hydroxy-1-methyl-ethyl)-phenyl]-amide; 4-Cyano-1H-imidazole-2-carboxylic acid [2-cyclohex-1-enyl-4-(1-methoxy-1-methyl-ethyl)-phenyl]-amide; 4-Cyano-1H-imidazole-2-carboxylic acid [4-(1-amino-1-methyl-ethyl)-2-cyclohex-1-enyl-phenyl]-amide, acetic acid salt; 4-Cyano-1H-imidazole-2-carboxylic acid [4-(6-amino-pyridin-3-yl)-2-cyclohex-1-enyl-phenyl]-amide, trifluoroacetic acid salt; 5-Cyano-1H-imidazole-2-carboxylic acid [2-cyclohex-1-enyl-4-(1-oxy-pyridin-4-yl)-phenyl]-amide; 5-Cyano-1H-imidazole-2-carboxylic acid (2-cyclohex-1-enyl-4-pyridin-4-yl-phenyl)-amide; 4-Cyano-1H-imidazole-2-carboxylic acid [2-cyclohex-1-enyl-4-(pyridin-3-yl)-phenyl]-amide; 4-Cyano-1H-imidazole-2-carboxylic acid [2-cyclohex-1-enyl-4-(1-oxy-pyridin-3-yl)-phenyl]-amide; 4-Cyano-1H-imidazole-2-carboxylic acid [2-cyclohex-1-enyl-4-(1-oxy-pyridin-2-yl)-phenyl]-amide; 4-Cyano-1H-imidazole-2-carboxylic acid (2-cyclohex-1-enyl-4-pyridin-2-yl-phenyl)-amide; 4-Cyano-1H-imidazole-2-carboxylic acid (2-cyclohex-1-enyl-4-isopropyl-phenyl)-amide; 4-Cyano-1H-imidazole-2-carboxylic acid (2-piperidin-1-yl-phenyl)-amide, trifluoroacetic acid salt; 4-Cyano-5-(1-hydroxy-1-methyl-ethyl)-1H-imidazole-2-carboxylic acid (4-bromo-2-cyclohex-1-enyl-phenyl)-amide; 4-Cyano-1H-imidazole-2-carboxylic acid (4-acetyl-2-cyclohex-1-enyl-phenyl)-amide; 4-Cyano-1H-imidazole-2-carboxylic acid (4-carbamoyl-2-cyclohex-1-enyl-phenyl)-amide; 4-Cyano-1H-imidazole-2-carboxylic acid [4-carbamoyl-2-(4,4-dimethyl-cyclohex-1-enyl)-phenyl]-amide; 4-Cyano-1H-imidazole-2-carboxylic acid (4'-amino-3-cyclohex-1-enyl-biphenyl-4-yl)-amide, trifluoroacetic acid salt; 4-Cyano-1H-imidazole-2-carboxylic acid (3-cyclohex-1-enyl-4'-methanesulfonylamino-biphenyl-4-yl)-amide; 4-Cyano-1H-imidazole-2-carboxylic acid (3-cyclohex-1-enyl-biphenyl-4-yl)-amide; 4-Cyano-1H-imidazole-2-carboxylic acid [5-acetyl-2-(4,4-dimethyl-cyclohex-1-enyl)-phenyl]-amide; 4-Cyano-1H-imidazole-2-carboxylic acid [2-(4,4-dimethyl-cyclohex-1-enyl)-5-(1-hydroxy-1-methyl-ethyl)-phenyl]-amide; 4-Cyano-1H-imidazole-2-carboxylic acid [4-bromo-2-(4,4-dimethyl-cyclohex-1-enyl)-phenyl]-amide; 4-Cyano-1H-imidazole-2-carboxylic acid [2-(4,4-dimethyl-cyclohex-1-enyl)-4-(1-hydroxy-1-methyl-ethyl)-phenyl]-amide; 4-Cyano-1H-imidazole-2-carboxylic acid [2-cyclohex-1-enyl-4-(2-hydroxy-2-methyl-propyl)-phenyl]-amide; 4-Cyano-1H-imidazole-2-carboxylic acid [2-(4,4-dimethyl-cyclohex-1-enyl)-4-methanesulfonyl-phenyl]-amide; 5-Cyano-1H-imidazole-2-carboxylic acid [2-cyclohex-1-enyl-4-(2-hydroxy-ethyl)-phenyl]-amide; 5-Cyano-1H-imidazole-2-carboxylic acid [2-(4,4-dimethyl-cyclohex-1-enyl)-4-(2-hydroxy-ethyl)-phenyl]-amide; 5-Cyano-1H-imidazole-2-carboxylic acid (6-cyclohex-1-enyl-benzo[1,3]dioxol-5-yl)-amide; 5-Cyano-1H-imidazole-2-carboxylic acid [2-(3-methyl-3H-imidazol-4-yl)-phenyl]-amide trifluoroacetic acid salt; 4-Cyano-1H-imidazole-2-carboxylic acid [2-(4-methyl-piperidin-1-yl)-phenyl]-amide trifluoroacetic acid salt; 4-Cyano-1H-imidazole-2-carboxylic acid [2-(4,4-dimethyl-cyclohex-1-enyl)-pyridin-3-yl]-amide trifluoroacetic acid salt; 4-Cyano-1H-imidazole-2-carboxylic acid (2-cyclohex-1-enyl-pyridin-3-yl)-amide trifluoroacetic acid salt; 4-Cyano-1H-imidazole-2-carboxylic acid [2-cyclohex-1-enyl-4-(morpholine-4-sulfonyl)-phenyl]-amide; 4-Cyano-1H-imidazole-2-carboxylic acid [(4,4-dimethyl-cyclohex-1-enyl)-4-sulfamoyl-phenyl]-amide; 4-Cyano-1H-imidazole-2-carboxylic acid [2-(4,4-dimethyl-cyclohex-1-enyl)-4-(2-sulfamoyl-ethyl)-phenyl]-amide; 4-Cyano-1H-imidazole-2-carboxylic acid [2-cyclohex-1-enyl-4-(2-sulfamoyl-ethyl)-phenyl]-amide trifluoroacetic acid salt; 5-Cyano-1H-imidazole-2-carboxylic acid (2-cyclohex-1-enyl-4-sulfamoyl-phenyl)-amide trifluoroacetic acid salt; 5-Cyano-1H-imidazole-2-carboxylic acid (3-cyclohex-1-enyl-4'-dimethylsulfamoylbiphenyl-4-yl)-amide; 5-Cyano-1H-imidazole-2-carboxylic acid [2-(4,4-dimethyl-cyclohex-1-enyl)-4-(6-methoxy-pyridin-3-yl)-phenyl]-amide; 5-Cyano-1H-imidazole-2-carboxylic acid [2-(dimethyl-cyclohex-1-enyl)-6-(1-hydroxy-1-methyl-ethyl)-pyridin-3-yl]-amide; 5-Cyano-1H-imidazole-2-carboxylic acid [2-(4,4-dimethyl-cyclohex-1-enyl)-4-(1H-tetrazol-5-ylmethyl)-phenyl]-amide; 5-Cyano-1H-imidazole-2-carboxylic acid [4-[1-(2-dimethylamino-ethyl)-1H-tetrazol-5-ylmethyl]-2-(4,4-dimethyl-cyclohex-1-enyl)-phenyl]-amide trifluoroacetic acid salt; 5-Cyano-1H-imidazole-2-carboxylic acid [4-[2-(2-dimethylamino-ethyl)-2H-tetrazol-5-ylmethyl]-2-(4,4-dimethyl-cyclohex-1-enyl)-phenyl]-amide trifluoroacetic acid salt; 5-Cyano-1H-imidazole-2-carboxylic acid [2-cyclohex-1-enyl-4-(1H-tetrazol-5-ylmethyl)-phenyl]-amide; 5-Cyano-1H-imidazole-2-carboxylic acid [2-(4,4-dimethyl-cyclohex-1-enyl)-4-(1H-tetrazol-5-yl)-phenyl]-amide; 5-Cyano-1H-imidazole-2-carboxylic acid [2-cyclohex-1-enyl-4-(1H-tetrazol-5-yl)-phenyl]-amide; 5-Cyano-1-(2-dimethylamino-ethyl)-1H-imidazole-2-carboxylic acid {2-cyclohex-1-enyl-4-[1-(2-dimethylamino-ethyl)-1H-tetrazol-5-yl]-phenyl}-amide; [4-[(4-Cyano-1H-imidazole-2-carbonyl)-amino]-3-(4,4-dimethyl-cyclohex-1-enyl)-benzoyl]-L-glutamic acid; 3H-Imidazole-2,4-dicarboxylic acid 4-amide 2-([2-(4,4-dimethyl-cyclohex-1-enyl)-phenyl]-amide); 3H-Imidazole-2,4-dicarboxylic acid 2-amide 4-{[2-(4,4-dimethyl-cyclohex-1-enyl)-phenyl]-amide}; 2-Cyano-3H-imidazole-4-carboxylic acid [2-(4,4-dimethyl-cyclohex-1-enyl)-phenyl]-amide; 4-Cyano-1H-imidazole-2-carboxylic acid (4,4-dimethyl-3,4,5,6-tetrahydro-2H-[1,2']bipyridinyl-3'-yl)-amide trifluoroacetic acid salt; 5-Cyano-1H-imidazole-2-carboxylic acid (3-piperidin-1-yl-pyridazin-4-yl)-amide; 4-[(4-Cyano-1H-imidazole-2-carbonyl)-amino]-3-(4,4-dimethyl-cyclohex-1-enyl)-benzoic acid; 4-Cyano-1H-imidazole-2-carboxylic acid [4-dimethylcarbamoyl-2-(4,4-dimethyl-cyclohex-1-enyl)-phenyl]-amide; 4-Cyano-1H-imidazole-2-carboxylic acid [2-(4,4-dimethyl-cyclohex-1-enyl)-phenyl]-amide; and 5-Cyano-1H-imidazole-2-carboxylic acid [2-(4,4-dimethyl-cyclohex-1-enyl)-4-(1-hydroxy-ethyl)-phenyl]-amide.

Of the above compounds, the most preferred are the following:

4-Cyano-1H-imidazole-2-carboxylic acid [2-cyclohex-1-enyl-4-(1-hydroxy-1-methyl-ethyl)-phenyl]-amide;

4-Cyano-1H-imidazole-2-carboxylic acid [2-cyclohex-1-enyl-4-(1-methoxy-1-methyl-ethyl)-phenyl]-amide;

4-Cyano-1H-imidazole-2-carboxylic acid [4-(1-amino-1-methyl-ethyl)-2-cyclohex-1-enyl-phenyl]-amide, acetic acid salt;

4-Cyano-1H-imidazole-2-carboxylic acid [4-(6-amino-pyridin-3-yl)-2-cyclohex-1-enyl-phenyl]-amide, trifluoroacetic acid salt;

5-Cyano-1H-imidazole-2-carboxylic acid [2-cyclohex-1-enyl-4-(1-oxy-pyridin-4-yl)-phenyl]-amide;
5-Cyano-1H-imidazole-2-carboxylic acid (2-cyclohex-1-enyl-4-pyridin-4-yl-phenyl)-amide;
4-Cyano-1H-imidazole-2-carboxylic acid [2-cyclohex-1-enyl-4-(pyridin-3-yl)-phenyl]-amide;
4-Cyano-1H-imidazole-2-carboxylic acid [2-cyclohex-1-enyl-4-(1-oxy-pyridin-3-yl)-phenyl]-amide;
4-Cyano-1H-imidazole-2-carboxylic acid [2-cyclohex-1-enyl-4-(1-oxy-pyridin-2-yl)-phenyl]-amide;
4-Cyano-1H-imidazole-2-carboxylic acid (2-cyclohex-1-enyl-4-pyridin-2-yl-phenyl)-amide;
4-Cyano-1H-imidazole-2-carboxylic acid (2-cyclohex-1-enyl-4-isopropyl-phenyl)-amide;
4-Cyano-1H-imidazole-2-carboxylic acid [2-(4,4-dimethyl-cyclohex-1-enyl)-4-(1-hydroxy-1-methyl-ethyl)-phenyl]-amide;
4-Cyano-1H-imidazole-2-carboxylic acid [2-cyclohex-1-enyl-4-(2-hydroxy-2-methyl-propyl)-phenyl]-amide;
4-Cyano-1H-imidazole-2-carboxylic acid [2-(4,4-dimethyl-cyclohex-1-enyl)-4-methanesulfonyl-phenyl]-amide;
5-Cyano-1H-imidazole-2-carboxylic acid [2-cyclohex-1-enyl-4-(2-hydroxy-ethyl)-phenyl]-amide;
5-Cyano-1H-imidazole-2-carboxylic acid [2-(4,4-dimethyl-cyclohex-1-enyl)-4-(2-hydroxy-ethyl)-phenyl]-amide;
4-Cyano-1H-imidazole-2-carboxylic acid [2-(4-methyl-piperidin-1-yl)-phenyl]-amide trifluoroacetic acid salt;
4-Cyano-1H-imidazole-2-carboxylic acid [2-(4,4-dimethyl-cyclohex-1-enyl)-pyridin-3-yl]-amide trifluoroacetic acid salt;
4-Cyano-1H-imidazole-2-carboxylic acid [2-(4,4-dimethyl-cyclohex-1-enyl)-4-(2-sulfamoyl-ethyl)-phenyl]-amide;
4-Cyano-1H-imidazole-2-carboxylic acid [2-cyclohex-1-enyl-4-(2-sulfamoyl-ethyl)-phenyl]-amide trifluoroacetic acid salt;
4-Cyano-1H-imidazole-2-carboxylic acid (4,4-dimethyl-3,4,5,6-tetrahydro-2H-[1,2']bipyridinyl-3'-yl)-amide trifluoroacetic acid salt; and
4-Cyano-1H-imidazole-2-carboxylic acid [2-(4,4-dimethyl-cyclohex-1-enyl)-phenyl]-amide.

The even most preferred compounds are the following:
4-Cyano-1H-imidazole-2-carboxylic acid [2-cyclohex-1-enyl-4-(1-hydroxy-1-methyl-ethyl)-phenyl]-amide;
4-Cyano-1H-imidazole-2-carboxylic acid [4-(1-amino-1-methyl-ethyl)-2-cyclohex-1-enyl-phenyl]-amide, acetic acid salt;
4-Cyano-1H-imidazole-2-carboxylic acid [4-(6-amino-pyridin-3-yl)-2-cyclohex-1-enyl-phenyl]-amide, trifluoroacetic acid salt;
5-Cyano-1H-imidazole-2-carboxylic acid (2-cyclohex-1-enyl-4-pyridin-4-yl-phenyl)-amide;
4-Cyano-1H-imidazole-2-carboxylic acid [2-cyclohex-1-enyl-4-(1-oxy-pyridin-3-yl)-phenyl]-amide;
4-Cyano-1H-imidazole-2-carboxylic acid (2-cyclohex-1-enyl-4-pyridin-2-yl-phenyl)-amide;
4-Cyano-1H-imidazole-2-carboxylic acid (2-cyclohex-1-enyl-4-isopropyl-phenyl)-amide;
4-Cyano-1H-imidazole-2-carboxylic acid [2-(4,4-dimethyl-cyclohex-1-enyl)-4-(1-hydroxy-1-methyl-ethyl)-phenyl]-amide;
4-Cyano-1H-imidazole-2-carboxylic acid [2-cyclohex-1-enyl-4-(2-hydroxy-2-methyl-propyl)-phenyl]-amide; and
5-Cyano-1H-imidazole-2-carboxylic acid [2-(4,4-dimethyl-cyclohex-1-enyl)-4-(2-hydroxy-ethyl)-phenyl]-amide.

The invention also relates to methods of inhibiting protein tyrosine kinase activity in a mammal by administration of a therapeutically effective amount of at least one compound of Formula I, II or III. A preferred tyrosine kinase is c-fms.

The invention is considered to include the enantiomeric, diastereomeric and tautomeric forms of all compounds of Formulae I, II and III as well as their racemic mixtures. In addition, some of the compounds represented by Formulae I, II and III may be prodrugs, i.e., derivatives of an acting drug that possess superior delivery capabilities and therapeutic value as compared to the acting drug. Prodrugs are transformed into active drugs by in vivo enzymatic or chemical processes.

1. Definitions

The term "alkyl" refers to both linear and branched chain radicals of up to 12 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "cycloalkyl" refers to a saturated or partially unsaturated ring composed of from 3 to 8 carbon atoms. Alkyl substitutents may optionally be present on the ring. Examples include cyclopropyl, 1,1-dimethyl cyclobutyl, 1,2,3-trimethylcyclopentyl, cyclohexyl and cyclohexenyl and dimethylcyclohexenyl.

The term "heterocyclyl" refers to a nonaromatic (i.e. saturated or partially unsaturated) ring composed of from 3 to 7 carbon atoms and at least one heteroatom selected from N, O or S. Alkyl substituents may optionally be present on the ring. Examples include tetrahydrofuryl, dihydropyranyl, piperidyl, 2,5-dimethypiperidyl, morpholinyl, piperazinyl, thiomorpholinyl, pyrrolidinyl, pyrrolinyl, pyrazolidinyl, pyrazolinyl, imidazolidinyl imidazolinyl and tetrazolyl.

The term "heterocyclylalkyl" refers to a $C_{1-6}$ alkyl group containing a heterocyclyl substituent. Examples include dihydropyranylethyl and 2-morpholinylpropyl.

The term "hydroxyalkyl" refers to at least one hydroxyl group bonded to any carbon atom along an alkyl chain.

The term "aminoalkyl" refers to at least one primary or secondary amino group bonded to any carbon atom along an alkyl chain.

The term "alkoxyalkyl" refers to at least one alkoxy group bonded to any carbon atom along an alkyl chain.

The term "polyalkoxyalkyl" refers to long-chain alkoxy compounds and includes polyethylene glycols of discreet or monodispersed sizes.

The term "thioalkyl" refers to at least one sulfur group bonded to any carbon atom along an alkyl chain. The sulfur group may be at any oxidation state and includes sulfoxides, sulfones and sulfates.

The term "carboxyalkyl" refers to at least one carboxylate group bonded to any carbon atom along an alkyl chain. The term "carboxylate group" includes carboxylic acids and alkyl, cycloalkyl, aryl or aralkyl carboxylate esters.

The term "heteroaromatic" or "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroaralkyl" refers to a $C_{1-6}$ alkyl group having a heteroaryl substituent. Examples include furylethyl and 2-quinolinylpropyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring. Alkyl substituents may optionally be present on the ring. Examples include benzene, biphenyl and napththalene.

The term "aralkyl" refers to a $C_{1-6}$ alkyl group containing an aryl substituent. Examples include benzyl, phenylethyl or 2-naphthylmethyl.

The term "heteroaralkyl" refers to a $C_{1-6}$ alkyl group containing a heteroaryl substituent. Examples include furylmethyl and pyridylpropyl.

The term "aryloxy" refers to an oxygen atom bound to an aryl substituent. Examples include phenoxy and benzyloxy.

The term "arylalkoxy" refers to an alkoxy group bound to an aryl substituent. Examples include phenylmethyl ether.

The term "acyl" refers to the group —C(O)$R_a$, where $R_a$ is alkyl, aryl, aralkyl, heteroaryl and heteroaralkyl. An "acylating agent" adds the —C(O)$R_a$ group to a molecule.

The term "sulfonyl" refers to the group —S(O)$_2R_a$, where $R_a$ is hydrogen, alkyl, cycloalkyl, haloalkyl, aryl, aralkyl, heteroaryl and heteroaralkyl. A "sulfonylating agent" adds the —S(O)$_2R_a$ group to a molecule.

II. Therapeutic Uses

The compounds of Formulae I, II and III represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I, II or III. A preferred tyrosine kinase is c-fms. In one embodiment of inhibiting a protein tyrosine kinase, at least one of the compounds of Formula I, II or III is combined with a known tyrosine kinase inhibitor.

In various embodiments of the invention, the protein tyrosine kinases inhibited by the compounds of Formulae I, II and III are located in cells, in a mammal or in vitro. In the case of mammals, which includes humans, a therapeutically effective amount of a pharmaceutically acceptable form of at least one of the compounds of Formula I, II or III is administered.

The invention further provides methods of treating cancer in mammals, including humans, by administration of a therapeutically effective amount of a pharmaceutically acceptable composition of least one compound of Formula I, II or III. Exemplary cancers include, but are not limited to, breast cancer, colon cancer, stomach cancer, hairy cell leukemia and non-small lung carcinoma. In one embodiment of the invention, an effective amount of at least one compound of Formula I, II or III is administered in combination with an effective amount of a chemotherapeutic agent.

The invention also provides methods of treating cardiovascular and inflammatory diseases in mammals, including humans, by administration of a therapeutically effective amount of a pharmaceutically acceptable form of at least one of the compounds of Formula I, II or III. Example of diseases that may be effectively treated include glomerulonephritis, rheumatoid arthritis, psoriasis, diabetes, tumor related angiogenesis, restenosis, schizophrenia and Alzheimer's dementia.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

The compounds of Formulae I, II and III may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formulae I, II and III include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamine salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

III. Methods of Preparation

The compounds of Formulae I, II and III may be prepared by either solid phase support methodology or by solution-phase synthesis. Exemplary synthetic routes for generating amides of the invention are described below.

EXAMPLE 1

General Procedure for Preparation of Amides

5-Nitro-furan-2-carboxylic acid phenylamides

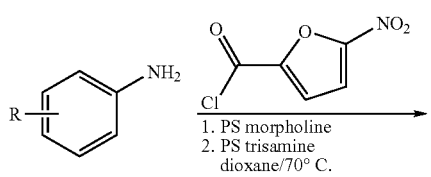

-continued

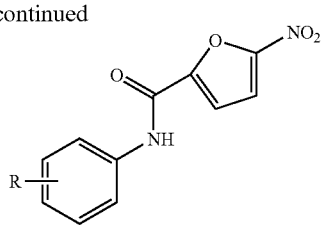

A solution of aniline (10 mg, 0.069 mmol) in dioxane (0.5 mL) was treated with polystyrene ("PS") morpholine resin (Aldrich) (50 mg, 0.14 mmol), followed by the addition of a solution of 5-nitro-furan-2-carbonyl chloride (Lancaster) (15 mg, 0.086 mmol) in dioxane (0.5 mL). The reaction was heated to 70° C. and agitated for 2 h. The reaction was treated with PS trisamine (Aldrich) (25 mg, 0.12 mmol) and heated to 70° C. for an additional 2 h. Filtration gave the desired product in >80% yield.

EXAMPLE 2

Procedure 2 for Preparation of Amides

Isoxazole-5-carboxylic acid (2-piperidin-1-yl-phenyl)-amide

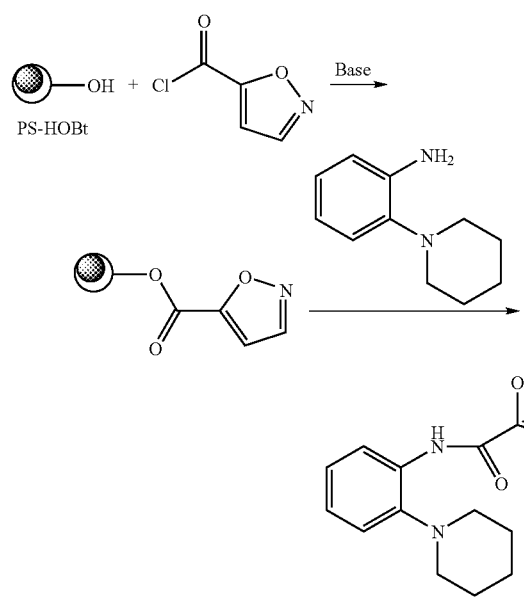

To PS-HOBt resin (0.1 mmol) was added anhydrous dichloromethane ("DCM") (1 mL) followed by pyridine (0.5 mmol) and isoxazole-5-carbonyl chloride (Lancaster) (0.3 mmol). The mixture was shaken at room temperature for 3 h and was then filtered. The resin was washed successively with tetrahydrofuran ("THF") (3×) and DCM (3×) and dried in vacuo. To this acylated resin was added a solution of 2-piperidinoaniline (Lancaster) (0.05 mmol, 0.5 eq) in anhydrous THF (1 mL) and the mixture was shaken at room temperature for 16 h. The mixtue was then filtered and the resin washed with THF and DCM as described above. The combined filtrate and washings were concentrated under reduced pressure to yield the product. Yield: 100%. MS: 272 (M+1). LC/MS purity: 100%. $^1$HNMR (CDCl$_3$, 300 MHz): δ 8.2 (d, 1H), 7.85 (t, 2H), 7.55 (m, 1H), 7.4 (m, 2H), 3.8-3.2 (bm, 4H), 2.7-1.9 (bm, 4H).

EXAMPLE 2-A

5-Nitro-furan-2-carboxylic acid (2-piperidin-1-yl-phenyl)-amide

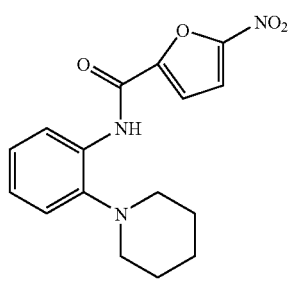

The compound was prepared according to the procedure described in Example 2 from 5-nitro-furan-2-carbonyl chloride and 2-piperidinoaniline. Yield: 100%. MS: 316 (M+1). LC/MS purity: 100%. $^1$HNMR (CDCl$_3$, 300 MHz): δ 8.2 (d, 1H), 7.85 (d, 1H), 7.55 (m, 1H), 7.4 (m, 3H), 3.8-3.2 (bm, 4H), 2.7-1.9 (bm, 6H).

EXAMPLE 3

Procedure 3 for Preparation of Amides

5-Nitro-thiophene-2-carboxylic acid (2-piperidin-1-yl-phenyl))-amide

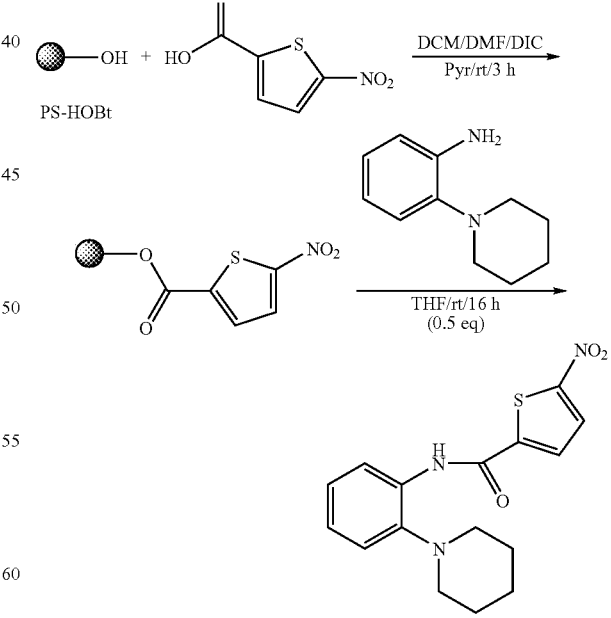

To PS-HOBt resin (0.15 mmol) was added 2 mL of a solution of pyridine (0.09 mmol) in DCM and 0.6 mL of a solution of the carboxylic acid (0.23 mmol) in N,N-dimethyl formamide ("DMF"). The mixture was shaken at room temperature for 5 min before the addition of 0.4 mL of a solution of 1,3-diisopropylcarbodiimide ("DIC") (0.66 mmol) in DCM. The mixture was shaken at room temperature for 3 h and filtered. The resin was washed with DMF (3×), THF (3×) and DCM (3×) and dried in vacuo. To this acyl resin was added a solution of 2-piperidinoaniline (0.075 mmol; 0.5 eq) in anhydrous THF (1 mL) and the mixture was shaken at room temperature for 16 h. The reaction was then filtered and the resin washed with THF and DCM. The combined filtrate and washings were concentrated in vacuo to yield the product. MS: 332 (M+1). LC/MS: 100% purity. $^1$H NMR (CDCl$_3$, 300 MHz): δ 7.95 (d, 2H), 7.5 (m, 2H), 7.2 (m, 2H), 2.85 (m, 4H), 1.8-1.6 (bm, 4H), 1.5 (bm, 2H).

EXAMPLE 4

Procedure 4 for Preparation of Amides

5-Bromo-furan-2-carboxylic acid (2-piperidin-1-yl-phenyl)-amide

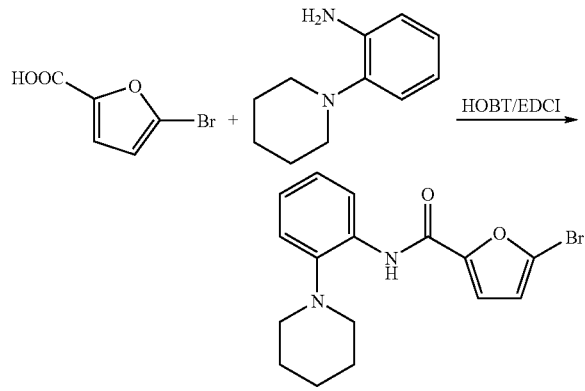

A solution of 5-bromofuroic acid (Aldrich) (1.0 mmol), 2-piperdinoaniline (1.0 mmol), 1-hydroxybenzotriazole hydrate ("HOBT") (1.2 mmol), and triethylamine ("Et$_3$N") (2 mmol) in DCM (10 mL) was stirred for 10 min at room temperature. 1-(3-Dimethylaminopropyl)-3-ethylcarbodiimide hydrochloride ("EDCI") (1.2 mmol) was then added and the resulting orange solution was stirred overnight. The reaction mixture was treated with saturated sodium bicarbonate ("NaHCO$_3$") solution (10 mL) and extracted with DCM. The combined organic layers were dried over MgSO$_4$, and concentrated under reduced pressure to afford the crude product as an orange solid. Purification by silica gel chromatography afforded the pure yellow product in 85% yield. MS: 349 (M+1). $^1$H NMR (CDCl$_3$, 300 MHz): δ 9.75 (br s, 1H), 8.45 (d, 1H), 7.22-7.05 (m, 4H), 6.50 (d, 1H), 3.00-2.80 (m, 4H), 1.95-1.80 (m, 4H), 1.75-1.60 (m, 2H).

EXAMPLE 4-A 5-(2-Piperidin-1-yl-phenylcarbamoyl)-furan-2-carboxylic acid

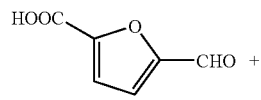

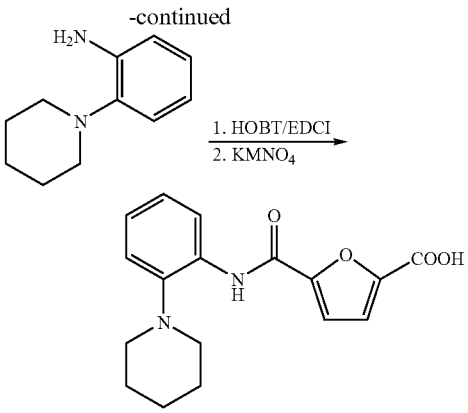

A solution of 5-formyl-2-furancarboxylic acid (TCI) (1.0 mmol), 2-piperidinoaniline (1.0 mmol), HOBT (1.2 mmol), and Et$_3$N (2 mmol) in DCM (10 mL) was stirred for 10 min at room temperature. EDCI (1.2 mmol) was then added and the resulting orange solution was stirred overnight. The reaction mixture was treated with saturated NaHCO$_3$ solution (10 mL) and extracted with DCM. The combined organic layers were dried over MgSO$_4$, and concentrated under reduced pressure to afford the crude product as an orange solid. Purification by silica gel chromatography afforded the amidoaldehyde product in 80% yield. The aldehyde product (1 mmol) was dissolved in H$_2$O/dimethoxyethane ("DME") (2:1, 5 mL) containing sodium carbonate ("Na$_2$CO$_3$") (2 mol). In a separate flask, potassium permanganate ("KMnO$_4$") (1.3 mmol) was dissolved in H$_2$O (5 mL) and was slowly added to the reaction flask at 45° C. The reaction was stirred overnight at room temperature, filtered through a plug of celite, and then acidified to a pH of 3 to 4 using a hydrochloric acid ("HCl") solution (1 N). The product, which precipitated out as a white solid, was filtered, washed with H$_2$O and dried under high vacuum to afford pure product. MS: 315 (M+1). $^1$H NMR (DMSO-d$_6$, 300 MHz): δ 13.60 (br s, 1H), 9.90 (s, 1H), 8.25 (dd, 1H), 7.36 (dd, 2H), 7.35-7.25 (m, 1H), 7.20-7.10 (m, 2H), 2.85-2.65 (m, 4H), 1.85-1.65 (m, 4H), 1.65-1.45 (m, 2H).

EXAMPLE 5

Procedure for Preparation of Reduced Amides 5-(Nitro-furan-2-ylmethyl)-(2-piperidin-1-yl-phenyl)-amine

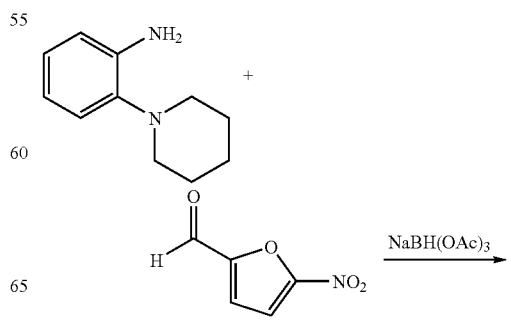

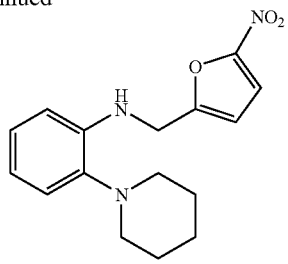

A solution of 2-piperidinoaniline (1 mmol), 5-nitro-furan-2-carbaldehyde (1.1 mmol) and sodium triacetoxyborohydride ("NaBH(OAc)₃") (2 mmol) in anhydrous DCM (10 mL) was stirred 16 h at room temperature. The mixture was then washed successively with water, dilute aqueous sodium hydroxide ("NaOH"), water and brine before being dried over MgSO$_4$, filtered and concentrated under reduced pressure. Purification of the residual oil by flash silica gel chromatography yielded the product. MS: 301 (M+1). LC/MS purity: 100%. $^1$H NMR (CDCl$_3$, 300 MHz): δ 7.25 (d, 1H), 7.15-6.95 (m, 2H), 6.75 (t, 1H), 6.55 (d, 1H), 6.4 (d, 1H), 5.4 (bs, 1H), 4.45 (s, 2H), 2.8 (bm, 4H), 1.8-1.5 (bm, 6H).

EXAMPLE 6

Preparation of 5-Cyano-furan-2-carboxylic acid [5-hydroxymethyl-2-(4-methyl-piperidin-1-yl)-phenyl]-amide A. 2-Cyano-5-furancarboxylic acid

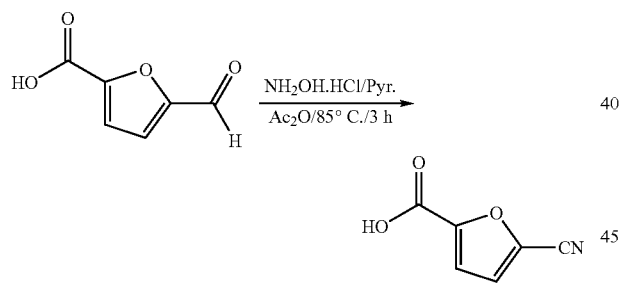

To a solution of 2-formyl-5-furancarboxylic acid (0.28 g, 2.0 mol) in pyridine (5.0 mL) was added hydroxylamine hydrochloride ("NH$_2$OH.HCl") (0.27 g, 4.0 mol). The mixture was heated to 85° C. before the addition of acetic anhydride (4.0 ml). The reaction mixture was stirred at 85° C. for 3 h, cooled to 60° C. and poured into water (25 mL). The mixture was cooled to room temperature and stirred overnight (the pH of the solution was measured to be 5-6). The impurities were extracted with a solution of 4/1 DCM/isopropanol (3×30 mL). The aqueous layer was then basified with NaOH solution (2 N) to a pH of about 9, and the pyridine was extracted with a solution of 4/1 DCM/isopropanol (3×30 mL). The aqueous solution was then acidified to a pH of about 2 and the product was extracted with a solution of 3/1 DCM/isopropanol (3×50 mL). The combined organic extracts were dried over MgSO$_4$, and the solvent was evaporated to afforded the pure product as a light brown solid in 90% yield. $^1$H NMR (DMSO-d$_6$): δ 13.80 (bs, 1H), 7.75 (d, 1H), 7.40 (d, 1H). IR (neat): (cm$^{-1}$) 3200, 2250, 1053, 1025, 1006.

B. 4-(4-Methyl-piperidin-1-yl)-3-nitro-phenyl]-methanol

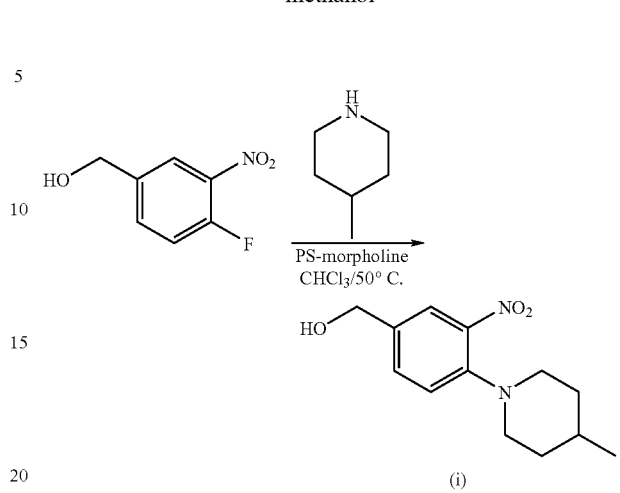

A stirred suspension of (4-fluoro-3-nitro-phenyl)-methanol (171 mg, 1 mmol), 4-methyl piperidine (95 mg, 0.96 mmol) PS morpholine (400 mg, 1 mmol), and chloroform (3 mL) was heated at 50° C. for 2 hrs. The reaction was evaporated onto celite and purified by flash chromatography to give [4-(4-methyl-piperidin-1-yl)-3-nitro-phenyl]-methanol (i). $^1$H NMR (CDCl$_3$, 300 MHz): δ 7.8 (s, 1H), 7.4 (d, 1H), 7.1 (d, 1H), 4.6 (s, 2H), 3.2 (d, 2H), 2.8 (dd, 2H), 1.8-1.3 (m, 5H), 1.0 (d, 3H).

C. 5-Cyano-furan-2-carboxylic acid [5-hydroxymethyl-2-(4-methyl-piperidin-1-yl)-phenyl]-amide

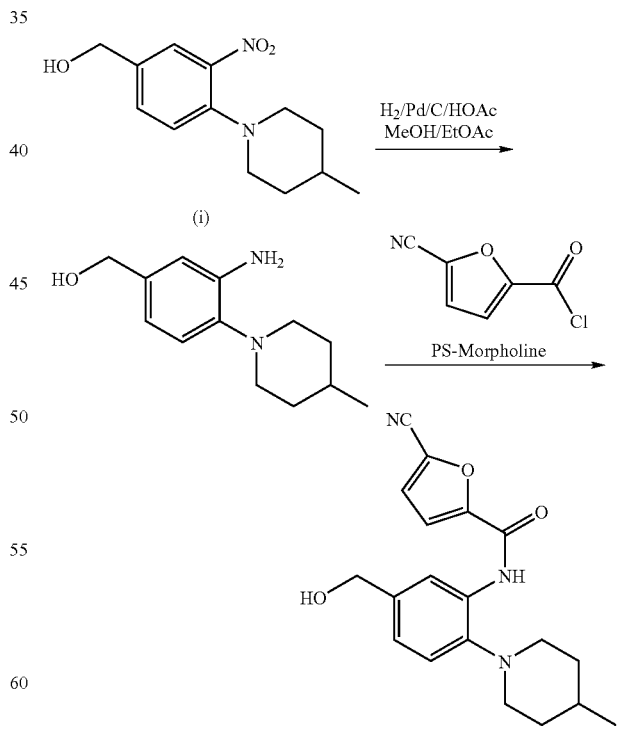

A suspension of 5% Pd/C (5.0 mg, 2.3×10$^{-3}$ mmol), [4-(4-methyl-piperidin-1-yl)-3-nitro-phenyl]-methanol (i) (95 mg, 0.38 mmol), acetic acid ("HOAc") (23 mg, 0.38 mmol), methanol (1 mL) and ethyl acetate (4 mL) was stirred in an atmosphere of hydrogen for 3 h. The reaction was filtered, concentrated in vacuo and the resulting [3-amino-4-(4-methyl-piperidin-1-yl)-phenyl]-methanol was used in the next step without further purification. A suspension of [3-amino-4-(4-methyl-piperidin-1-yl)-phenyl]-methanol, 5-cyano-2-furoyl chloride (64 mg, 0.44 mmol), PS morpholine (600 mg, 1.50 mmol), and DCM (10 mL) was stirred at room temperature for 30 min. The reaction was evaporated onto celite, and purified by column chromatography to give 5-cyano-furan-2-carboxylic acid [5-hydroxymethyl-2-(4-methyl-piperidin-1-yl)-phenyl]-amide. MS: 340 (M+1), $^1$H NMR (CDCl$_3$, 300 MHz): δ 9.9 (s br, 1H), 8.4 (s, 1H), 7.3 (s, 1H), 7.25-7.1 (m, 3H), 4.7 (s, 2H), 3.0 (m, 2H), 2.8 (m, 2H), 1.9, (d, 2H), 1.8-1.4 (m, 3H), 1.1 (d, 3H).

EXAMPLE 7

Procedure for Preparation of Biarylamides

5-Phenyl-furan-2-carboxylic acid (2-piperidin-1-yl-phenyl)-amide

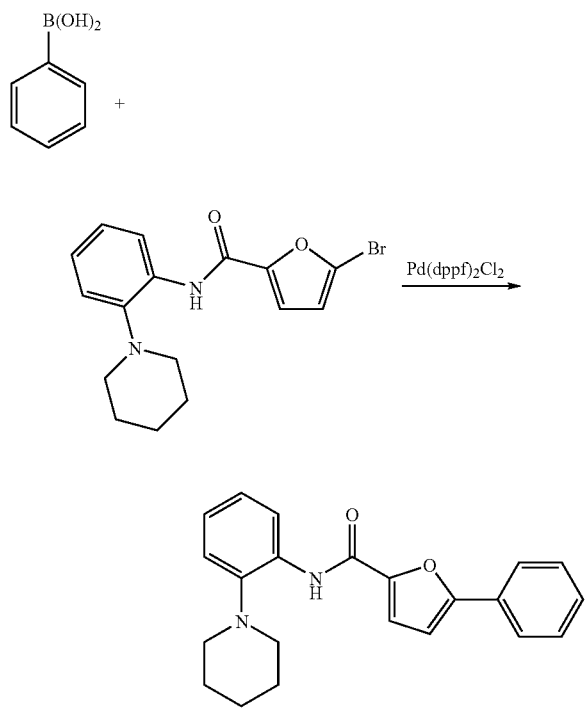

5-Bromo-furan-2-carboxylic acid (2-piperidin-1-yl-phenyl)-amide (1.0 mmol), phenylboronic acid (1.2 mmol), 1,1'-bis(diphenylphosphino)ferrocene]dichloropalladium (II) ["Pd(dppf)$_2$Cl$_2$"] (Aldrich) (0.05 mmol) and Na$_2$CO$_3$ (3.0 mmol) were dissolved in a solution of THF/H$_2$O (4:1, 5 mL; saturated with argon) and heated to 80° C. for 5 h. After cooling to room temperature, the mixture was concentrated under reduced pressure and the resulting residue was purified by silica gel chromatography to afford the pure product. Yield: 75%. MS: 347 (M+1). $^1$H NMR (CDCl$_3$, 300 MHz): δ 9.90 (br s, 1H), 8.50 (d, 1H), 7.82 (d, 2H), 7.50-7.28 (m, 4H), 7.24-7.05 (m, 3H), 6.82 (d, 1H), 3.00-2.80 (m, 4H), 1.95-1.80 (m, 4H), 1.75-1.60 (m, 2H).

EXAMPLE 8

Procedure for Extension of Aromatic Rings Through Amination

5-Phenylamino-furan-2-carboxylic acid (2-piperidin-1-yl-phenyl)-amide

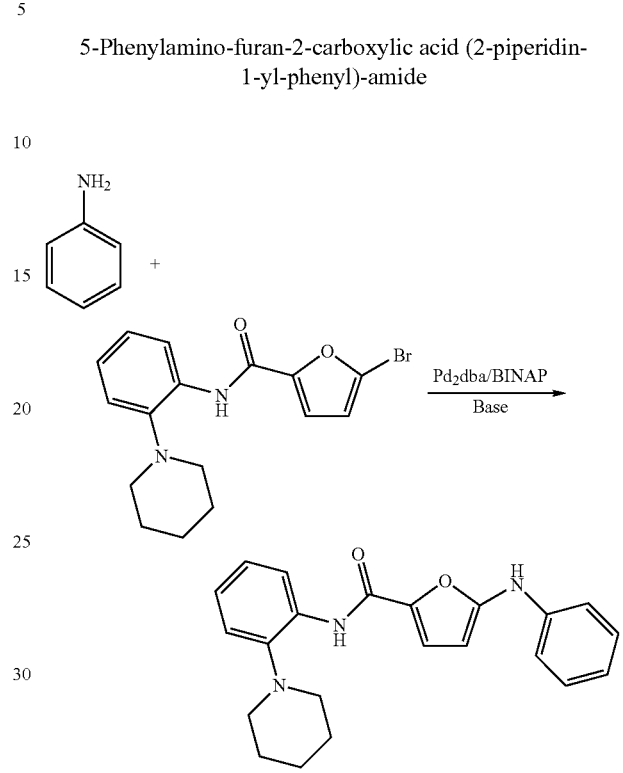

To a solution of 5-bromo-furan-2-carboxylic acid (2-piperidin-1-yl-phenyl)-amide (1.0 mmol) in toluene (7.5 mL) was added aniline (1.3 mmol), tris(dibenzylidineacetone)dipalladium(0) ("Pd$_2$ dba") (Aldrich) (0.05 mmol), 2,2'-bis(diphenylphosphino)-1,1'-binaphthyl ("BINAP") (0.1 mmol), and potassium tert-butoxide ("t-BuOK") (1.5 mmol), and the resulting mixture was refluxed overnight. The reaction was then cooled to room temperature, passed through a plug of silica and concentrated. Purification of the dark brown residue by HPLC afforded the product. Yield: 40%. MS: 362 (M+1).

EXAMPLE 9

Procedure 1 for Preparation of the Compounds of Formula III

4-Oxo-6-piperidin-1-yl-4,5-dihydro-furo[2,3-c]quinoline-2-carbonitrile

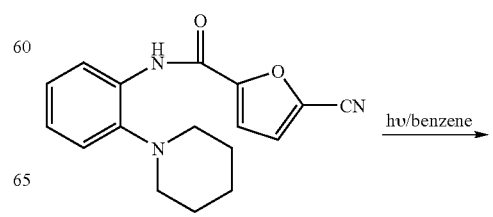

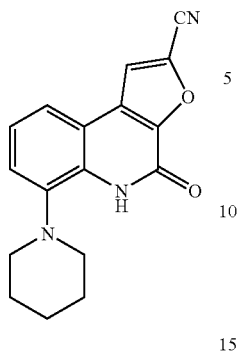

5-Cyano-furan-2-carboxylic acid (2-piperidin-1-yl-phenyl)-amide (200 mg) is dissolved in a mixture of benzene (180 mL) and ethanol (20 mL). The solution is irradiated with a 100 W high pressure Hg Lamp at room temperature for 10 h, according to the method described by Kanoka and Itoh [*Synthesis*, 36 (1972)]. The solvent is removed in vacuo and the residue is purified by preparative thin layer chromatography ("TLC") (silica gel) to yield the pure product.

EXAMPLE 10

Procedure 2 for Preparation of the Compounds of Formula III

4-Oxo-6-piperidin-1-yl-4,5-dihydro-furo[2,3-c]quinoline-2-carbonitrile

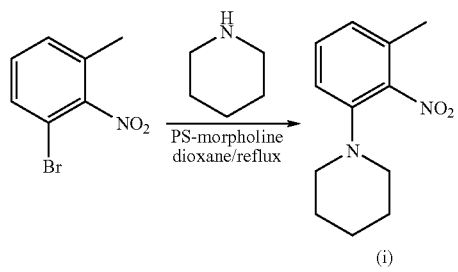

A solution of 2-nitro-3-bromotoluene (1.8 g, 8.3 mmol), piperidine (10 mL, 101 mmol), and dioxane (85 mL) was heated to reflux for 56 h. The reaction was filtered, concentrated and evaporated onto Celite. Chromatography on silica gel gave 1-(3-methyl-2-nitro-phenyl)-piperidine (i).

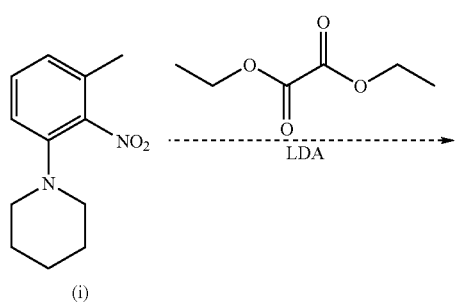

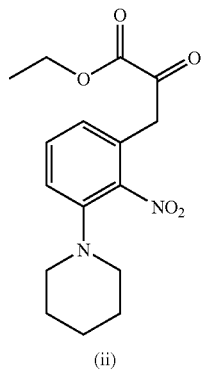

A solution of 1-(3-methyl-2-nitro-phenyl)-piperidine (i) in THF is treated with lithium diisopropylamide ("LDA") (1 eq), followed by diethyl oxalate (1.05 eq), at 0° C. The reaction is allowed to warm to room temperature over 90 min. The reaction is diluted with water and ether, partitioned, and the aqueous layer is washed with ether. The combined organic layers are dried over MgSO$_4$, filtered and concentrated. Chromatography gives 3-(2-nitro-3-piperidin-1-yl-phenyl)-2-oxo-propionic acid ethyl ester (ii).

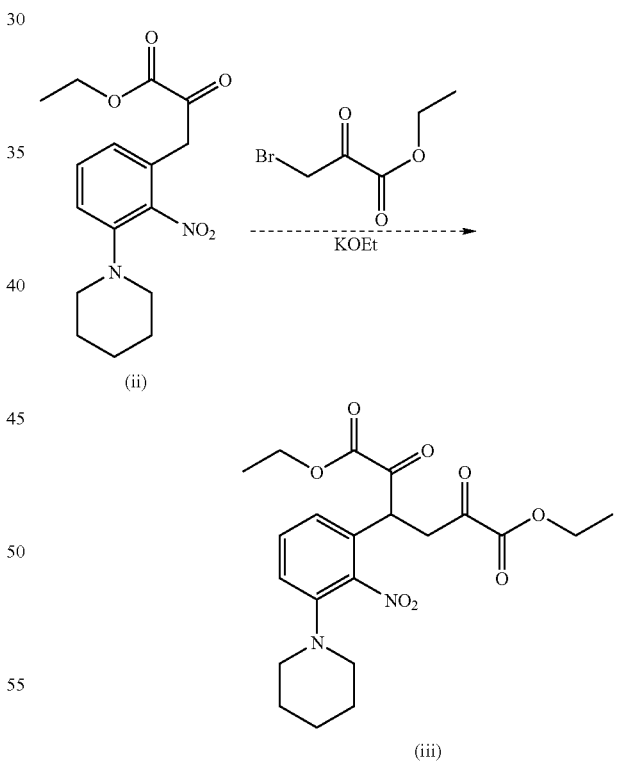

A solution of 3-(2-nitro-3-piperidin-1-yl-phenyl)-2-oxo-propionic acid ethyl ester (ii) in THF is treated with potassium ethoxide ("KOEt") (1 eq), followed by bromoethyl pyruvate (1.05 eq), at 0° C. The reaction is allowed to warm to room temperature over 90 min. The reaction is diluted with water and ether, partitioned, and the aqueous layer is washed with ether. The combined organic layers are dried over MgSO$_4$, filtered and concentrated. Chromatography gives 3-(2-nitro-3-piperidin-1-yl-phenyl)-2,5-dioxo-hexanedioic acid diethyl ester (iii).

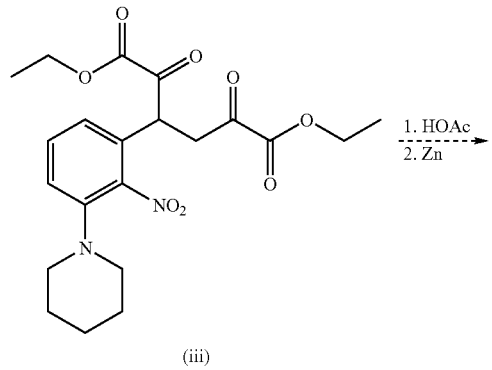

(iii)

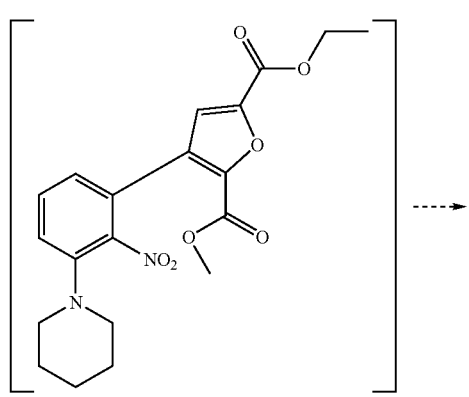

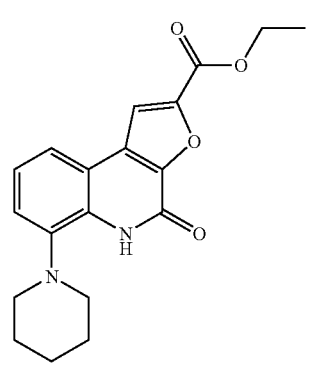

(iv)

A solution of 3-(2-nitro-3-piperidin-1-yl-phenyl)-2,5-dioxo-hexanedioic acid diethyl ester (iii) in THF is treated with acetic acid ("HOAc") and is stirred at room temperature for 4 h. The reaction is treated with zinc dust (10 eq) and is stirred for an additional 2 h. The reaction is diluted with DCM, half saturated brine, and partitioned. The organic layer is washed with saturated aqueous NaHCO$_3$, dried over MgSO$_4$, filtered and concentrated. Chromatography gives 4-oxo-6-piperidin-1-yl-4,5-dihydro-furo[2,3-c]quinoline-2-carboxylic acid ethyl ester (iv).

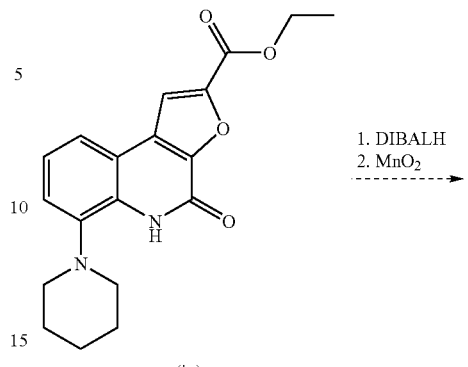

(iv)

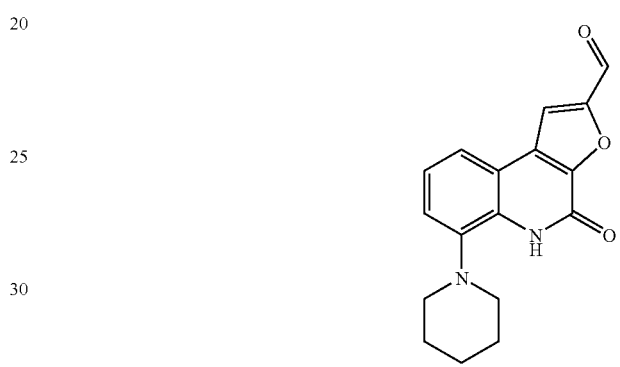

(v)

A solution of 4-oxo-6-piperidin-1-yl-4,5-dihydro-furo[2,3-c]quinoline-2-carboxylic acid ethyl ester (iv) in DCM at 0° C. is treated with diisobutylaluminum hydride ("DIBAL-H") and is allowed to warm to room temperature. The reaction is quenched with a saturated solution of sodium potassium tartrate and partitioned. The organic layer is dried over MgSO$_4$, filtered and treated with manganese dioxide ("MnO$_2$"). After stirring for 16 h at room temperature, the reaction is filtered and is concentrated to give 4-oxo-6-piperidin-1-yl-4,5-dihydro-furo[2,3-c]quinoline-2-carbaldehyde (v).

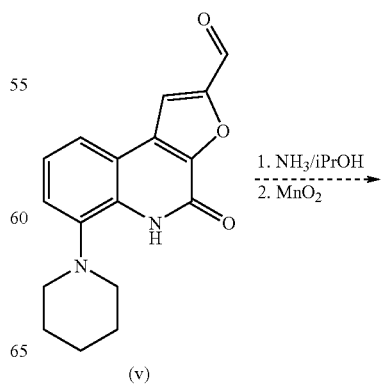

(v)

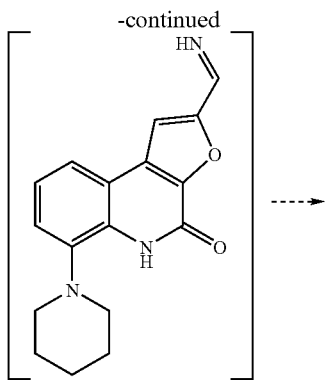

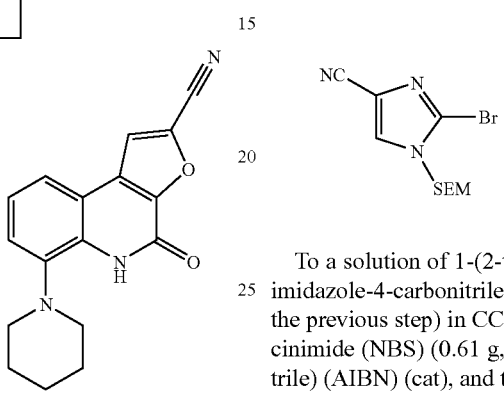

A solution of 4-oxo-6-piperidin-1-yl-4,5-dihydro-furo[2,3-c]quinoline-2-carbaldehyde (v) in isopropanol ("iPrOH") is treated with ammonia gas at room temperature. After 90 min, the reaction is treated with MnO$_2$ and stirred for an additional 16 h. The reaction is filtered and evaporated onto celite. Chromatography on silica gel affords 4-oxo-6-piperidin-1-yl-4,5-dihydro-furo[2,3-c]quinoline-2-carbonitrile.

EXAMPLE 11

4-Cyano-1H-imidazole-2-carboxylic acid (4-bromo-2-cyclohex-1-enyl-phenyl)-amide

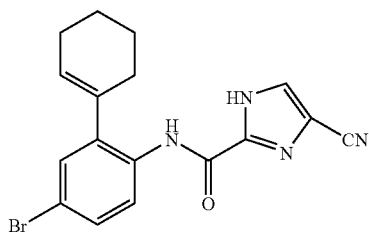

a) 1-(2-Trimethylsilanyl-ethoxymethyl)-1H-imidazole-4-carbonitrile

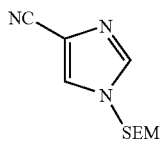

A flask charged with imidazole-4-carbonitrile (0.50 g, 5.2 mmol) (Synthesis, 677, 2003), 2-(trimethylsilyl)ethoxymethyl chloride (SEMCl) (0.95 mL, 5.3 mmol), K$_2$CO$_3$ (1.40 g, 10.4 mmol), and acetone (5 mL) was stirred for 10 h at RT. The mixture was diluted with EtOAc (20 mL) and washed with water (20 mL) and brine (20 mL) and the organic layer dried over MgSO$_4$. The crude product was eluted from a 20-g SPE cartridge (silica) with 30% EtOAc/hexane to give 0.80 g (70%) of the title compound as a colorless oil. Mass spectrum (CI (CH$_4$), m/z) Calcd. for C$_{10}$H$_{17}$N$_3$OSi, 224.1 (M+H), found 224.1.

b) 2-Bromo-1-(2-trimethylsilanyl-ethoxymethyl)-1H-imidazole-4-carbonitrile

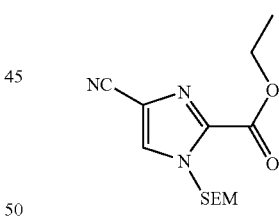

To a solution of 1-(2-trimethylsilanyl-ethoxymethyl)-1H-imidazole-4-carbonitrile (0.70 g, 3.1 mmol) (as prepared in the previous step) in CCl$_4$ (10 mL) was added N-bromosuccinimide (NBS) (0.61 g, 3.4 mmol) and azobis(isobutyronitrile) (AIBN) (cat), and the mixture was heated at 60° C. for 4 h. The reaction was diluted with EtOAc (30 mL), washed with NaHCO$_3$ (2×30 mL), brine (30 mL), the organic layer was dried over Na$_2$SO$_4$ and then concentrated. The title compound was eluted from a 20-g SPE cartridge (silica) with 30% EtOAc/hexane to give 0.73 g (77%) of a yellow solid. Mass spectrum (CI (CH$_4$), m/z) Calcd. for C$_{10}$H$_{16}$BrN$_3$OSi, 302.0/304.0 (M+H), found 302.1/304.1.

c) 4-Cyano-1-(2-trimethylsilanyl-ethoxymethyl)-1H-imidazole-2-carboxylic acid ethyl ester To a solution of 2-bromo-1-(2-trimethylsilanyl-ethoxymethyl)-1H-imidazole-4-carbonitrile (0.55 g, 1.8 mmol) (as prepared in the previous step) in tetrahydrofuran (THF) (6 mL) at −40° C. was added drop wise a solution of 2 M i-PrMgCl in THF (1 mL). The reaction was allowed to stir for 10 min at −40° C. and then cooled to −78° C., and ethyl cyanoformate (0.30 g, 3.0 mmol) was added. The reaction allowed to attain RT and stirred for 1 h. The reaction was quenched with satd aq NH$_4$Cl, diluted with EtOAc (20 mL), washed with brine (2×20 mL). The organic layer was dried over Na$_2$SO$_4$ and then concentrated. The title compound was eluted from a 20-g SPE cartridge (silica) with 30% EtOAc/hexane to give 0.40 g (74%) of a colorless oil. Mass spectrum (ESI, m/z): Calcd. for C$_{13}$H$_{21}$N$_3$O$_3$Si, 296.1 (M+H), found 296.1.

d) 4-Cyano-1-(2-trimethylsilanyl-ethoxymethyl)-1H-imidazole-2-carboxylate potassium salt

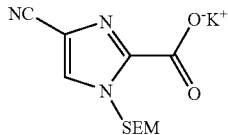

To a solution of 4-cyano-1-(2-trimethylsilanyl-ethoxymethyl)-1H-imidazole-2-carboxylic acid ethyl ester (0.40 g, 1.3 mmol) (as prepared in the previous step) in ethanol (3 mL) was added a solution of 6 M KOH (0.20 mL) and the reaction was stirred for 10 min and then concentrated to give 0.40 g (100%) of the title compound as a yellow solid. $^1$H-NMR (CD$_3$OD; 400 MHz) δ 7.98 (s, 1H), 5.92 (s, 2H), 3.62 (m, 2H), 0.94 (m, 2H), 0.00 (s, 9H). Mass spectrum (ESI-neg, m/z): Calcd. for $C_{11}H_{16}KN_3O_3Si$, 266.1 (M-K), found 266.0.

e) 4-Bromo-2-cyclohex-1-enyl-phenylamine

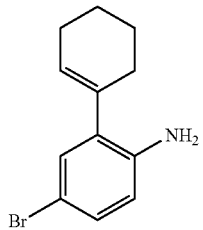

To a mixture of 4-bromo-2-iodo-phenylamine (2.00 g, 6.71 mmol), 2-cyclohex-1-enyl-4,4,5,5-tetramethyl-[1,3,2]dioxaborolane (1.40 g, 6.71 mmol) and Pd(PPh$_3$)$_4$ (388 mg, 0.336 mmol) in 40 mL of 1,4-dioxane was added 2.0 M aq Na$_2$CO$_3$ solution (26.8 mL, 53.7 mmol). After stirring at 80° C. for 5 h under Ar, the reaction was cooled to RT. The mixture was treated with EtOAc (100 mL), washed with H$_2$O (3×30 mL) and brine (20 mL). The organic layer was dried (Na$_2$SO$_4$) and concentrated in vacuo. The residue was purified by flash chromatography on silica gel (10-20% EtOAc/hexane) to give 1.47 g (87%) of the title compound as a light brown oil. Mass spectrum (ESI, m/z): Calcd. for $C_{12}H_{14}BrN$, 252.0 (M+H), found 252.0.

f) 4-Cyano-1-(2-trimethylsilanyl-ethoxymethyl)-1H-imidazole-2-carboxylic acid (4-bromo-2-cyclohex-1-enyl-phenyl)-amide

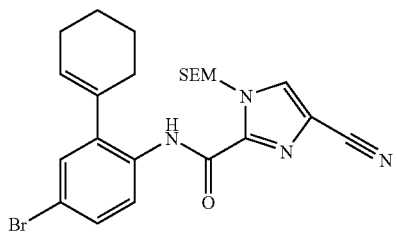

To a mixture of 4-bromo-2-cyclohex-1-enyl-phenylamine (as prepared in the previous step, 1.23 g, 4.88 mmol), potassium 4-cyano-1-(2-trimethylsilanyl-ethoxymethyl)-1H-imidazole-2-carboxylate (as prepared in Example 11, step (d), 1.49 g, 4.88 mmol) and bromotripyrrolidinophosphonium hexafluorophosphate (PyBroP) (2.27 g, 4.88 mmol) in 25 mL of N,N-dimethylformamide (DMF) was added N,N-diisopropylethylamine (DIEA) (2.55 mL, 14.6 mmol). After stirring at RT for 16 h, the mixture was treated with 100 mL of EtOAc and washed with H$_2$O (2×30 mL), brine (30 mL) and dried (Na$_2$SO$_4$). The organic solvent was evaporated and the residue was purified by flash chromatography on silica gel (5-10% EtOAc/hexane) to give 2.21 g (90%) of the title compound as a white solid. $^1$H-NMR (CDCl$_3$; 400 MHz): δ 9.70 (s, 1H), 8.26 (d, 1H, J=8.6 Hz), 7.78 (s, 1H), 7.36 (dd, 1H, J=8.6, 2.3 Hz), 7.31 (d, 1H, J=2.3 Hz), 5.94 (s, 2H), 5.86 (m, 1H), 3.66 (t, 2H, J=8.3 Hz), 2.19-2.33 (m, 4H), 1.75-1.88 (m, 4H), 0.97 (t, 2H, J=8.3 Hz), 0.00 (s, 9H).

g) 4-Cyano-1H-imidazole-2-carboxylic acid (4-bromo-2-cyclohex-1-enyl-phenyl)-amide To a solution of 4-cyano-1-(2-trimethylsilanyl-ethoxymethyl)-1H-imidazole-2-carboxylic acid (4-bromo-2-cyclohex-1-enyl-phenyl)-amide (as prepared in the previous step, 1.20 mg, 2.39 mmol) in 10 mL of DCM (CH$_2$Cl$_2$) was added 0.30 mL of EtOH followed by 5.0 mL of trifluoroacetic acid (TFA). After stirring at RT for 3 h, the mixture was treated with 20 mL of n-propanol and concentrated in vacuo. The residue was triturated with DCM to afford 853 mg (96%) of the title compound as a white solid. $^1$H-NMR (DMSO-d$_6$; 400 MHz): δ 9.80 (s, 1H), 8.30 (s, 1H), 7.94 (d, 1H, J=8.6 Hz), 7.50 (dd, 1H, J=8.6, 2.3 Hz), 7.39 (d, 1H, J=2.3 Hz), 5.80 (m, 1H), 2.12-2.25 (m, 4H), 1.61-1.77 (m, 4H). Mass spectrum (ESI, m/z): Calcd. for $C_{17}H_{15}BrN_4O$, 371.0 (M+H), found 371.0.

EXAMPLE 12

4-Cyano-1H-imidazole-2-carboxylic acid [2-cyclohex-1-enyl-4-(1-hydroxy-1-methyl-ethyl)-phenyl]-amide

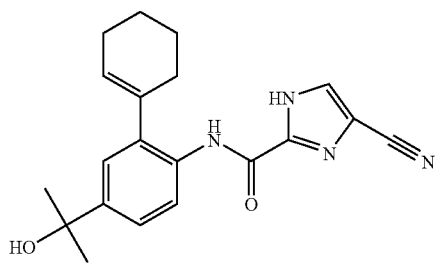

To a solution of 4-cyano-1H-imidazole-2-carboxylic acid (4-bromo-2-cyclohex-1-enyl-phenyl)-amide (as prepared in Example 11, step (g), 50.0 mg, 0.135 mmol) in 2 mL of THF at −78° C. under Ar was added isopropylmagnesium chloride (71 μL, 0.14 mmol, 2.0 M). The resulting mixture was warmed to RT and stirred for 15 min, cooled to −78° C. again. To the mixture was added tert-butyllithium (240 μL, 0.405 mmol, 1.7 M) and the resulting mixture was stirred at −78° C. for 5 min. Acetone (0.40 mL, 0.68 mmol) was then added, and the reaction was warmed to RT and stirred for 1 h under Ar. The mixture was treated with 1 mL of saturated NH$_4$Cl followed by 40 mL of EtOAc and washed with H$_2$O (10 mL), brine (5 mL) and dried (Na$_2$SO$_4$). Removal of the solvent under reduced pressure followed by flash chromatography of the residue on silica gel (1-2% MeOH/DCM) gave 32.1 mg (68%) of the title compound as a white solid. ¹H-NMR (CDCl₃; 400 MHz): δ 11.88 (s, 1H), 9.58 (s, 1H), 8.29 (d, 1H, J=8.6 Hz), 7.74 (s, 1H), 7.42 (dd, 1H, J=8.6, 2.2 Hz), 7.35 (d, 1H, J=2.2 Hz), 5.87 (m, 1H), 2.23-2.34 (m, 4H), 1.73-1.90 (m, 4H), 1.79 (s, 1H, OH), 1.61 (s, 6H). Mass spectrum (ESI, m/z): Calcd. for C₂₀H₂₂N₄O₂, 351.2 (M+H), found 351.0.

EXAMPLE 13

4-Cyano-1H-imidazole-2-carboxylic acid [2-cyclohex-1-enyl-4-(1-methoxy-1-methyl-ethyl)-phenyl]-amide

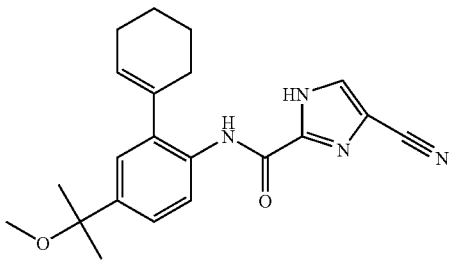

To a solution of 4-cyano-1H-imidazole-2-carboxylic acid [2-cyclohex-1-enyl-4-(1-hydroxy-1-methyl-ethyl)-phenyl]-amide (as prepared in example 12, 18.0 mg, 0.0514 mmol) in 1 mL of DCM was added conc H₂SO₄ (50 μL) followed by 50 μL of MeOH. The resulting mixture was stirred at RT for 0.5 h and then treated with 10 mL of saturated NaHCO₃ aqueous solution. The mixture was extracted with EtOAc (2×20 mL). The combined organic layers were washed with H₂O (10 mL), brine (10 mL) and dried (Na₂SO₄). Removal of the solvent under reduced pressure followed by flash chromatography of the residue on silica gel (1% MeOH/DCM) gave 8.2 mg (44%) of the title compound as a white solid. ¹H-NMR (CDCl₃; 400 MHz): δ 12.31 (s, 1H), 9.65 (s, 1H), 8.30 (d, 1H, J=8.6 Hz), 7.76 (s, 1H), 7.35 (dd, 1H, J=8.6, 2.3 Hz), 7.25 (d, 1H, J=2.3 Hz), 5.88 (m, 1H), 3.11 (s, 3H), 2.23-2.37 (m, 4H), 1.75-1.90 (m, 4H), 1.55 (s, 6H).

EXAMPLE 14

4-Cyano-1H-imidazole-2-carboxylic acid [4-(1-amino-1-methyl-ethyl)-2-cyclohex-1-enyl-phenyl]-amide, acetic acid salt

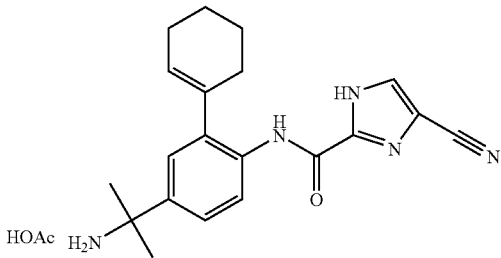

a) 4-Cyano-1H-imidazole-2-carboxylic acid [4-(1-azido-1-methyl-ethyl)-2-cyclohex-1-enyl-phenyl]-amide

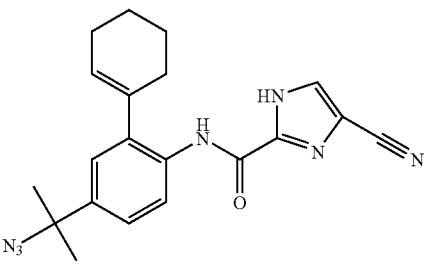

To a mixture of 4-cyano-1H-imidazole-2-carboxylic acid [2-cyclohex-1-enyl-4-(1-hydroxy-1-methyl-ethyl)-phenyl]-amide (as prepared in example 12, 15.0 mg, 0.0428 mmol) and NaN₃ (27.8 mg, 0.428 mmol) in 1 mL of chloroform at 0° C. under Ar was added TFA (49 μL, 0.642 mmol). The resulting mixture was stirred at 0° C. for 1 h under Ar. Treated with 30 mL of EtOAc, the mixture was washed with saturated NaHCO₃ aqueous solution (10 mL), brine (10 mL) and dried (Na₂SO₄). Removal of the solvent under reduced pressure followed by flash chromatography of the residue on silica gel (0-5% EtOAc/DCM) gave 13.6 mg (84%) of the title compound as a white solid. Mass spectrum (ESI, m/z): Calcd. for C₂₀H₂₁N₇O, 376.2 (M+H), found 376.0.

b) 4-Cyano-1H-imidazole-2-carboxylic acid [4-(1-amino-1-methyl-ethyl)-2-cyclohex-1-enyl-phenyl]-amide, acetic acid salt To a mixture of 4-cyano-1H-imidazole-2-carboxylic acid [4-(1-azido-1-methyl-ethyl)-2-cyclohex-1-enyl-phenyl]-amide (as prepared in the previous step, 13.6 mg, 0.0362 mmol) and zinc (9.5 mg, 0.15 mmol) in 1 mL of THF was added acetic acid (0.20 mL). The resulting mixture was stirred at RT for 3 h under Ar. The solid was removed by filtration on Celite and the filtrate was concentrated in vacuo to give a light brown oil. The mixture was triturated with DCM (2×4 mL). The solvent was removed by filtration and the solid was dried in vacuo to give 13.5 mg (91%) of the title compound as a white solid. ¹H-NMR (CD₃OD; 400 MHz): δ 8.27 (s, 1H), 7.70 (s, 1H), 7.43 (d, 1H, J=7.3 Hz), 7.29 (s, 1H), 5.81 (m, 1H), 2.11-2.37 (m, 4H), 1.91 (s, 3H), 1.59-1.84 (m, 4H), 1.71 (s, 6H).

EXAMPLE 15

4-Cyano-1H-imidazole-2-carboxylic acid [4-(6-amino-pyridin-3-yl)-2-cyclohex-1-enyl-phenyl]-amide, trifluoroacetic acid salt

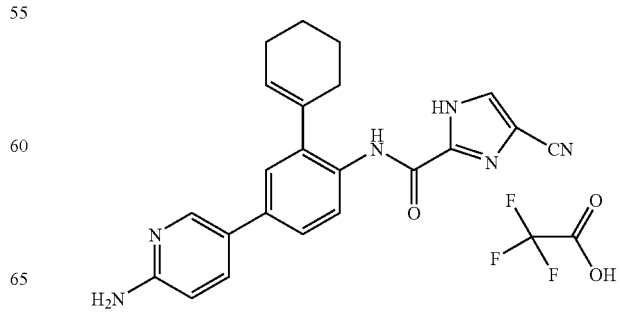

a) 4-Cyano-1-(2-trimethylsilanyl-ethoxymethyl)-1H-imidazole-2-carboxylic acid [2-cyclohex-1-enyl-4-(5,5-dimethyl-[1,3,2]dioxaborinan-2-yl)-phenyl]-amide

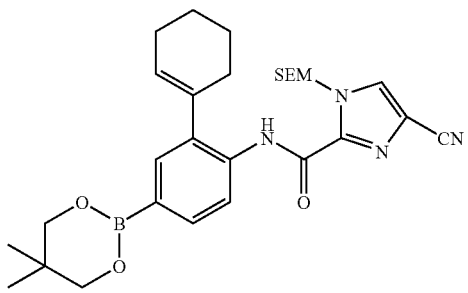

To a mixture of 4-cyano-1-(2-trimethylsilanyl-ethoxymethyl)-1H-imidazole-2-carboxylic acid (4-bromo-2-cyclohex-1-enyl-phenyl)-amide (as prepared in Example 11, step (f), 201 mg, 0.400 mmol), bis(neopentyl glycolato)diboron (108 mg, 0.480 mmol) and Pd(dppf)Cl$_2$ (29.3 mg, 0.0400 mmol) in 4 mL of 1,4-dioxane was added KOAc (118 mg, 1.20 mmol). The resulting mixture was stirred at 80° C. for 10 h under Ar. After cooling to RT, the mixture was treated with 50 mL of EtOAc, washed with H$_2$O (3×10 mL) and brine (10 mL). The organic layer was dried (Na$_2$SO$_4$) and concentrated in vacuo. The residue was purified by flash chromatography on silica gel (DCM) to afford 144 mg (67%) of the title compound as a white solid: $^1$H-NMR (CDCl$_3$; 400 MHz): δ 9.84 (s, 1H), 8.35 (d, 1H, J=8.2 Hz), 7.76 (s, 1H), 7.70 (dd, 1H, J=8.2, 1.4 Hz), 7.60 (d, 1H, J=1.4 Hz), 5.95 (s, 2H), 5.82 (m, 1H), 3.76 (s, 4H), 3.65 (t, 2H, J=8.1 Hz), 2.22-2.35 (m, 4H), 1.68-1.92 (m, 4H), 1.01 (s, 6H), 0.96 (t, 2H, J=8.1 Hz), 0.01 (s, 9H).

b) 4-Cyano-1-(2-trimethylsilanyl-ethoxymethyl)-1H-imidazole-2-carboxylic acid [4-(6-amino-pyridin-3-yl)-2-cyclohex-1-enyl-phenyl]-amide

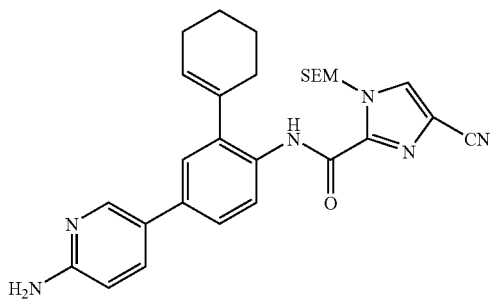

To a mixture of 4-cyano-1-(2-trimethylsilanyl-ethoxymethyl)-1H-imidazole-2-carboxylic acid [2-cyclohex-1-enyl-4-(5,5-dimethyl-[1,3,2]dioxaborinan-2-yl)-phenyl]-amide (as prepared in the previous step, 32.0 mg, 0.0600 mmol), 5-bromo-pyridin-2-ylamine (10.4 mg, 0.0660 mmol) and Pd(PPh$_3$)$_4$ (7.0 mg, 0.0060 mmol) in 1.0 mL of 1,4-dioxane was added 2.0 M Na$_2$CO$_3$ aqueous solution (0.24 mL, 0.48 mmol). The resulting mixture was stirred at 80. C for 6 h under Ar. After cooling to RT, the mixture was treated with 30 mL of EtOAc, washed with H$_2$O (3×15 mL) and brine (10 mL). The organic layer was dried (Na$_2$SO$_4$) and concentrated in vacuo. The residue was purified by flash chromatography on silica gel (2-3% MeOH/DCM) to afford 24 mg (78%) of the title compound as a white solid: Mass spectrum (ESI, m/z): Calcd. for C$_{28}$H$_{34}$N$_6$O$_2$Si, 515.3 (M+H), found 515.2.

c) 4-Cyano-1H-imidazole-2-carboxylic acid [4-(6-amino-pyridin-3-yl)-2-cyclohex-1-enyl-phenyl]-amide, trifluoroacetic acid salt To a solution of 4-cyano-1-(2-trimethylsilanyl-ethoxymethyl)-1H-imidazole-2-carboxylic acid [4-(6-amino-pyridin-3-yl)-2-cyclohex-1-enyl-phenyl]-amide (as prepared in the previous step, 22 mg, 0.043 mmol) in 1.5 mL of DCM was added 50 μL of EtOH followed by 0.50 mL of TFA. The resulting solution was stirred at RT for 1 d. The reaction was treated with 20 mL of n-propanol and concentrated in vacuo. The residue was purified by flash chromatography on silica gel (3-5% MeOH/DCM) to afford 17 mg (77%) of the title compound as a white solid. $^1$H-NMR (CD$_3$OD; 400 MHz): δ 8.37 (dd, 1H, J=8.5, 1.9 Hz), 8.27 (ddd, 1H, J=9.3, 2.3, 1.9 Hz), 8.11 (m, 1H), 8.03 (m, 1H), 7.54 (ddd, 1H, J=8.5, 2.3, 1.9 Hz), 7.45 (m, 1H), 7.11 (br d, 1H, J=9.3 Hz), 5.90 (m, 1H), 2.25-2.35 (m, 4H), 1.76-1.93 (m, 4H). Mass spectrum (ESI, m/z): Calcd. for C$_{22}$H$_{20}$N$_6$O, 385.2 (M+H), found 385.1.

EXAMPLE 16

5-Cyano-1H-imidazole-2-carboxylic acid [2-cyclohex-1-enyl-4-(1-oxy-pyridin-4-yl)-phenyl]-amide

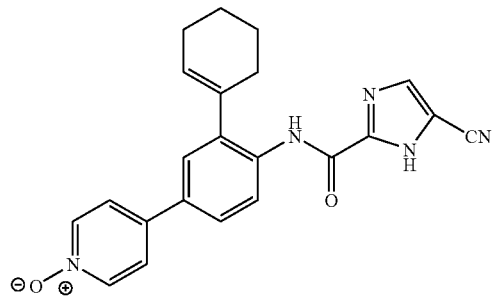

a) 4-(1-Oxy-pyridin-4-yl)-phenylamine

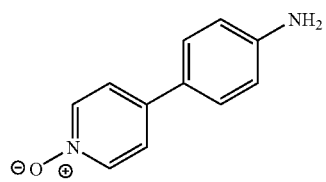

To a mixture of 4-chloro-pyridine 1-oxide (389 mg, 3.00 mmol), 4-(4,4,5,5-tetramethyl-[1,3,2]dioxaborolan-2-yl)-phenylamine (712 mg, 3.15 mmol) and Pd(PPh$_3$)$_4$ (347 mg, 0.30 mmol) in 20 mL of 1,4-dioxane was added 2.0 M aq Na$_2$CO$_3$ solution (3.0 mL, 6.00 mmol). The resulting mixture was stirred at 80° C. for 24 h under Ar, and then cooled to RT. Treated with 50 mL of brine, the mixture was extracted with DCM (10×30 mL). The combined organic layers were concentrated in vacuo and purified by flash chromatography on silica gel (2-6% MeOH/DCM) to give 280 mg (50%) of the title compound as white solid. $^1$H-NMR (CDCl$_3$; 400 MHz): δ 8.24 (d, 2H, J=7.3 Hz), 7.46 (d, 2H, J=7.3 Hz), 7.43 (d, 2H, J=8.6 Hz), 6.77 (d, 2H, J=8.6 Hz). Mass spectrum (ESI, m/z): Calcd. for C$_{11}$H$_{10}$N$_2$O, 187.1 (M+H), found 187.1.

b) 2-Bromo-4-(1-oxy-pyridin-4-yl)-phenylamine

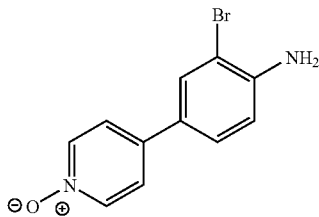

To a solution of 4-(1-oxy-pyridin-4-yl)-phenylamine (as prepared in the previous step, 200 mg, 1.07 mmol) in 20 mL of 4:1 DCM/MeOH at 0° C. was added a solution of N-bromosuccinimide (NBS) (191 mg, 1.07 mmol) in 10 mL of DCM under Ar. The mixture was stirred at 0° C. for 1 h. Treated with 20 mL of satd aq NaHCO$_3$ solution and 20 mL of brine, the mixture was extracted with DCM (5×50 mL). The combined organic layers were concentrated in vacuo and purified by flash chromatography on silica gel (2-6% MeOH/DCM) to give 248 mg (87%) of the title compound as a white solid. $^1$H-NMR (CDCl$_3$; 400 MHz): δ 8.20 (d, 2H, J=7.4 Hz), 7.67 (d, 1H, J=2.1 Hz), 7.40 (d, 2H, J=7.4 Hz), 7.35 (dd, 1H, J=8.4, 2.1 Hz), 6.84 (d, 1H, J=8.4 Hz), 3.90-4.60 (br s, 2H). Mass spectrum (ESI, m/z): Calcd. for C$_{11}$H$_9$BrN$_2$O, 265.0 (M+H), found 265.1.

c) 2-Cyclohex-1-enyl-4-(1-oxy-pyridin-4-yl)-phenyl amine

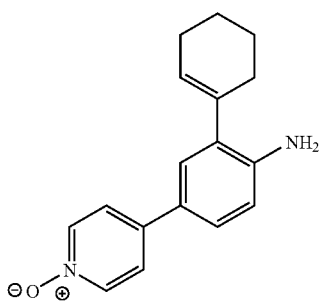

To a mixture of 2-bromo-4-(1-oxy-pyridin-4-yl)-phenylamine (as prepared in the previous step, 240 mg, 0.905 mmol), cyclohexen-1-yl boronic acid (126 mg, 0.996 mmol) and Pd(PPh$_3$)$_4$ (105 mg, 0.091 mmol) in 9 mL of 1,4-dioxane was added 2.0 M aq Na$_2$CO$_3$ solution (3.62 mL, 7.24 mmol). The resulting mixture was stirred at 80° C. for 8 h under Ar, and then cooled to RT. Treated with 20 mL of brine, the mixture was extracted with DCM (4×20 mL). The combined organic layers were concentrated in vacuo and purified by flash chromatography on silica gel (2-5% MeOH/DCM) to give 241 mg (100%) of the title compound as a light yellow solid. $^1$H-NMR (CDCl$_3$; 400 MHz): δ 8.18 (d, 2H, J=7.3 Hz), 7.44 (d, 2H, J=7.3 Hz), 7.30 (dd, 1H, J=8.4, 2.2 Hz), 6.76 (d, 1H, J=8.4 Hz), 5.80 (m, 1H), 3.0-4.2 (br s, 2H), 2.17-2.28 (m, 4H), 1.68-1.82 (m, 4H). Mass spectrum (ESI, m/z): Calcd. for C$_{17}$H$_{18}$N$_2$O, 267.1 (M+H), found 267.1.

d) 4-Cyano-1-(2-trimethylsilanyl-ethoxymethyl)-1H-imidazole-2-carboxylic acid [2-cyclohex-1-enyl-4-(1-oxy-pyridin-4-yl)-phenyl]-amide

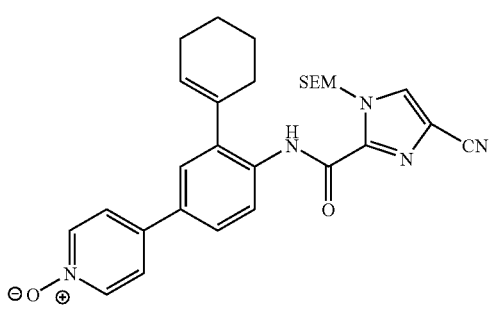

To a mixture of 2-cyclohex-1-enyl-4-(1-oxy-pyridin-4-yl)-phenylamine (Example 17, step (c), 107 mg, 0.40 mmol), potassium 4-cyano-1-(2-trimethylsilanyl-ethoxymethyl)-1H-imidazole-2-carboxylate (Example 11, step (d), 129 mg, 0.42 mmol) and PyBroP (187 mg, 0.42 mmol) in 4 mL of DMF was added DIEA (209 µL, 1.20 mmol). The resulting mixture was stirred at RT for 5 h under Ar. Treated with 50 mL of EtOAc, the mixture was washed with H$_2$O (2×10 mL), brine (10 mL) and dried (Na$_2$SO$_4$). Removal of the solvent under reduced pressure followed by flash chromatography of the residue on silica gel (1-5% MeOH/DCM) gave 86 mg (42%) of the title compound as a light yellow oil. $^1$H-NMR (CDCl$_3$; 400 MHz): δ 9.84 (s, 1H), 8.51 (d, 1H, J=8.7 Hz), 8.25 (d, 2H, J=7.2 Hz), 7.81 (s, 1H), 7.52 (m, 3H), 7.41 (d, 1H, J=2.3 Hz), 5.96 (s, 2H), 5.92 (m, 1H), 3.68 (t, 2H, J=8.3 Hz), 2.25-2.37 (m, 4H), 1.70-1.94 (m, 4H), 0.99 (t, 2H, J=8.3 Hz), 0.012 (s, 9H). Mass spectrum (ESI, m/z): Calcd. for C$_{28}$H$_{33}$N$_5$O$_3$Si, 516.2 (M+H), found 516.1.

e) 5-Cyano-1H-imidazole-2-carboxylic acid [2-cyclohex-1-enyl-4-(1-oxy-pyridin-4-yl)-phenyl]-amide To a solution of 4-cyano-1-(2-trimethylsilanyl-ethoxymethyl)-1H-imidazole-2-carboxylic acid [2-cyclohex-1-enyl-4-(1-oxy-pyridin-4-yl)-phenyl]-amide (as prepared in the previous step, 40 mg, 0.078 mmol) in 3 mL of DCM was added 0.10 mL of EtOH followed by 1 mL of TFA. The resulting solution was stirred at RT for 2 h. Removal of the solvent under reduced pressure followed by flash chromatography of the residue on silica gel (3-5% MeOH/DCM) gave 29.3 mg (98%) of the title compound as a white solid. $^1$H-NMR (1:1 CDCl$_3$/CD$_3$OD; 400 MHz): δ 8.50 (d, 1H, J=8.7 Hz), 8.29 (d, 2H, J=7.3 Hz), 7.81 (s, 1H), 7.68 (d, 2H, J=7.3 Hz), 7.58 (dd, 1H, J=8.7, 2.3), 7.47 (d, 1H, J=2.3 Hz), 5.94 (m, 1H), 2.26-2.39 (m, 4H), 1.79-1.94 (m, 4H). Mass spectrum (ESI, m/z): Calcd. for C$_{22}$H$_{19}$N$_5$O$_2$, 386.1 (M+H), found 386.1.

EXAMPLE 17

5-Cyano-1H-imidazole-2-carboxylic acid (2-cyclohex-1-enyl-4-pyridin-4-yl-phenyl)-amide

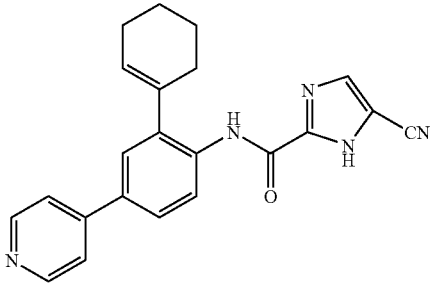

A mixture of 5-cyano-1H-imidazole-2-carboxylic acid [2-cyclohex-1-enyl-4-(1-oxy-pyridin-4-yl)-phenyl]-amide (as prepared in Example 16, step (e), 14 mg, 0.036 mmol), iron powder (10 mg, 0.18 mmol) and $NH_4Cl$ (19 mg, 0.036 mmol) in 4 mL of ethanol was stirred at 80° C. for 5 h, and then cooled to RT. Treated with 20 mL of $H_2O$, the mixture was extracted with EtOAc (3×20 mL). The combined organic layers were concentrated in vacuo and purified by flash chromatography on silica gel (1-2% MeOH/DCM) to give 10.1 mg (69%) of the title compound as a white solid: $^1$H-NMR (CDCl$_3$; 400 MHz): δ 8.57 (d, 2H, J=6.3 Hz), 8.49 (d, 1H, J=8.7 Hz), 7.89 (s, 1H), 7.63-7.68 (m, 3H), 7.54 (d, 1H, J=2.0 Hz), 5.94 (m, 1H), 2.27-2.39 (m, 4H), 1.80-1.94 (m, 4H). Mass spectrum (ESI, m/z): Calcd. for $C_{22}H_{19}N_5O$, 370.2 (M+H), found 370.1.

EXAMPLE 18

4-Cyano-1H-imidazole-2-carboxylic acid [2-cyclohex-1-enyl-4-(1-oxy-pyridin-3-yl)-phenyl]-amide

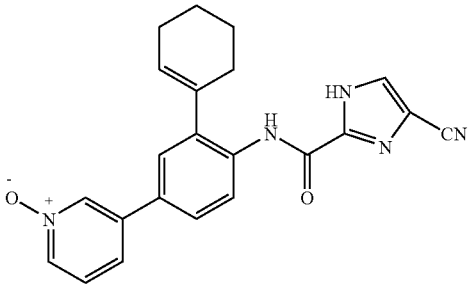

a) 3-Bromopyridine 1-oxide

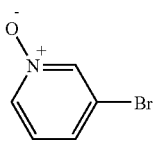

A solution of 3-bromopyridine (158 mg, 1.00 mmol) and urea hydrogen peroxide (658 mg, 7.00 mmol) in 2.5 mL of formic acid was stirred at RT for 16 h. The resulting mixture was treated with $H_2O$ (30 mL) and extracted with DCM (3×15). The combined organic layers were dried (Na$_2$SO$_4$) and concentrated to give 87 mg (50%) of the title compound as a colorless oil. Mass spectrum (ESI, m/z): Calcd. for $C_5H_4BrNO$, 174.0 (M+H), found 174.2.

b) 4-Cyano-1-(2-trimethylsilanyl-ethoxymethyl)-1H-imidazole-2-carboxylic acid [2-cyclohex-1-enyl-4-(1-oxy-pyridin-3-yl)-phenyl]-amide

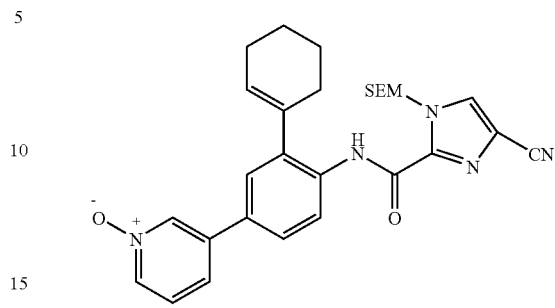

The title compound was prepared by the Suzuki coupling procedure of Example 15, step (b) using 4-cyano-1-(2-trimethylsilanyl-ethoxymethyl)-1H-imidazole-2-carboxylic acid [2-cyclohex-1-enyl-4-(5,5-dimethyl-[1,3,2]dioxaborinan-2-yl)-phenyl]-amide (as prepared in the Example 15, step (a), 53.5 mg, 0.100 mmol), and 3-bromopyridine 1-oxide (as prepared in the previous step, 20.9 mg, 0.120 mmol). Silica gel chromatography (1-3% MeOH/DCM) afforded the title compound (49 mg, 95%) as a colorless oil. Mass spectrum (ESI, m/z): Calcd. for $C_{28}H_{33}N_5O_3Si$, 516.2 (M+H), found 516.1.

c) 4-Cyano-1H-imidazole-2-carboxylic acid [2-cyclohex-1-enyl-4-(1-oxy-pyridin-3-yl)-phenyl]-amide The title compound was prepared by the procedure of Example 15, step (c) using 4-cyano-1-(2-trimethylsilanyl-ethoxymethyl)-1H-imidazole-2-carboxylic acid [2-cyclohex-1-enyl-4-(1-oxy-pyridin-3-yl)-phenyl]-amide (as prepared in the previous step, 49 mg, 0.095 mmol). Silica gel chromatography (1-4% MeOH/DCM) afforded the title compound (35 mg, 96%) as a white solid. $^1$H-NMR (DMSO-d$_6$; 400 MHz): δ 9.85 (s, 1H), 8.63 (s, 1H), 8.36 (s, 1H), 8.21 (ddd, 1H, J=6.5, 1.5, 0.8 Hz), 8.17 (d, 1H, J=8.5 Hz), 7.69-7.72 (m, 2H), 7.62 (d, 1H, J=2.3), 7.49 (dd, 1H, J=8.0, 6.5 Hz), 5.86 (m, 1H), 2.16-2.33 (m, 4H), 1.64-1.81 (m, 4H). Mass spectrum (ESI, m/z): Calcd. for $C_{22}H_{19}N_5O_2$, 386.2 (M+H), found 386.1.

EXAMPLE 19

4-Cyano-1H-imidazole-2-carboxylic acid (2-cyclohex-1-enyl-4-pyridin-3-yl-phenyl)-amide

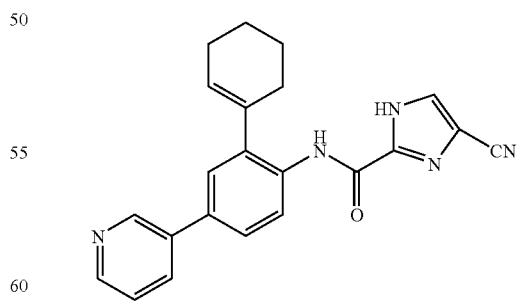

A mixture of 4-cyano-1H-imidazole-2-carboxylic acid [2-cyclohex-1-enyl-4-(1-oxy-pyridin-3-yl)-phenyl]-amide (as prepared in Example 18, step (c), 18.0 mg, 0.0467 mmol), iron powder (13.0 mg, 0.234 mmol) and NH$_4$Cl (25.0 mg, 0.467 mmol) in 4.0 mL of EtOH was stirred at 80° C. for 6 h under Ar. After cooling to RT, the mixture was treated with brine (20 mL) and extracted with DCM (4×15 mL). The combined organic layers were dried (Na$_2$SO$_4$) and concentrated in vacuo. The residue was purified by flash chromatography on silica gel (1-3% MeOH/DCM) to give 15.0 mg (87%) of the title compound as a white solid. $^1$H-NMR (CDCl$_3$; 400 MHz): δ 12.61 (s, 1H), 9.65 (s, 1H), 8.61 (m, 1H), 8.50 (d, 1H, J=8.5 Hz), 7.90 (ddd, 1H, J=7.9, 1.9, 1.9 Hz), 7.75 (s, 1H), 7.54 (dd, 1H, J=8.5, 2.1 Hz), 7.42 (d, 2H, J=2.1 Hz), 7.38 (dd, 1H, J=7.9, 4.8 Hz), 5.94 (m, 1H), 2.27-2.37 (m, 4H), 1.78-1.93 (m, 4H). Mass spectrum (ESI, m/z): Calcd. for C$_{22}$H$_{19}$N$_5$O, 370.2 (M+H), found 370.1.

EXAMPLE 20

4-Cyano-1H-imidazole-2-carboxylic acid [2-cyclohex-1-enyl-4-(1-oxy-pyridin-2-yl)-phenyl]-amide

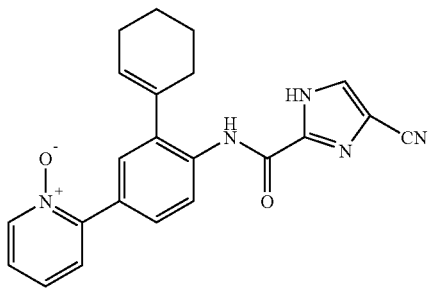

a) 2-Bromo-pyridine 1-oxide

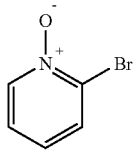

A solution of 2-bromopyridine (158 mg, 1.00 mmol) and urea hydrogen peroxide (658 mg, 7.00 mmol) in 2.5 mL of formic acid was stirred at RT for 16 h. The resulting mixture was treated with H$_2$O (30 mL) and extracted with DCM (3×15). The combined organic layers were dried (Na$_2$SO$_4$) and concentrated to give 96 mg (55%) of the title compound as a brown oil. Mass spectrum (ESI, m/z): Calcd. for C$_5$H$_4$BrNO, 174.0 (M+H), found 174.2.

b) 4-Cyano-1-(2-trimethylsilanyl-ethoxymethyl)-1H-imidazole-2-carboxylic acid [2-cyclohex-1-enyl-4-(1-oxy-pyridin-2-yl)-phenyl]-amide

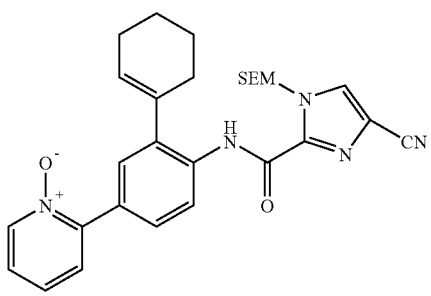

The title compound was prepared by the Suzuki coupling procedure of Example 15, step (b) using 4-cyano-1-(2-trimethylsilanyl-ethoxymethyl)-1H-imidazole-2-carboxylic acid [2-cyclohex-1-enyl-4-(5,5-dimethyl-[1,3,2]dioxaborinan-2-yl)-phenyl]-amide (as prepared in Example 15, step (a), 53.5 mg, 0.100 mmol), and 2-bromopyridine 1-oxide (as prepared in the previous step, 20.9 mg, 0.120 mmol). Silica gel chromatography (1-3% MeOH/DCM) afforded the title compound (49 mg, 95%) as a colorless oil. Mass spectrum (ESI, m/z): Calcd. for C$_{28}$H$_{33}$N$_5$O$_3$Si, 516.2 (M+H), found 516.0.

c) 4-Cyano-1H-imidazole-2-carboxylic acid [2-cyclohex-1-enyl-4-(1-oxy-pyridin-2-yl)-phenyl]-amide The title compound was prepared by the procedure of Example 15, step (c) using 4-cyano-1-(2-trimethylsilanyl-ethoxymethyl)-1H-imidazole-2-carboxylic acid [2-cyclohex-1-enyl-4-(1-oxy-pyridin-2-yl)-phenyl]-amide (as prepared in the previous step, 49 mg, 0.095 mmol). Silica gel chromatography (1-4% MeOH/DCM) afforded the title compound (35 mg, 96%) as a light blue solid. $^1$H-NMR (DMSO-d$_6$; 400 MHz): δ 12.66 (s, 1H), 9.59 (s, 1H), 8.53 (d, 1H, J=5.4 Hz), 7.79 (d, 1H, J=7.8 Hz), 7.64 (s, 1H), 7.43-7.59 (m, 4H), 7.35 (br s, 1H), 5.79 (m, 1H), 2.01-2.47 (m, 4H), 1.70-1.89 (m, 4H). Mass spectrum (ESI, m/z): Calcd. for C$_{22}$H$_{19}$N$_5$O$_2$, 386.2 (M+H), found 386.1.

EXAMPLE 21

4-Cyano-1H-imidazole-2-carboxylic acid (2-cyclohex-1-enyl-4-pyridin-2-yl-phenyl)-amide

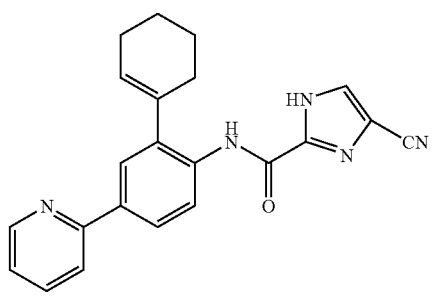

The title compound was prepared by the procedure of Example 19, using 4-cyano-1H-imidazole-2-carboxylic acid [2-cyclohex-1-enyl-4-(1-oxy-pyridin-2-yl)-phenyl]-amide (as prepared in Example 20, step (c), 18 mg, 0.047 mmol). Silica gel chromatography (1-3% MeOH/DCM) afforded the title compound (5.2 mg, 30%) as a white solid. $^1$H-NMR (CDCl$_3$; 400 MHz): δ11.85 (s, 1H), 9.69 (s, 1H), 8.71 (br s, 1H), 8.48 (d, 1H, J=8.1 Hz), 7.86-7.98 (m, 2H), 7.65-7.83 (m, 3H), 7.24 (m, 1H), 5.93 (m, 1H), 2.24-2.40 (m, 4H), 1.76-1.92 (m, 4H). Mass spectrum (ESI, m/z): Calcd. for C$_{22}$H$_{19}$N$_5$O, 370.2 (M+H), found 370.1.

EXAMPLE 22

4-Cyano-1H-imidazole-2-carboxylic acid (2-cyclohex-1-enyl-4-isopropyl-phenyl)-amide

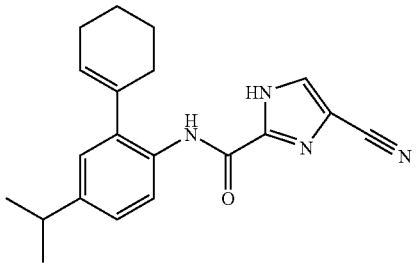

a) 2-Cyclohex-1-enyl-4-isopropyl-phenylamine

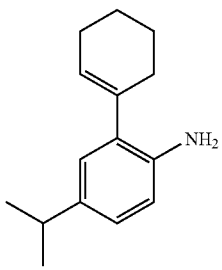

To a mixture of 2-bromo-4-isopropyl-phenylamine (214 mg, 1.00 mmol), cyclohexane-1-enyl boronic acid (139 mg, 1.10 mmol) and Pd(PPh$_3$)$_4$ (116 mg, 0.100 mmol) in 5 mL of 1,4-dioxane was added 2.0 M aqueous Na$_2$CO$_3$ solution (4.0 mL, 8.0 mmol). The resulting mixture was stirred at 80° C. for 8 h under Ar, and then cooled to RT. The reaction was treated with EtOAc (20 mL) and washed with H$_2$O (2×10 mL) and brine (10 mL). The organic layer was dried over Na$_2$SO$_4$ and concentrated in vacuo. The residue was purified by flash chromatography on silica gel (DCM) to give 205 mg (95%) of the title compound as a light brown oil. Mass spectrum (ESI, m/z): Calcd. for C$_{15}$H$_{21}$N, 216.2 (M+H), found 216.1.

b) 4-Cyano-1-(2-trimethylsilanyl-ethoxymethyl)-1H-imidazole-2-carboxylic acid (2-cyclohex-1-enyl-4-isopropyl-phenyl)-amide

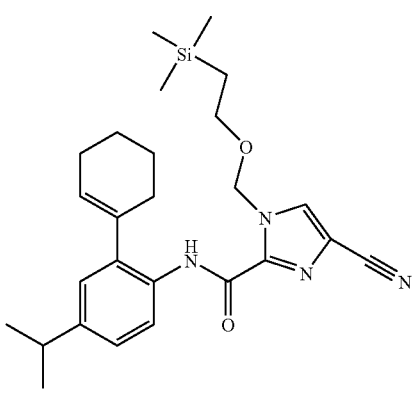

To a mixture of 2-cyclohex-1-enyl-4-isopropyl-phenylamine (as prepared in the previous step, 30.0 mg, 0.139 mmol), potassium 4-cyano-1-(2-trimethylsilanyl-ethoxymethyl)-1H-imidazole-2-carboxylate (as prepared in Example 11, step (d), 43.0 mg, 0.141 mmol) and PyBroP (65.0 mg, 0.139 mmol) in 1.5 mL of DMF was added DIEA (73 µL, 0.417 mmol). The resulting mixture was stirred at RT for 16 h under Ar. Treated with 30 mL of EtOAc, the mixture was washed with H$_2$O (2×10 mL), brine (10 mL) and dried (Na$_2$SO$_4$). Removal of the solvent under reduced pressure followed by flash chromatography of the residue on silica gel (DCM) gave 55.4 mg (86%) of the title compound as a colorless oil. Mass spectrum (ESI, m/z): Calcd. for C$_{26}$H$_{36}$N$_4$O$_2$Si, 465.3 (M+H), found 464.9.

c) 4-Cyano-1-(2-trimethylsilanyl-ethoxymethyl)-1H-imidazole-2-carboxylic acid (2-cyclohex-1-enyl-4-isopropyl-phenyl)-amide To a solution of 4-cyano-1-(2-trimethylsilanyl-ethoxymethyl)-1H-imidazole-2-carboxylic acid (2-cyclohex-1-enyl-4-isopropyl-phenyl)-amide (as prepared in the previous step, 50.0 mg, 0.108 mmol) in 6 mL of DCM was added 0.20 mL of EtOH followed by 2 mL of TFA. The resulting solution was stirred at RT for 2 h. Removal of the solvent under reduced pressure followed by flash chromatography of the residue on silica gel (1-4% EtOAc/DCM) gave 29.5 mg (82%) of the title compound as a white solid. $^1$H-NMR (CDCl$_3$; 400 MHz): δ 12.77 (s, 1H), 9.64 (s, 1H), 8.23 (d, 1H, J=8.5 Hz), 7.75 (s, 1H), 7.19 (dd, 1H, J=8.5, 2.1 Hz), 7.07 (d, 1H, J=2.1 Hz), 5.86 (m, 1H), 2.91 (m, 1H), 2.22-2.36 (m, 4H), 1.70-1.89 (m, 4H), 1.27 (d, 6H, J=7.0 Hz). Mass spectrum (ESI, m/z): Calcd. for C$_{20}$H$_{22}$N$_4$O, 335.2 (M+H), found 335.0.

EXAMPLE 23

4-Cyano-1H-imidazole-2-carboxylic acid (2-piperidin-1-yl-phenyl)-amide, trifluoroacetic acid salt

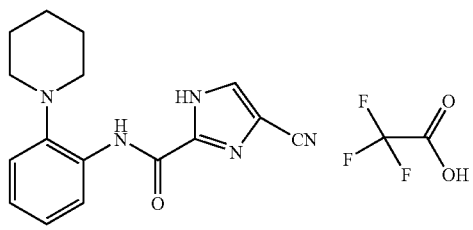

a) 4-Cyano-1-(2-trimethylsilanyl-ethoxymethyl)-1H-imidazole-2-carboxylic acid (2-piperidin-1-yl-phenyl)-amide

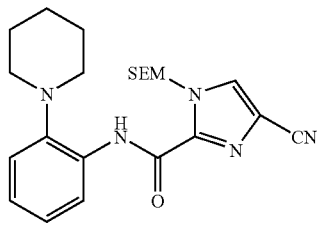

To a mixture of 2-piperidin-1-yl-phenylamine (63.5 mg, 0.360 mmol), potassium 4-cyano-1-(2-trimethylsilanylethoxymethyl)-1H-imidazole-2-carboxylate (as prepared in Example 11, step (d), 100 mg, 0.327 mmol) and PyBroP (152 mg, 0.327 mmol) in 4 mL of 1,2-dichloroethane was added DIEA (171 µL, 0.981 mmol). After stirring at RT for 16 h under Ar, the mixture was treated with 50 mL of EtOAc, washed with $H_2O$ (2×10 mL) and brine (10 mL). The organic layer was dried ($Na_2SO_4$) and concentrated in vacuo. The residue was purified by flash chromatography on silica gel (5-10% EtOAc/hexane) to afford 118 mg (85%) of the title compound as a white solid. Mass spectrum (ESI, m/z): Calcd. for $C_{22}H_{31}N_5O_2Si$, 426.2 (M+H), found 426.1.

b) 4-Cyano-1H-imidazole-2-carboxylic acid (2-piperidin-1-yl-phenyl)-amide, trifluoroacetic acid salt The title compound was prepared by the procedure of Example 22, step (c) using 4-cyano-1-(2-trimethylsilanyl-ethoxymethyl)-1H-imidazole-2-carboxylic acid (2-piperidin-1-yl-phenyl)-amide (as prepared in the previous step, 110 mg, 0.258 mmol). Silica gel chromatography (1-3% MeOH/DCM) afforded the title compound (85 mg, 80%) as a white solid. $^1$H-NMR (CDCl$_3$; 400 MHz): δ 9.94-10.87 (br s, 3H), 8.00 (m, 1H), 7.80 (s, 1H), 7.30-7.39 (m, 3H), 2.99-3.34 (m, 4H), 1.87-2.06 (m, 4H), 1.54-1.83 (m, 2H). Mass spectrum (ESI, m/z): Calcd. for $C_{16}H_{17}N_5O$, 296.1 (M+H), found 296.1.

EXAMPLE 24

4-Cyano-5-(1-hydroxy-1-methyl-ethyl)-1H-imidazole-2-carboxylic acid (4-bromo-2-cyclohex-1-enyl-phenyl)-amide

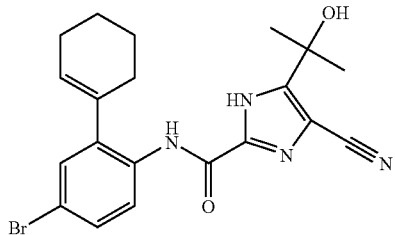

a) 4-Cyano-5-(1-hydroxy-1-methyl-ethyl)-1-(2-trimethylsilanyl-ethoxymethyl)-1H-imidazole-2-carboxylic acid (4-bromo-2-cyclohex-1-enyl-phenyl)-amide To a solution of 4-cyano-1-(2-trimethylsilanyl-ethoxymethyl)-1H-imidazole-2-carboxylic acid (4-bromo-2-cyclohex-1-enyl-phenyl)-amide (as prepared in Example 11, step (f), 50.0 mg, 0.100 mmol) in 1 mL of THF at −78° C. under Ar was added isopropyl magnesium chloride (55 µL, 0.11 mmol, 2.0 M in THF). The resulting mixture was warmed to RT and stirred for 15 min, cooled back to −78° C. To the mixture was added n-butyllithium (55 µL, 0.11 mmol, 2.0 M in cyclohexane) and the resulting mixture was stirred at −78° C. for 0.5 h under Ar. Acetone (30 µL, 0.40 mmol) was added and the reaction was warmed to RT and stirred for 16 h under Ar. Treated with 5 mL of saturated NH$_4$Cl aqueous solution followed by 30 mL of EtOAc, the mixture was washed with $H_2O$ (10 mL), brine (5 mL) and dried ($Na_2SO_4$). The solvent was evaporated under reduced pressure and the residue was purified by flash chromatography on silica gel (5-10% EtOAc/hexane) to afford 40.0 mg (84%) of the title compound as a white solid. Mass spectrum (ESI, m/z): Calcd. for $C_{26}H_{35}BrN_4O_3Si$, 559.2 (M+H), found 558.9.

b) 4-Cyano-5-(1-hydroxy-1-methyl-ethyl)-1H-imidazole-2-carboxylic acid (4-bromo-2-cyclohex-1-enyl-phenyl)-amide A solution of 4-cyano-5-(1-hydroxy-1-methyl-ethyl)-1-(2-trimethylsilanyl-ethoxymethyl)-1H-imidazole-2-carboxylic acid (4-bromo-2-cyclohex-1-enyl-phenyl)-amide (as prepared in the previous step, 40.0 mg, 0.0715 mmol) and tetrabutylammomium fluoride (357 µL, 0.357 mmol, 1.0 M in THF) in 2.0 mL of THF was stirred under Ar at 50° C. for 16 h and at reflux for 3 h. After cooling to RT, the mixture was treated with EtOAc (40 mL) and washed with saturated NH$_4$Cl aqueous solution (5 mL), brine (10 mL) and dried ($Na_2SO_4$). The organic layer was concentrated in vacuo and residue was purified by flash chromatography on silica gel (5-10% EtOAc/DCM) to give 26 mg (84%) of the title compound as a white solid. $^1$H-NMR (CDCl$_3$; 400 MHz): δ 11.79 (s, 1H), 9.55 (s, 1H), 8.23 (d, 1H, J=8.6 Hz), 7.42 (dd, 1H, J=8.6, 2.3 Hz), 7.33 (d, 1H, J=2.3 Hz), 5.87 (m, 1H), 5.08 (s, 1H), 2.16-2.34 (m, 4H), 1.83 (s, 6H), 1.71-1.88 (m, 4H). Mass spectrum (ESI, m/z): Calcd. for $C_{20}H_{21}BrN_4O_2$, 429.1 (M+H), found 428.9.

EXAMPLE 25

4-Cyano-1H-imidazole-2-carboxylic acid (4-acetyl-2-cyclohex-1-enyl-phenyl)-amide

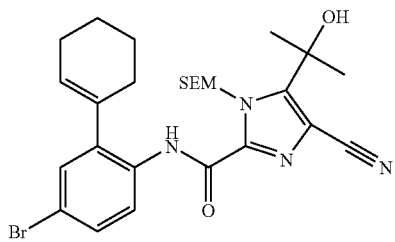

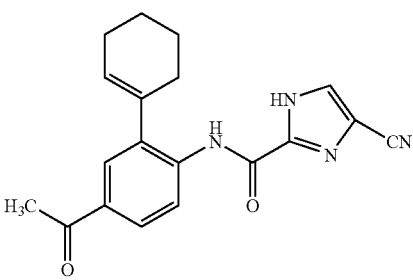

a) 4-Cyano-1-(2-trimethylsilanyl-ethoxymethyl)-1H-imidazole-2-carboxylic acid (4-acetyl-2-cyclohex-1-enyl-phenyl)-amide

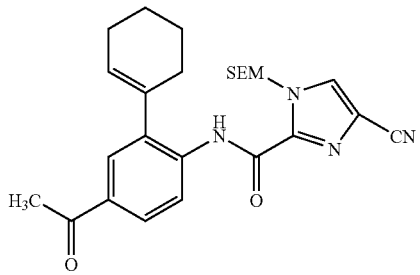

A mixture of 4-cyano-1-(2-trimethylsilanyl-ethoxymethyl)-1H-imidazole-2-carboxylic acid (4-bromo-2-cyclohex-1-enyl-phenyl)-amide (as prepared in Example 11, step (f), 100 mg, 0.199 mmol), tributyl(1-ethoxyvinyl)tin (86.3 mg, 0.239 mmol) and Pd(PPh$_3$)$_2$Cl$_2$ (10.5 mg, 0.0149 mmol) in 2 mL of 1,4-dioxane was stirred at 90° C. for 2 h under Ar. After cooling to RT, the reaction was treated with EtOAc (40 mL) and washed with 15% citric acid aqueous solution (2×10 mL), H$_2$O (10 mL) and brine (10 mL). The organic layer was dried over Na$_2$SO$_4$ and concentrated in vacuo. The residue was purified by flash chromatography on silica gel (10-20% EtOAc/hexane) to give 80.1 mg (86%) of the title compound as a light brown oil. Mass spectrum (ESI, m/z): Calcd. for C$_{25}$H$_{32}$N$_4$O$_3$Si, 465.2 (M+H), found 465.1.

b) 4-Cyano-1H-imidazole-2-carboxylic acid (4-acetyl-2-cyclohex-1-enyl-phenyl)-amide The title compound was prepared by the procedure of Example 15, step (c) using 4-cyano-1-(2-trimethylsilanyl-ethoxymethyl)-1H-imidazole-2-carboxylic acid (4-acetyl-2-cyclohex-1-enyl-phenyl)-amide (as prepared in the previous step, 40.0 mg, 0.0862 mmol). Silica gel chromatography (10% EtOAc/DCM) afforded the title compound (26.2 mg, 91%) as a white solid. $^1$H-NMR (CDCl$_3$; 400 MHz): δ 11.59 (s, 1H), 9.79 (s, 1H), 8.50 (d, 1H, J=8.6 Hz), 7.92 (dd, 1H, J=8.6, 2.0 Hz), 7.82 (d, 1H, J=2.0 Hz), 7.78 (s, 1H), 5.92 (m, 1H), 2.62 (s, 3H), 2.23-2.39 (m, 4H), 1.77-1.94 (m, 4H). Mass spectrum (ESI, m/z): Calcd. for C$_{19}$H$_{18}$N$_4$O$_2$, 335.1 (M+H), found 335.1.

EXAMPLE 26

4-Cyano-1H-imidazole-2-carboxylic acid (4-carbamoyl-2-cyclohex-1-enyl-phenyl)-amide

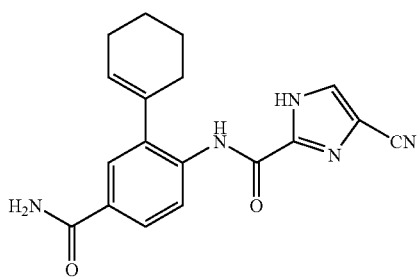

a) 4-Amino-3-bromo-benzamide

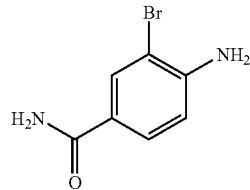

To a suspension of 4-amino-benzamide (1.00 g, 7.34 mmol) in 50 mL of 1:4 CH$_3$CN/DCM at 0° C. was added N-bromosuccinimide (NBS) (1.31 g, 7.34 mmol) in 20 mL of 1:1 CH$_3$CN/DCM. The mixture was warmed to RT and stirred for 16 h under Ar. Treated with 100 mL of EtOAc, the mixture was washed with H$_2$O (2×30 mL), brine (20 mL) and dried (Na$_2$SO$_4$). The organic solvent was evaporated in vacuo and the residue was triturated with DCM to give 1.45 g (92%) of the title compound as a faint yellow solid. Mass spectrum (ESI, m/z): Calcd. for C$_7$H$_7$BrN$_2$O, 215.0 (M+H), found 215.1.

b) 4-Amino-3-cyclohex-1-enyl-benzamide

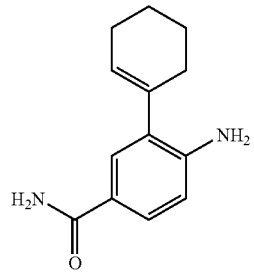

The title compound was prepared by the Suzuki coupling procedure of Example 11, step (e) using 4-amino-3-bromo-benzamide (as prepared in the previous step, 500 mg, 2.32 mmol), and cyclohexane-1-enyl boronic acid (322 mg, 2.56 mmol). The mixture was purified by trituration with DCM to afford the title compound (382 mg, 76%) as a yellow solid. Mass spectrum (ESI, m/z): Calcd. for C$_{13}$H$_{16}$N$_2$O, 217.1 (M+H), found 217.2.

c) 4-Cyano-1-(2-trimethylsilanyl-ethoxymethyl)-1H-imidazole-2-carboxylic acid (4-carbamoyl-2-cyclohex-1-enyl-phenyl)-amide

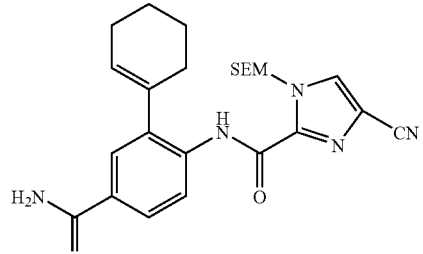

The title compound was prepared by the procedure of Example 11, step (f) using 4-amino-3-cyclohex-1-enyl-benzamide (as prepared in the previous step, 100 mg, 0.462 mmol) and potassium 4-cyano-1-(2-trimethylsilanyl-ethoxymethyl)-1H-imidazole-2-carboxylate (as prepared in Example 11, step (d), 155 mg, 0.509 mmol). Silica gel chromatography (1-2% MeOH/DCM) afforded the title compound (210 mg, 98%) as a white solid. Mass spectrum (ESI, m/z): Calcd. for C$_{24}$H$_{31}$N$_5$O$_3$Si, 466.2 (M+H), found 466.1.

d) 4-Cyano-1H-imidazole-2-carboxylic acid (4-carbamoyl-2-cyclohex-1-enyl-phenyl)-amide To a solution of 4-cyano-1-(2-trimethylsilanyl-ethoxymethyl)-1H-imidazole-2-carboxylic acid (4-carbamoyl-2-cyclohex-1-enyl-phenyl)-amide (as prepared in the previous step, 200 mg, 0.430 mmol) in 6 mL of DCM was added 2 mL of TFA. After stirring at RT for 3 h, the mixture was treated with 20 mL of n-propanol and concentrated in vacuo. The residue was purified by flash chromatography on silica gel (4-6% MeOH/DCM) to afford 88.0 mg (61%) of the title compound as a white solid. $^1$H-NMR (CD$_3$OD; 400 MHz): δ 8.41 (d, 1H, J=8.6 Hz), 8.03 (s, 1H), 7.81 (dd, 1H, J=8.6, 2.3 Hz), 7.74 (d, 1H, J=2.3 Hz), 5.89 (m, 1H), 2.20-2.38 (m, 4H), 1.71-1.95 (m, 4H). Mass spectrum (ESI, m/z): Calcd. for C$_{18}$H$_{17}$N$_5$O$_2$, 336.1 (M+H), found 336.1.

EXAMPLE 27

4-Cyano-1H-imidazole-2-carboxylic acid [4-carbamoyl-2-(4,4-dimethyl-cyclohex-1-enyl)-phenyl]-amide

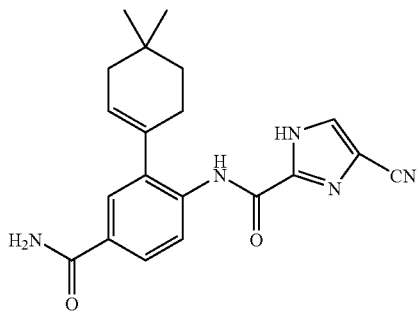

a) 4-Amino-3-(4,4-dimethyl-cyclohex-1-enyl)-benzamide

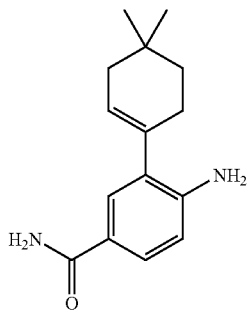

The title compound was prepared by the Suzuki coupling procedure of Example 11, step (e) using 4-amino-3-bromobenzamide (as prepared in Example 16, step (a), 62.4 mg, 0.289 mmol), and 2-(4,4-dimethyl-cyclohex-1-enyl)-4,4,5,5-tetramethyl-[1,3,2]dioxaborolane (75.0 mg, 0.318 mmol). Silica gel chromatography (0-2% MeOH/DCM) afforded the title compound (55 mg, 78%) as a faint yellow solid. Mass spectrum (ESI, m/z): Calcd. for C$_{15}$H$_{20}$N$_2$O, 245.2 (M+H), found 245.2.

b) 4-Cyano-1-(2-trimethylsilanyl-ethoxymethyl)-1H-imidazole-2-carboxylic acid [4-carbamoyl-2-(4,4-dimethyl-cyclohex-1-enyl)-phenyl]-amide

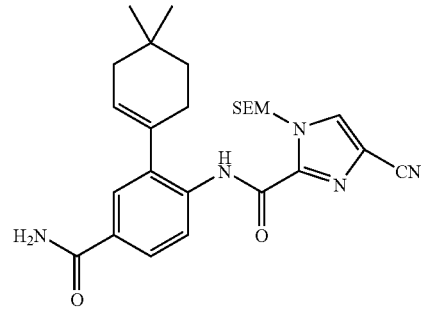

The title compound was prepared by the procedure of Example 11, step (f) using 4-amino-3-(4,4-dimethyl-cyclohex-1-enyl)-benzamide (as prepared in the previous step, 51.0 mg, 0.209 mmol) and potassium 4-cyano-1-(2-trimethylsilanyl-ethoxymethyl)-1H-imidazole-2-carboxylate (as prepared in Example 11, step (d), 70.2 mg, 0.230 mmol). Silica gel chromatography (0-2% MeOH/DCM) afforded the title compound (91 mg, 94%) as a white solid. Mass spectrum (ESI, m/z): Calcd. for C$_{26}$H$_{35}$N$_5$O$_3$Si, 494.3 (M+H), found 494.1.

c) 4-Cyano-1H-imidazole-2-carboxylic acid [4-carbamoyl-2-(4,4-dimethyl-cyclohex-1-enyl)-phenyl]-amide The title compound was prepared by the procedure of Example 24, step (b) using 4-cyano-1-(2-trimethylsilanyl-ethoxymethyl)-1H-imidazole-2-carboxylic acid [4-carbamoyl-2-(4,4-dimethyl-cyclohex-1-enyl)-phenyl]-amide (as prepared in the previous step, 100 mg, 0.203 mmol) and tetrabutylammonium fluoride (1.01 mL, 1.01 mmol, 1.0 M in THF). Silica gel chromatography (5% MeOH/DCM) afforded the title compound (14.1 mg, 19%) as a white solid. $^1$H-NMR (CD$_3$OD; 400 MHz): δ 8.42 (d, 1H, J=8.6 Hz), 8.00 (s, 1H), 7.81 (dd, 1H, J=8.6, 2.3 Hz), 7.75 (d, 1H, J=2.3 Hz), 5.81 (m, 1H), 2.28-2.40 (m, 2H), 2.04-2.17 (m, 2H), 1.63 (t, 2H, J=6.3 Hz), 1.11 (s, 6H). Mass spectrum (ESI, m/z): Calcd. for C$_{20}$H$_{21}$N$_5$O$_2$, 364.2 (M+H), found 364.1.

EXAMPLE 28

4-Cyano-1H-imidazole-2-carboxylic acid (4'-amino-3-cyclohex-1-enyl-biphenyl-4-yl)-amide, trifluoroacetic acid salt

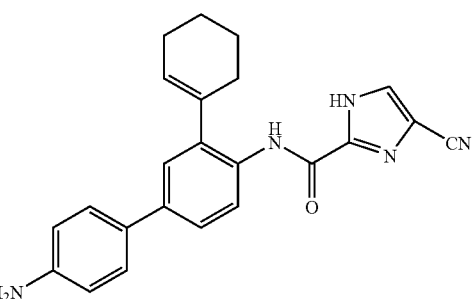

a) 4-Cyano-1-(2-trimethylsilanyl-ethoxymethyl)-1H-imidazole-2-carboxylic acid (4'-amino-3-cyclohex-1-enyl-biphenyl-4-yl)-amide

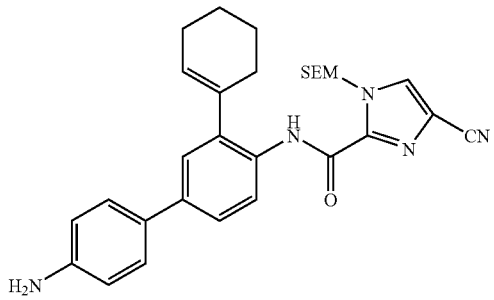

To a mixture of 4-cyano-1-(2-trimethylsilanyl-ethoxymethyl)-1H-imidazole-2-carboxylic acid (4-bromo-2-cyclohex-1-enyl-phenyl)-amide (as prepared in the Example 11, step (f), 30 mg, 0.060 mmol), 4-(4,4,5,5-tetramethyl-[1,3,2]dioxaborolan-2-yl)-phenylamine (14.4 mg, 0.066 mmol) and Pd(PPh$_3$)$_4$ (7 mg, 0.006 mmol) in 1 mL of 1,4-dioxane was added 2.0 M aq Na$_2$CO$_3$ solution (0.24 mL, 0.48 mmol). The resulting mixture was stirred at 80° C. for 3 h under Ar, and then cooled to RT. Treated with 50 µL of EtOAc, the mixture was washed with H$_2$O (2×20 mL), brine (10 mL) and dried (Na$_2$SO$_4$). Removal of the solvent under reduced pressure followed by flash chromatography of the residue on silica gel (20% EtOAc/hexane) gave 16 mg (85%) of the title compound as a white solid. $^1$H-NMR (CDCl$_3$; 400 MHz): δ 9.76 (s, 1H), 8.37 (d, 1H, J=8.6 Hz), 7.78 (s, 1H), 7.43-7.47 (m, 3H), 7.35 (d, 1H, J=2.1 Hz), 6.84 (d, 2H, J=8.5 Hz), 5.97 (s, 2H), 5.89 (m, 1H), 3.67 (t, 2H, J=8.2 Hz), 2.25-2.34 (m, 4H), 1.77-1.90 (m, 4H), 0.98 (t, 2H, J=8.2 Hz), 0.01 (s, 9H). Mass spectrum (ESI, m/z): Calcd. for C$_{29}$H$_{35}$N$_5$O$_2$Si, 514.3 (M+H), found 514.1.

b) 4-Cyano-1H-imidazole-2-carboxylic acid (4'-amino-3-cyclohex-1-enyl-biphenyl-4-yl)-amide, trifluoroacetic acid salt To a solution of 4-cyano-1-(2-trimethylsilanyl-ethoxymethyl)-1H-imidazole-2-carboxylic acid (4'-amino-3-cyclohex-1-enyl-biphenyl-4-yl)-amide (as prepared in the previous step, 25 mg, 0.049 mmol) in 1.5 mL of DCM was added 0.050 mL of EtOH followed by 0.50 mL of TFA. The resulting solution was stirred at RT for 3 h. Removal of the solvent under reduced pressure followed by flash chromatography of the residue on silica gel (3-5% MeOH/DCM) gave 17.2 mg (71%) of the title compound as a yellow solid. $^1$H-NMR (1:1 CDCl$_3$/CD$_3$OD; 400 MHz): δ 8.38 (d, 1H, J=8.4 Hz), 7.84 (s, 1H), 7.63 (d, 2H, J=8.6 Hz), 7.50 (dd, 1H, J=8.4, 2.3 Hz), 7.40 (d, 1H, J=2.3 Hz), 7.24 (d, 2H, J=8.6 Hz), 5.92 (m, 1H), 2.27-2.37 (m, 4H), 1.79-1.92 (m, 4H). Mass spectrum (ESI, m/z): Calcd. for C$_{23}$H$_{21}$N$_5$O, 384.2 (M+H), found 384.1.

EXAMPLE 29

4-Cyano-1H-imidazole-2-carboxylic acid (3-cyclohex-1-enyl-4'-methanesulfonylamino-biphenyl-4-yl)-amide

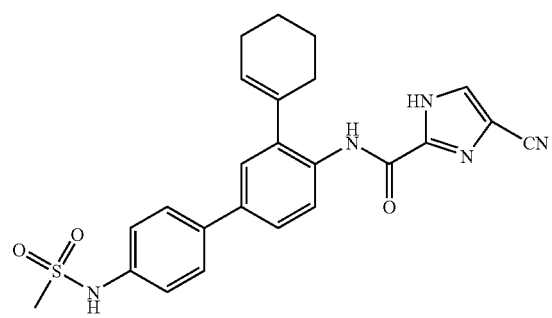

a) 4-Cyano-1-(2-trimethylsilanyl-ethoxymethyl)-1H-imidazole-2-carboxylic acid (3-cyclohex-1-enyl-4'-methanesulfonylamino-biphenyl-4-yl)-amide

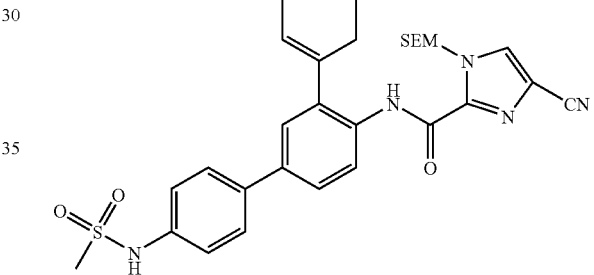

To a mixture of 4-cyano-1-(2-trimethylsilanyl-ethoxymethyl)-1H-imidazole-2-carboxylic acid (4'-amino-3-cyclohex-1-enyl-biphenyl-4-yl)-amide (as prepared in the Example 28, step (a), 28.1 mg, 0.0547 mmol) in 0.5 mL of DCM was added pyridine (113 µL, 0.16 mmol) followed by methanesulfonyl chloride (5.1 µL, 0.066 mmol). After stirring at RT for 16 h under Ar, the mixture was concentrated under reduced pressure. The residue was purified by flash chromatography on silica gel (2-4% EtOAc/DCM) to afford 31 mg (95%) of the title compound as a white solid. $^1$H-NMR (CDCl$_3$; 400 MHz): δ 9.79 (s, 1H), 8.42 (d, 1H, J=8.6 Hz), 7.79 (s, 1H), 7.58 (d, 2H, J=8.6 Hz), 7.48 (dd, 1H, J=8.6, 2.3 Hz), 7.37 (s, 1H), 7.29 (d, 2H, J=8.6 Hz), 6.64 (s, 1H), 5.97 (s, 2H), 5.91 (m, 1H), 3.68 (t, 2H, J=8.2 Hz), 3.05 (s, 3H), 2.24-2.38 (m, 4H), 1.75-1.93 (m, 4H), 0.99 (t, 2H, J=8.2 Hz), 0.01 (s, 9H). Mass spectrum (ESI, m/z): Calcd. for C$_{30}$H$_{37}$N$_5$O$_4$SSi, 592.2 (M+H), found 591.6.

b) 4-Cyano-1H-imidazole-2-carboxylic acid (3-cyclohex-1-enyl-4'-methanesulfonylamino-biphenyl-4-yl)-amide The title compound was prepared by the procedure of Example 11, step (g) using 4-cyano-1-(2-trimethylsilanyl-ethoxymethyl)-1H-imidazole-2-carboxylic acid (3-cyclohex-1-enyl-4'-methanesulfonylamino-biphenyl-4-yl)-amide (as prepared in the previous step, 29.5 mg, 0.0498 mmol). Silica gel chromatography (5-10% EtOAc/DCM) afforded the title compound (10.1 mg, 44%) as a white solid. $^1$H-NMR (CD$_3$OD; 400 MHz): δ 8.29 (d, 1H, J=8.6 Hz), 8.01 (s, 1H), 7.60 (d, 2H, J=8.6 Hz), 7.53 (dd, 1H, J=8.4, 2.0 Hz), 7.42 (d, 1H, J=2.0 Hz), 7.33 (d, 2H, J=8.6 Hz), 5.89 (m, 1H), 2.98 (s, 3H), 2.23-2.38 (m, 4H), 1.77-1.93 (m, 4H). Mass spectrum (ESI, m/z): Calcd. for C$_{24}$H$_{23}$N$_5$O$_3$S, 462.2 (M+H), found 461.9.

EXAMPLE 30

4-Cyano-1H-imidazole-2-carboxylic acid (3-cyclohex-1-enyl-biphenyl-4-yl)-amide

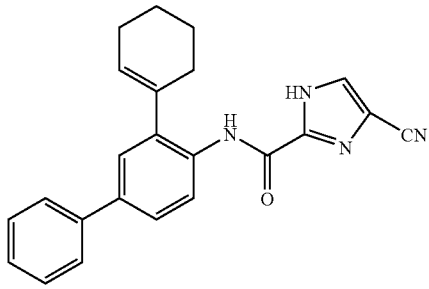

a) 4-Cyano-1-(2-trimethylsilanyl-ethoxymethyl)-1H-imidazole-2-carboxylic acid (3-cyclohex-1-enyl-biphenyl-4-yl)-amide

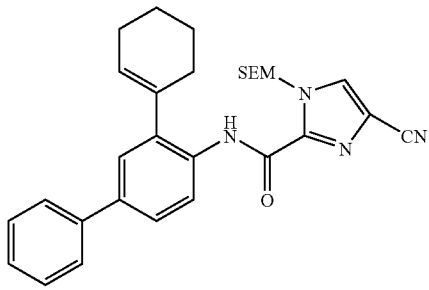

The title compound was prepared by the procedure of Example 28, step (a) using 4-cyano-1-(2-trimethylsilanyl-ethoxymethyl)-1H-imidazole-2-carboxylic acid (4-bromo-2-cyclohex-1-enyl-phenyl)-amide (as prepared in the Example 11, step (f), 19 mg, 0.038 mmol), and phenylboronic acid (5.1 mg, 0.042 mmol). Silica gel chromatography (5-10% EtOAc/hexane) afforded the title compound (16 mg, 85%) as a white solid. $^1$H-NMR (CDCl$_3$; 400 MHz): δ 9.79 (s, 1H), 8.42 (d, 1H, J=8.5 Hz), 7.78 (s, 1H), 7.59 (m, 2H), 7.52 (dd, 1H, J=8.5, 2.1 Hz), 7.44 (m, 2H), 7.41 (d, 1H, J=2.1 Hz), 7.33 (m, 1H), 5.97 (s, 2H), 5.91 (m, 1H), 3.67 (t, 2H, J=8.3 Hz), 2.26-2.36 (m, 4H), 1.75-1.93 (m, 4H), 0.98 (t, 2H, J=8.3 Hz), 0.01 (s, 9H). Mass spectrum (ESI, m/z): Calcd. for C$_{29}$H$_{34}$N$_4$O$_2$Si, 499.3 (M+H), found 498.8.

b) 4-Cyano-1H-imidazole-2-carboxylic acid (3-cyclohex-1-enyl-biphenyl-4-yl)-amide The title compound was prepared by the procedure of Example 11, step (g) using 4-cyano-1-(2-trimethylsilanyl-ethoxymethyl)-1H-imidazole-2-carboxylic acid (3-cyclohex-1-enyl-biphenyl-4-yl)-amide (as prepared in the previous step, 16 mg, 0.032 mmol). Silica gel chromatography (2-3% EtOAc/DCM) afforded the title compound (7.1 mg, 60%) as a white solid. $^1$H-NMR (1:1 CDCl$_3$/CD$_3$OD; 400 MHz): δ 8.36 (d, 1H, J=8.6 Hz), 7.88 (s, 1H), 7.59-7.62 (m, 2H), 7.54 (dd, 1H, J=8.6, 2.3 Hz), 7.42-7.46 (m, 3H), 7.34 (m, 1H), 5.92 (m, 1H), 2.29-2.37 (m, 4H), 1.79-1.94 (m, 4H). Mass spectrum (ESI, m/z): Calcd. for C$_{23}$H$_{20}$N$_4$O, 369.2 (M+H), found 369.1.

EXAMPLE 31

4-Cyano-1H-imidazole-2-carboxylic acid [5-acetyl-2-(4,4-dimethyl-cyclohex-1-enyl)-phenyl]-amide

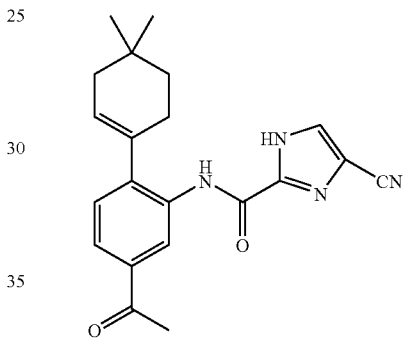

a) 1-[4-(4,4-Dimethyl-cyclohex-1-enyl)-3-nitro-phenyl]-ethanone

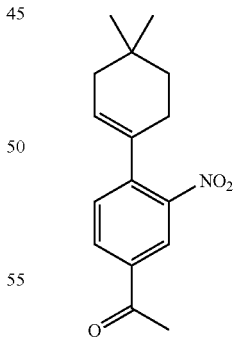

The title compound was prepared by the Suzuki coupling procedure of Example 11, step (e) using 1-(4-bromo-3-nitrophenyl)-ethanone (347 mg, 1.42 mmol), and 4,4-dimethylcyclohexen-1-ylboronic acid (254 mg, 1.65 mmol). Silica gel chromatography (5-15% EtOAc/hexane) afforded the title compound (385 mg, 99%) as a faint green oil. Mass spectrum (APCI, m/z): Calcd. for C$_{16}$H$_{19}$NO$_3$, 274.1 (M+H), found 274.0.

b) 1-[3-Amino-4-(4,4-dimethyl-cyclohex-1-enyl)-phenyl]-ethanone

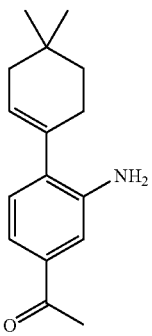

The title compound was prepared by the procedure of Example 19, using 1-[4-(4,4-dimethyl-cyclohex-1-enyl)-3-nitro-phenyl]-ethanone (as prepared in the previous step, 382 mg, 1.40 mmol), iron powder (391 mg, 7.00 mmol), and NH$_4$Cl (749 mg, 14.0 mmol). Silica gel chromatography (5-20% EtOAc/hexane) afforded the title compound (263 mg, 77%) as a faint yellow solid. Mass spectrum (ESI, m/z): Calcd. for C$_{16}$H$_{21}$NO, 244.2 (M+H), found 244.2.

c) 4-Cyano-1-(2-trimethylsilanyl-ethoxymethyl)-1H-imidazole-2-carboxylic acid [5-acetyl-2-(4,4-dimethyl-cyclohex-1-enyl)-phenyl]-amide

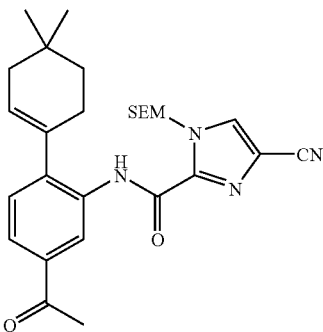

The title compound was prepared by the procedure of Example 11, step (f) using 1-[3-amino-4-(4,4-dimethyl-cyclohex-1-enyl)-phenyl]-ethanone (as prepared in the previous step, 243 mg, 1.00 mmol) and potassium 4-cyano-1-(2-trimethylsilanyl-ethoxymethyl)-1H-imidazole-2-carboxylate (as prepared in Example 11, step (d), 321 mg, 1.05 mmol). Silica gel chromatography (5-15% EtOAc/hexane) afforded the title compound (415 mg, 84%) as a white solid. Mass spectrum (ESI, m/z): Calcd. for C$_{27}$H$_{36}$N$_4$O$_3$Si, 493.3 (M+H), found 493.0.

d) 4-Cyano-1H-imidazole-2-carboxylic acid [5-acetyl-2-(4,4-dimethyl-cyclohex-1-enyl)-phenyl]-amide The title compound was prepared by the procedure of Example 11, step (g) using 4-cyano-1-(2-trimethylsilanyl-ethoxymethyl)-1H-imidazole-2-carboxylic acid [5-acetyl-2-(4,4-dimethyl-cyclohex-1-enyl)-phenyl]-amide (as prepared in the previous step, 200 mg, 0.406 mmol). Silica gel chromatography (5-15% EtOAc/DCM) afforded the title compound (134 mg, 91%) as a white solid. $^1$H-NMR (CDCl$_3$; 400 MHz): δ 12.85 (s, 1H), 9.75 (s, 1H), 9.13 (d, 1H, J=1.8 Hz), 8.18 (d, 1H, J=2.5 Hz), 7.75 (dd, 1H, J=8.1, 1.8 Hz), 7.32 (d, 1H, J=8.1 Hz), 5.86 (m, 1H), 2.67 (s, 3H), 2.28-2.35 (m, 2H), 2.08-2.19 (m, 2H), 1.62 (t, 2H, J=6.3 Hz), 1.13 (s, 6H). Mass spectrum (ESI, m/z): Calcd. for C$_{21}$H$_{22}$N$_4$O$_2$, 363.2 (M+H), found 363.2.

EXAMPLE 32

4-Cyano-1H-imidazole-2-carboxylic acid [2-(4,4-dimethyl-cyclohex-1-enyl)-5-(1-hydroxy-1-methyl-ethyl)-phenyl]-amide

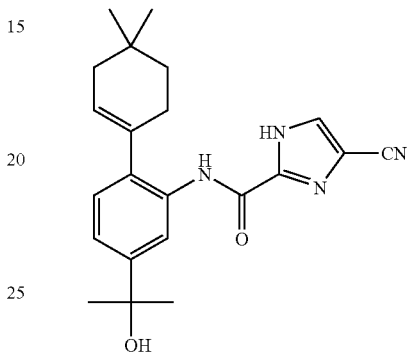

To a solution of 4-cyano-1H-imidazole-2-carboxylic acid [5-acetyl-2-(4,4-dimethyl-cyclohex-1-enyl)-phenyl]-amide (as prepared in Example 31, step (d), 30.0 mg, 0.0828 mmol) in 2 mL of THF at −78° C. under Ar was added methyl magnesium chloride (58 μL, 0.17 mmol, 3.0 M in THF). The resulting mixture was warmed to RT and stirred for 0.5 h. Treated with 10 mL of saturated NH$_4$Cl aqueous solution followed by 10 mL of brine, the mixture was extracted with EtOAc (2×20 mL). The combined organic layers were dried with Na$_2$SO$_4$. The solvent was evaporated under reduced pressure and the residue was purified by flash chromatography on silica gel (2-3% MeOH/DCM) to give 29.0 mg (93%) of the title compound as a white solid. $^1$H-NMR (DMSO-d$_6$; 400 MHz): δ 14.22 (s, 1H), 9.76 (s, 1H), 8.32 (s, 1H), 8.12 (d, 1H, J=1.8 Hz), 7.25 (dd, 1H, J=8.1, 1.8 Hz), 7.14 (d, 1H, J=8.1 Hz), 5.65 (m, 1H), 2.16-2.29 (m, 2H), 1.87-1.98 (m, 2H), 1.47 (t, 2H, J=6.2 Hz), 1.43 (s, 6H), 0.99 (s, 6H). Mass spectrum (ESI, m/z): Calcd. for C$_{22}$H$_{26}$N$_4$O$_2$, 379.2 (M+H), found 379.0.

EXAMPLE 33

4-Cyano-1H-imidazole-2-carboxylic acid [4-bromo-2-(4,4-dimethyl-cyclohex-1-enyl)-phenyl]-amide

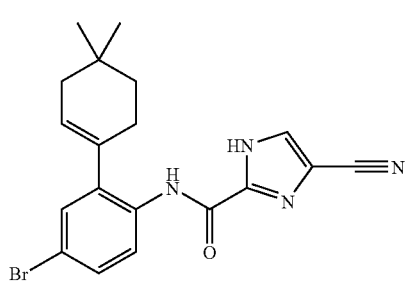

a) 4-Bromo-2-(4,4-dimethyl-cyclohex-1-enyl)-phenylamine

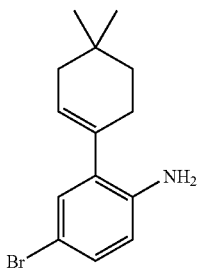

A mixture of 4-bromo-2-iodo-phenylamine (873 mg, 2.93 mmol), 4,4-dimethylcyclohexen-1-ylboronic acid (496 mg, 3.22 mmol), Pd(PPh$_3$)$_4$ (169 mg, 0.147 mmol) and 2.0 M aq Na$_2$CO$_3$ (11.7 mL, 23.4 mmol) in 20 mL of 1,4-dioxane was stirred at 80° C. for 12 h under Ar. After cooling to RT, the reaction was treated with EtOAc (50 mL) and washed with H$_2$O (25 mL) and brine (20 mL). The organic layer was dried (Na$_2$SO$_4$) and concentrated in vacuo. The residue was purified by flash chromatography on silica gel (5% EtOAc/hexane) to afford 770 mg (91%) of the title compound as a colorless oil. Mass spectrum (ESI, m/z): Calcd. for C$_{14}$H$_{18}$BrN, 280.1 (M+H), found 280.1.

b) 4-Cyano-1-(2-trimethylsilanyl-ethoxymethyl)-1H-imidazole-2-carboxylic acid [4-bromo-2-(4,4-dimethyl-cyclohex-1-enyl)-phenyl]-amide

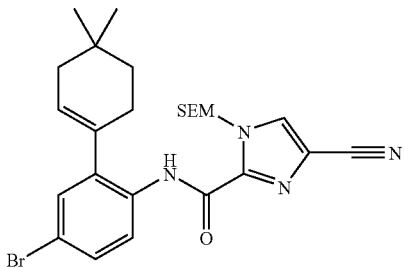

To a mixture of 4-bromo-2-(4,4-dimethyl-cyclohex-1-enyl)-phenylamine (as prepared in the previous step, 770 mg, 2.75 mmol), potassium 4-cyano-1-(2-trimethylsilanyl-ethoxymethyl)-1H-imidazole-2-carboxylate (as prepared in Example 11, step (d), 840 mg, 2.75 mmol) and PyBroP (1.28 g, 2.75 mmol) in 20 mL of DMF was added DIEA (1.44 mL, 8.25 mmol). The resulting mixture was stirred at RT for 16 h under Ar. Treated with 80 mL of EtOAc, the mixture was washed with H$_2$O (2×20 mL), brine (20 mL) and dried (Na$_2$SO$_4$). Removal of the solvent under reduced pressure followed by flash chromatography of the residue on silica gel (5-10% EtOAc/hexane) gave 1.28 g (88%) of the title compound as a white solid. Mass spectrum (ESI, m/z): Calcd. for C$_{25}$H$_{33}$BrN$_4$O$_2$Si, 529.2 (M+H), found 528.9.

c) 4-Cyano-1H-imidazole-2-carboxylic acid [4-bromo-2-(4,4-dimethyl-cyclohex-1-enyl)-phenyl]-amide The title compound was prepared by the experimental procedure of Example 11, step (g) using 4-cyano-1-(2-trimethylsilanyl-ethoxymethyl)-1H-imidazole-2-carboxylic acid [4-bromo-2-(4,4-dimethyl-cyclohex-1-enyl)-phenyl]-amide (as prepared in the previous step, 350 mg, 0.661 mmol). The title compound (253 mg, 96%) was obtained as a white solid. $^1$H-NMR (CDCl$_3$; 400 MHz): δ 8.19 (d, 2H, J=8.8 Hz), 7.50 (d, 2H, J=8.8 Hz), 6.23 (m, 1H), 4.12 (m, 2H), 3.66 (m, 2H), 2.54 (m, 2H), 1.49 (s, 9H). Mass spectrum (ESI, m/z): Calcd. for C$_{19}$H$_{19}$BrN$_4$O, 399.1 (M+H), found 399.1.

EXAMPLE 34

4-Cyano-1H-imidazole-2-carboxylic acid [2-(4,4-dimethyl-cyclohex-1-enyl)-4-(1-hydroxy-1-methyl-ethyl)-phenyl]-amide

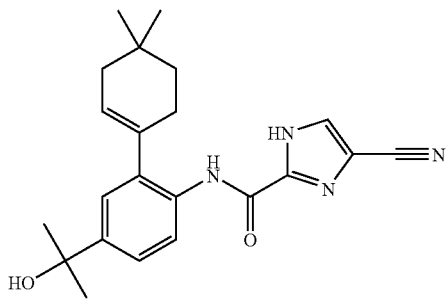

The title compound was prepared by the experimental procedure of Example 12 using 4-cyano-1H-imidazole-2-carboxylic acid [4-bromo-2-(4,4-dimethyl-cyclohex-1-enyl)-phenyl]-amide (as prepared in the previous step, 200 mg, 0.501 mmol). Flash chromatography on silica gel (1-4% MeOH/DCM) afforded the title compound (101 mg, 53%) as a white solid. $^1$H-NMR (CDCl$_3$; 400 MHz): δ 12.52 (s, 1H), 9.68 (s, 1H), 8.29 (d, 1H, J=8.6 Hz), 7.72 (d, 1H, J=2.3 Hz), 7.42 (dd, 1H, J=8.6, 2.2 Hz), 7.35 (d, 1H, J=2.2 Hz), 5.78 (m, 1H), 2.64 (s, 1H, OH), 2.30 (m, 2H), 2.11 (m, 2H), 1.62 (s, 6H), 1.59 (t, 2H, J=6.5 Hz), 1.11 (s, 6H). Mass spectrum (ESI, m/z): Calcd. for C$_{22}$H$_{26}$N$_4$O$_2$, 379.2 (M+H), found 379.3.

EXAMPLE 35

4-Cyano-1H-imidazole-2-carboxylic acid [2-cyclohex-1-enyl-4-(2-hydroxy-2-methyl-propyl)-phenyl]-amide

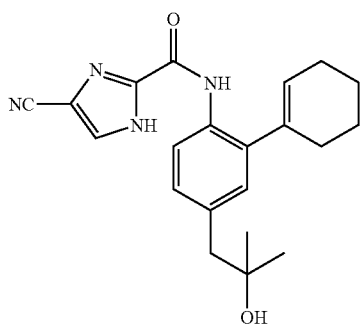

To a solution of 4-cyano-1H-imidazole-2-carboxylic acid (4-bromo-2-cyclohex-1-enyl-phenyl)-amide (prepared in Example 11, step (g)) (0.10 g, 0.27 mmol) in 1.5 mL of THF at −40° C. was added 0.15 mL of i-PrMgCl (0.30 mmol, 2 M solution in THF) and the solution was stirred at this temperature for 15 min. The mixture was then cooled to −78° C. and 2,2-dimethyl-oxirane (0.12 mL, 1.3 mmol) was added followed by boron trifluoride etherate (0.044 mL, 0.35 mmol) and t-BuLi (0.41 mL, 0.69 mmol, 1.7 M solution in pentane). After stirring for 30 min at −78° C. the mixture was quenched with satd NH$_4$Cl (10 mL), extracted with EtOAc (2×10 mL) and the organic layer was dried over Na$_2$SO$_4$ and concentrated. The title compound was eluted from a 20-g SPE column with 50% EtOAc/hexanes to give 0.015 g (15%) of a white solid: $^1$H-NMR (DMSO-d6, 400 MHz): δ 14.25 (s, 1H), 9.71 (s, 1H), 8.33 (s, 1H), 7.84 (d, J=8.2 Hz, 1H), 7.14 (dd, J=8.2, 1.9 Hz, 1H), 7.06 (d, J=1.9 Hz, 1H), 5.74 (s, 1H), 4.63 (t, J=5.2 Hz, 1H), 3.61 (m, 2H), 2.70 (t, J=7.0 Hz, 2H), 2.23-2.11 (m, 4H), 1.76-1.62 (m, 4H). Mass spectrum (ESI, m/z): Calcd. for C$_{21}$H$_{24}$N$_4$O$_2$, 365.2 (M+H), found 365.1.

EXAMPLE 36

4-Cyano-1H-imidazole-2-carboxylic acid [2-(4,4-dimethyl-cyclohex-1-enyl)-4-methanesulfonyl-phenyl]-amide

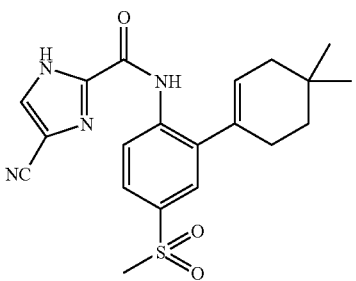

a) 4-Cyano-1H-imidazole-2-carboxylic acid [2-(4,4-dimethyl-cyclohex-1-enyl)-4-methylsulfanyl-phenyl]-amide

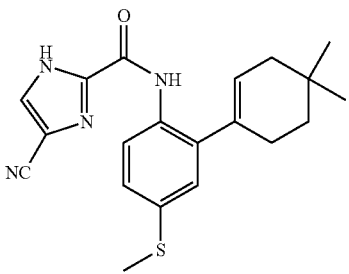

The title compound was prepared according to the general procedure for Example 12 using dimethyldisulfide as the electrophile. Mass spectrum (ESI, m/z): Calcd. for C$_{20}$H$_{22}$N$_4$OS, 367.1 (M+H), found 367.0.

b) 4-Cyano-1H-imidazole-2-carboxylic acid [2-(4,4-dimethyl-cyclohex-1-enyl)-4-methanesulfonyl-phenyl]-amide To a solution of 4-cyano-1H-imidazole-2-carboxylic acid [2-(4,4-dimethyl-cyclohex-1-enyl)-4-methylsulfanyl-phenyl]-amide (30 mg, 0.082 mmol) in 2 mL of DCM was added m-chloroperoxbenzoic acid (77%, 55 mg, 0.25 mmol) and the mixture stirred for 3 h at RT. The reaction was diluted with 15 mL of EtOAc and washed with NaHCO$_3$ (2×15 mL) and brine (15 mL), dried over Na$_2$SO$_4$ and concentrated. The title compound was purified by elution from a 5-g SPE column with 50% EtOAc/hexanes to give 23 mg (70%) of a white solid. $^1$H NMR (CDCl$_3$, 400 MHz): δ 11.18 (br s, 1H), 9.70 (br s, 1H), 8.62 (d, J=8.7 Hz, 1H), 7.88 (dd, J=2.2, 8.7 Hz, 1H), 7.77 (d, J=2.2 Hz, 1H), 7.76 (s, 1H), 5.86 (m, 1H), 3.10 (s, 3H), 2.32 (m, 2H), 2.12 (m, 2H), 1.62 (m, 2H), 1.12 (s, 6H). Mass spectrum (ESI, m/z): Calcd. for C$_{20}$H$_{22}$N$_4$O$_3$S, 399.1 (M+H), found 399.0.

EXAMPLE 37

5-Cyano-1H-imidazole-2-carboxylic acid [2-cyclohex-1-enyl-4-(2-hydroxy-ethyl)-phenyl]-amide

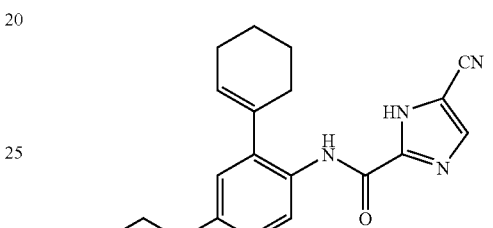

a) 2-(4-Amino-3-bromo-phenyl)-ethanol

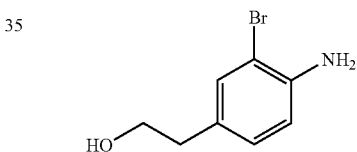

To a solution of 2-(4-amino-phenyl)-ethanol (5.10 g, 37.2 mmol) in 37 mL of DMF was added NBS (6.60 g, 37.1 mmol) and the mixture stirred overnight at RT. The reaction was diluted with 100 mL of water and extracted with EtOAc (3×100 mL). The organic layer was washed with brine (200 mL) and dried over Na$_2$SO$_4$. The title compound was purified by silica gel flash chromatography eluting with 50% EtOAc/hexanes to give 5.10 g (64%) of a white solid. Mass spectrum (ESI, m/z): Calcd. for C$_8$H$_{10}$BrNO, 216.0 (M+H), found 216.1.

b) 2-(4-Amino-3-cyclohex-1-enyl-phenyl)-ethanol

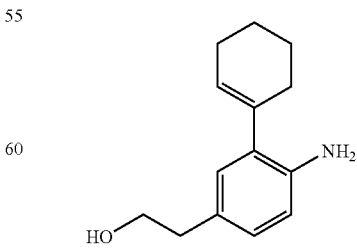

The title compound was prepared by Suzuki coupling of 2-(4-amino-phenyl)-ethanol (prepared in the previous step) and 1-cyclohexen-1-yl-boronic acid according to the procedure of Example 44, step (b). Mass spectrum (ESI, m/z): Calcd. for $C_{14}H_{19}NO$, 218.1 (M+H), found 218.1.

c) 5-Cyano-1H-imidazole-2-carboxylic acid [2-cyclohex-1-enyl-4-(2-hydroxy-ethyl)-phenyl]-amide The title compound was prepared by coupling 2-(4-amino-3-cyclohex-1-enyl-phenyl)-ethanol (prepared in the previous step) and 4-cyano-1-(2-trimethylsilanyl-ethoxymethyl)-1H-imidazole-2-carboxylate potassium salt (prepared in Example 11, step (d)) according to the procedure in Example 42, step (c) followed by SEM deprotection according to the procedure in Example 11, step (g). $^1$H-NMR (CD$_3$OD, 400 MHz): δ 8.10 (d, J=8.3 Hz, 1H), 8.02 (s, 1H), 7.17 (dd, J=8.3, 1.9 Hz, 1H), 7.08 (d, J=1.9 Hz, 1H), 5.82 (s, 1H), 3.77 (t, J=7.0 Hz, 2H), 2.82 (t, J=7.0 Hz, 2H), 2.31-2.25 (m, 4H), 1.90-1.76 (m, 4H). Mass spectrum (ESI, m/z): Calcd. for $C_{19}H_{20}N_4O_2$, 337.2 (M+H), found 337.1.

EXAMPLE 38

5-Cyano-1H-imidazole-2-carboxylic acid [2-(4,4-dimethyl-cyclohex-1-enyl)-4-(2-hydroxy-ethyl)-phenyl]-amide

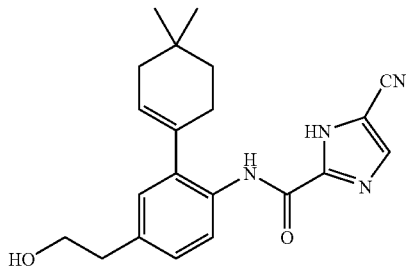

This compound prepared according to the procedures in Example 37 substituting 4,4-dimethylcyclohexen-1-ylboronic acid for 1-cyclohexen-1-yl-boronic acid in step (b). $^1$H-NMR (CDCl$_3$, 400 MHz): δ 12.62 (s, 1H), 9.65 (s, 1H), 8.26 (d, J=8.3 Hz, 1H), 7.68 (s, 1H), 7.19 (dd, J=8.3, 1.8 Hz, 1H), 7.07 (d, J=1.8 Hz, 1H), 5.75 (s, 1H), 3.92 (t, J=6.4 Hz, 2H), 2.88 (t, J=6.4 Hz, 2H), 2.30-2.23 (m, 2H), 2.11-2.06 (m, 2H), 1.57 (t, J=6.3 Hz, 2H), 1.09 (s, 6H). Mass spectrum (ESI, m/z): Calcd. for $C_{21}H_{24}N_4O_2$, 365.2 (M+H), found 365.0.

EXAMPLE 39

5-Cyano-1H-imidazole-2-carboxylic acid (6-cyclohex-1-enyl-benzo[1,3]dioxol-5-yl)-amide

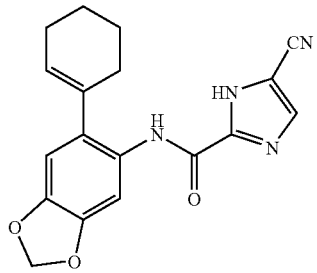

a) 6-Cyclohex-1-enyl-benzo[1,3]dioxol-5-ylamine

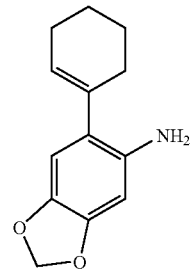

The title compound was prepared by Suzuki coupling of 6-bromo-benzo[1,3]dioxol-5-ylamine (Bioorganic & Medicinal Chemistry (2002), 10(11), 3395-3400) and cyclohexen-1-ylboronic acid according the procedure Example 44, step (g). Mass spectrum (ESI, m/z): Calcd. for $C_{13}H_{15}NO_2$, 218.1 (M+H), found 218.1.

b) 5-Cyano-1H-imidazole-2-carboxylic acid (6-cyclohex-1-enyl-benzo[1,3]dioxol-5-yl)-amide The title compound was prepared by coupling 6-cyclohex-1-enyl-benzo[1,3]dioxol-5-ylamine (prepared in the previous step) and 4-cyano-1-(2-trimethylsilanyl-ethoxymethyl)-1H-imidazole-2-carboxylate potassium salt (prepared in Example 11, step (d)) according to the procedure in Example 42, step (c) followed by SEM deprotection according to the procedure in Example 11, step (g). $^1$H-NMR (DMSO-d$_6$, 400 MHz): δ 14.23 (s, 1H), 9.67 (s, 1H), 8.31 (s, 1H), 7.48 (s, 1H), 6.78 (s, 1H), 6.01 (s, 2H), 5.69 (s, 1H), 2.20-2.05 (m, 4H), 1.71-1.57 (m, 4H). Mass spectrum (ESI, m/z): Calcd. for $C_{18}H_{16}N_4O_3$, 337.1 (M+H), found 337.0.

EXAMPLE 40

5-Cyano-1H-imidazole-2-carboxylic acid [2-(3-methyl-3H-imidazol-4-yl)-phenyl]-amide trifluoroacetic acid salt

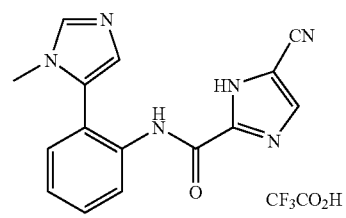

a) 4-Cyano-1-(2-trimethylsilanyl-ethoxymethyl)-1H-imidazole-2-carboxylic acid [2-(4,4,5,5-tetramethyl-[1,3,2]dioxaborolan-2-yl)-phenyl]-amide

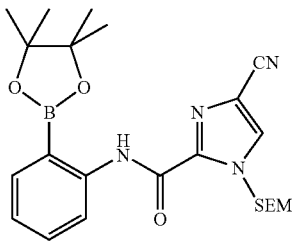

The title compound was prepared by coupling 2-aminobenzeneboronic acid pinacol ester and 4-cyano-1-(2-trimethylsilanyl-ethoxymethyl)-1H-imidazole-2-carboxylate potassium salt (prepared in Example 11, step (d)) according to the procedure in Example 32, step (c). Mass spectrum (ESI, m/z): Calcd. for $C_{23}H_{33}BN_4O_4Si$, 469.2 (M+H), found 468.9.

b) 5-Cyano-1H-imidazole-2-carboxylic acid [2-(3-methyl-3H-imidazol-4-yl)-phenyl]-amide trifluoroacetic acid salt The title compound was prepared by Suzuki coupling of 4-cyano-1-(2-trimethylsilanyl-ethoxymethyl)-1H-imidazole-2-carboxylic acid [2-(4,4,5,5-tetramethyl-[1,3,2]dioxaborolan-2-yl)-phenyl]-amide (prepared in the previous step) and 5-iodo-1-methyl-1H-imidazole according to the procedure in Example 44, step (b), followed by SEM deprotection according to the procedure in Example 11, step (g). $^1$H-NMR (DMSO-d$_6$, 400 MHz): δ 14.20 (s, 1H), 10.44 (s, 1H), 9.09 (s, 1H), 8.32 (s, 1H), 7.76 (d, J=7.6 Hz, 1H), 7.64 (d, J=1.3 Hz, 1H), 7.63-7.55 (m, 2H), 7.44 (m, 1H), 3.69 (s, 3H). Mass spectrum (ESI, m/z): Calcd. for $C_{15}H_{12}N_6O$, 293.1 (M+H), found 293.0.

EXAMPLE 41

4-Cyano-1H-imidazole-2-carboxylic acid [2-(4-methyl-piperidin-1-yl)-phenyl]-amide trifluoroacetic acid salt

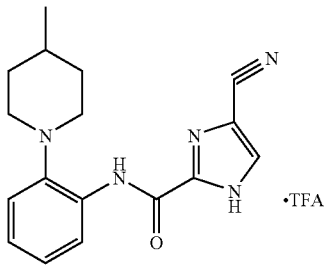

a) 4-Cyano-1-(2-trimethylsilanyl-ethoxymethyl)-1H-imidazole-2-carboxylic acid [2-(4-methyl-piperidin-1-yl)-phenyl]-amide

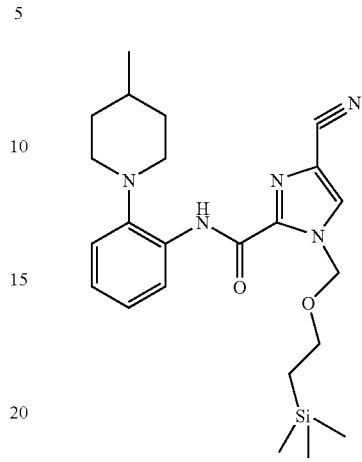

A solution of 1.00 g (7.09 mmol) of 1-fluoro-2-nitro-benzene in DMF (5 mL) was treated with 2.52 mL (21.3 mmol) of 4-methyl-piperidine and heated to 60° C. for 15 min. The mixture was diluted with EtOAc (50 mL) and washed with water (6×30 mL). The organic layer was dried (MgSO$_4$) and concentrated in vacuo. A 250 mg (1.14 mmol) portion of the residue was taken up in THF (5 mL) and treated with 15 mg of 10% Pd/C (Degussa type E101-NE/W, Aldrich, 50% by weight water) under H$_2$ (1 atm). When this reaction was complete, the mixture was filtered through Celite directly into a suspension of 24.5 mg (0.147 mmol) of PyBroP, 30.0 mg (0.0980 mmol) of 4-cyano-1-(2-trimethylsilanyl-ethoxymethyl)-1H-imidazole-2-carboxylate potassium salt (as prepared in Example 11, step (d)), and 51.0 μL (0.295 mmol) of DIEA in THF (5 mL). The mixture was flushed with Ar and stirred at RT for 16 h. An additional 24.5 mg (0.147 mmol) of PyBroP, 30.0 mg (0.0980 mmol) of 4-cyano-1-(2-trimethyl-silanyl-ethoxymethyl)-1H-imidazole-2-carboxylate potassium salt (as prepared in Example 11, step (d)), and 51.0 μL (0.295 mmol) of DIEA were added, and the mixture stirred for 2 h. The mixture was diluted with EtOAc (10 mL), washed with water (1×10 mL) and saturated aqueous NaHCO$_3$ (1×10 mL), dried (MgSO$_4$), and concentrated in vacuo to afford 153 mg (30%) of the title compound as a white solid: Mass spectrum (ESI, m/z): Calcd. for $C_{23}H_{33}N_5Si$, 440.2 (M+H), found 440.0.

b) 4-Cyano-1H-imidazole-2-carboxylic acid [2-(4-methyl-piperidin-1-yl)-phenyl]-amide trifluoroacetic acid salt A solution of 153 mg (0.348 mmol) of 4-cyano-1-(2-trimethylsilanyl-ethoxymethyl)-1H-imidazole-2-carboxylic acid [2-(4-methyl-piperidin-1-yl)-phenyl]-amide (as prepared in the previous step) in CH$_2$Cl$_2$ (5 mL) was treated with EtOH (1 drop) and TFA (1 mL), and the mixture was warmed to 40° C. for 2 h and left at RT for 2 days. The mixture was concentrated to dryness, taken up in CH$_2$Cl$_2$ (5 mL), and treated with EtOH (1 drop) and TFA (1.00 mL) at RT for 7 h. The mixture was concentrated in vacuo. The residue was taken up in MeOH (2.5 mL) and a 10% solution of acetonitrile in water (7.5 mL) to form a suspension. The solid was filtered and triturated with a minimum amount of acetone to afford 50.7 mg (34%) of the title compound as a white solid: $^1$H-NMR (CD$_3$OD;

400 MHz): δ 8.35-8.32 (m, 1H), 8.03 (s, 1H), 7.29-7.26 (m, 1H), 7.15-7.12 (m, 2H), 3.09-2.99 (m, 2H), 2.81-2.74 (m, 2H), 1.85-1.80 (m, 2H), 1.72-1.56 (m, 3H), 1.09 (d, 3H, J=6.0 Hz). Mass spectrum (ESI, m/z): Calcd. for $C_{17}H_{19}N_5O$, 310.2 (M+H), found 310.0.

EXAMPLE 42

4-Cyano-1H-imidazole-2-carboxylic acid [2-(4,4-dimethyl-cyclohex-1-enyl)-pyridin-3-yl]-amide trifluoroacetic acid salt

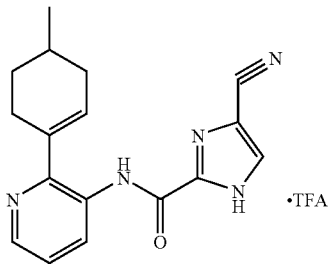

a) 2-(4,4-Dimethyl-cyclohex-1-enyl)-3-nitro-pyridine

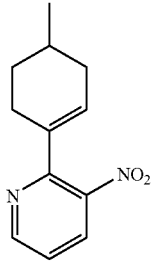

A solution of 894 mg (3.78 mmol) of 4,4-dimethyl-cyclohex-1-enylboronic acid and 0.500 g (3.15 mmol) of 2-chloro-3-nitro-pyridine in toluene (20 mL) and EtOH (10 mL) was treated with 12.6 mL (25.2 mmol) of 2.0 M aqueous $Na_2CO_3$. The mixture was degassed via sonication, placed under Ar, treated with 364 mg (0.315 mmol) of $Pd(PPh_3)_4$, and heated to 80° C. for 2 h. The mixture was cooled to RT, diluted with EtOAc (50 mL), and washed with saturated aqueous $NaHCO_3$ (1×40 mL) and water (1×40 mL). The aqueous layer was extracted with EtOAc (40 mL), and the combined organic layers were dried ($MgSO_4$) and concentrated in vacuo. Silica gel chromatography of the residue with $CH_2Cl_2$ afforded 446 mg (61%) of the title compound as a yellow solid: $^1$H-NMR ($CDCl_3$; 400 MHz): δ 8.73 (dd, 1H, J=4.8, 1.6 Hz), 8.02 (dd, 1H, J=8.4, 1.6 Hz), 7.32 (m, 1H), 5.83 (sept, 1H, J=2.0 Hz), 2.50-2.44 (m, 2H), 1.98-1.93 (m, 2H), 1.56 (t, 2H, J=6.0 Hz), 1.00 (s, 6H).

b) 2-(4,4-Dimethyl-cyclohex-1-enyl)-pyridin-3-ylamine

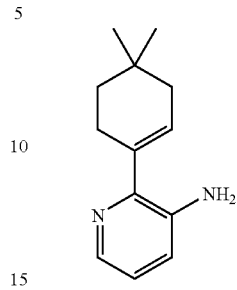

A solution of 90.0 mg (0.387 mmol) of 2-(4,4-dimethyl-cyclohex-1-enyl)-3-nitro-pyridine (as prepared in the previous step) in EtOH (10 mL) and water (5 mL) was treated with AcOH (3 drops) and 121 mg (2.17 mmol) of Fe powder then heated to 70° C. for 1.5 h. The mixture was quenched with saturated aqueous $NaHCO_3$ (20 mL) and extracted with $CH_2Cl_2$ (3×40 mL). The combined organic layers were dried ($MgSO_4$) and concentrated in vacuo to afford 80.0 mg (100%) of the title product as a tan glass: Mass spectrum (ESI, m/z): Calcd. for $C_{13}H_{18}N_2$, 203.2 (M+H), found 203.2.

c) 4-Cyano-1-(2-trimethylsilanyl-ethoxymethyl)-1H-imidazole-2-carboxylic acid [2-(4,4-dimethyl-cyclohex-1-enyl)-pyridin-3-yl]-amide

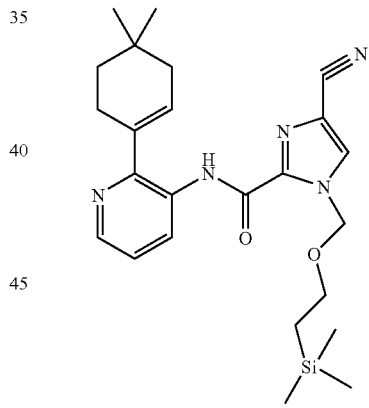

A solution of 80.0 mg (0.395 mmol) of 2-(4,4-dimethyl-cyclohex-1-enyl)-pyridin-3-ylamine (as prepared in the previous step) in $CH_2Cl_2$ (10 mL) was treated with 277 mg (0.593 mmol) of PyBroP, 133 mg (0.435 mmol) of 4-cyano-1-(2-trimethylsilanyl-ethoxymethyl)-1H-imidazole-2-carboxylate potassium salt (as prepared in Example 11, step (d)), and 207 μL (1.19 mmol) of DIEA. The mixture was stirred at RT for 17 h, diluted with $CH_2Cl_2$ (20 mL) and washed with water (1×10 mL). The aqueous layer was extracted with $CH_2Cl_2$ (1×10 mL), and the combined organic layers were dried ($MgSO_4$) and concentrated in vacuo. Silica gel chromatography of the residue on a 10-g Isolute SPE column with 25% EtOAc-hexane afforded 95 mg (53%) of the title compound as a white solid: $^1$H-NMR ($CDCl_3$; 400 MHz): δ 9.92 (br s, 1H), 8.72 (dd, 1H, J=8.0, 1.6 Hz), 8.37 (dd, 1H, J=4.4, 1.6 Hz), 7.77 (s, 1H), 7.23-7.18 (m, 1H), 6.00-5.94 (m, 1H), 5.93 (s, 2H), 3.70-3.63 (m, 2H), 2.51-2.43 (m, 2H), 2.18-2.11 (m, 2H), 1.61 (t, 2H, J=6.4 Hz), 1.12 (s, 6H), 1.00-0.94 (m, 2H), 0.00 (s, 9H).

d) 4-Cyano-1H-imidazole-2-carboxylic acid [2-(4,4-dimethyl-cyclohex-1-enyl)-pyridin-3-yl]-amide trifluoroacetic acid salt A solution of 95.0 mg (0.210 mmol) of 4-cyano-1-(2-trimethylsilanyl-ethoxymethyl)-1H-imidazole-2-carboxylic acid [2-(4,4-dimethyl-cyclohex-1-enyl)-pyridin-3-yl]-amide (as prepared in the previous step) in $CH_2Cl_2$ (15 mL) was treated with MeOH (1 drop) and TFA (1 mL). The mixture was stirred at RT for 2 days, and the solvents were evaporated in vacuo. Silica gel chromatography of the residue on a 20-g Isolute SPE column with 25% EtOAc-hexane and RP-HPLC (C18) with 10-80% $CH_3CN$ in 0.1% $TFA/H_2O$ over 30 min afforded 36.0 mg (39%) of the title compound as a white solid: $^1$H-NMR ($CD_3OD$; 400 MHz): δ 9.02 (dd, 1H, J=8.4, 1.6 Hz), 8.44 (dd, 1H, J=5.2, 1.6 Hz), 8.06 (s, 1H), 7.76-7.71 (m, 1H), 6.22 (sept, 1H, J=2.0 Hz), 2.50-2.43 (m, 2H), 2.18-2.13 (m, 2H), 1.65 (t, 2H, J=6.4 Hz), 1.11 (s, 6H). Mass spectrum (ESI, m/z): Calcd. for $C_{18}H_{19}N_5O$, 322.1 (M+H), found 322.1.

EXAMPLE 43

4-Cyano-1H-imidazole-2-carboxylic acid (2-cyclohex-1-enyl-pyridin-3-yl)-amide trifluoroacetic acid salt

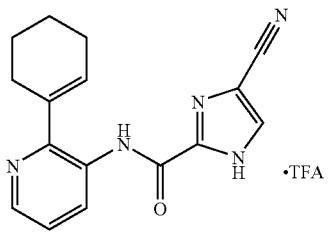

a) 2-Cyclohex-1-enyl-3-nitro-pyridine

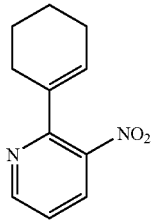

A solution of 1.00 g (6.31 mmol) of 2-chloro-3-nitro-pyridine in toluene (50 mL) and EtOH (25 mL) was treated with 1.58 g (7.57 mmol) of 2-cyclohex-1-enyl-4,4,5,5-tetramethyl-[1,3,2]dioxaborolane and 25.2 mL (50.4 mmol) of 2.0 M aqueous $Na_2CO_3$. The mixture was degassed via sonication, placed under Ar, treated with 729 mg (0.631 mmol) of $Pd(PPh_3)_4$, and heated to 80° C. for 16 h. The mixture was diluted with EtOAc (100 mL) and washed with water (1×75 mL). The organic layer was dried ($MgSO_4$) and concentrated in vacuo. Silica gel chromatography of the residue on a 50-g Varian MegaBond Elut SPE column with $CH_2Cl_2$ afforded 497 mg (39%) of the title compound as a yellow solid: $^1$H-NMR ($CD_3OD$; 400 MHz): δ 8.70 (dd, 1H, J=5.2, 1.6 Hz), 8.20 (dd, 1H, J=8.4, 1.6 Hz), 7.51-7.46 (m, 1H), 5.81 (sept, 1H, J=2.4 Hz), 2.44-2.37 (m, 2H), 2.19-2.12 (m, 2H), 1.84-1.76 (m, 2H), 1.74-1.66 (m, 2H).

b) 2-Cyclohex-1-enyl-pyridin-3-ylamine

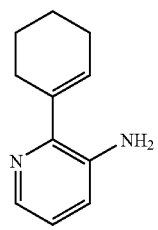

A solution of 497.0 mg (2.43 mmol) of 2-cyclohex-1-enyl-3-nitro-pyridine (as prepared in the previous step) in EtOH (10 mL) and water (5 mL) was treated with AcOH (6 drops) and 679 mg (12.2 mmol) of Fe powder, and heated to 75° C. for 19 h. The mixture was diluted with EtOAc (30 mL) and washed with water (1×20 mL). The organic layer was dried ($MgSO_4$) and concentrated in vacuo to afford 365 mg (86%) of the title compound as a pale yellow solid: Mass spectrum (ESI, m/z): Calcd. for $C_{11}H_{14}N_2$, 175.1 (M+H), found 175.2.

c) 4-Cyano-1-(2-trimethylsilanyl-ethoxymethyl)-1H-imidazole-2-carboxylic acid (2-cyclohex-1-enyl-pyridin-3-yl)-amide

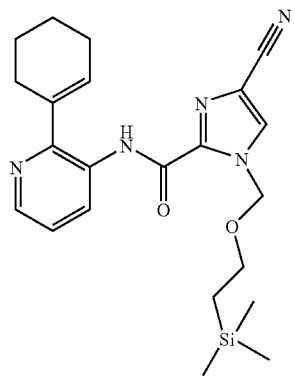

A solution of 365 mg (2.10 mmol) of 2-cyclohex-1-enyl-pyridin-3-ylamine (as prepared in the previous step) in $CH_2Cl_2$ (10 mL) was treated with 1.46 g (3.14 mmol) of PyBroP, 704 mg (2.30 mmol) of 4-cyano-1-(2-trimethylsilanyl-ethoxymethyl)-1H-imidazole-2-carboxylate potassium salt (as prepared in Example 11, step (d)), and 1.09 mL (6.28 mmol) of DIEA at RT for 3 h. The mixture was diluted with $CH_2Cl_2$ (20 mL) and washed with saturated aqueous $NaHCO_3$ (1×15 mL). The organic layer was dried ($MgSO_4$) and concentrated in vacuo. Silica gel chromatography of the residue on a 50-g Varian MegaBond Elut SPE column with 1% MeOH—$CH_2Cl_2$ afforded 615 mg (69%) of the title compound as a white solid: $^1$H-NMR ($CDCl_3$; 400 MHz): δ 9.86 (br s, 1H), 8.69 (dd, 1H, J=8.0, 1.6 Hz), 8.37-8.34 (m, 1H), 7.78 (s, 1H), 7.22-7.17 (m, 1H), 6.05 (sept, 1H, J=1.6 Hz), 5.93 (s, 2H), 3.68-3.63 (m, 2H), 2.45-2.39 (m, 2H), 2.37-2.30 (m, 2H), 1.91-1.77 (m, 4H), 1.00-0.95 (m, 2H), 0.00 (s, 9H).

d) 4-Cyano-1H-imidazole-2-carboxylic acid (2-cyclohex-1-enyl-pyridin-3-yl)-amide trifluoroacetic acid salt A solution of 615 mg (1.45 mmol) of 4-cyano-1-(2-trimethylsilanyl-ethoxymethyl)-1H-imidazole-2-carboxylic acid (2-cyclohex-1-enyl-pyridin-3-yl)-amide (as prepared in the previous step) in CH$_2$Cl$_2$ (12 mL) was treated with MeOH (100 µL) and TFA (3 mL) at RT for 3.5 h. MeOH (5 mL) was added to the mixture before concentrating in vacuo. RP-HPLC (C18) of the residue with 10-80% CH$_3$CN in 0.1% TFA/H$_2$O over 30 min afforded 177 mg (30%) of the title compound as a white solid: $^1$H-NMR (CD$_3$OD; 400 MHz): δ 9.03 (dd, 1H, J=8.4, 1.6 Hz), 8.45 (dd, 1H, J=5.2, 1.6 Hz), 8.07 (s, 1H), 7.81-7.74 (m, 1H), 6.36-6.29 (m, 1H), 2.49-2.34 (m, 4H), 1.97-1.79 (m, 4H). Mass spectrum (ESI, m/z): Calcd. for C$_{16}$H$_{15}$N$_5$O, 294.1 (M+H), found 294.1.

EXAMPLE 44

4-Cyano-1H-imidazole-2-carboxylic acid [2-cyclohex-1-enyl-4-(morpholine-4-sulfonyl)-phenyl]-amide

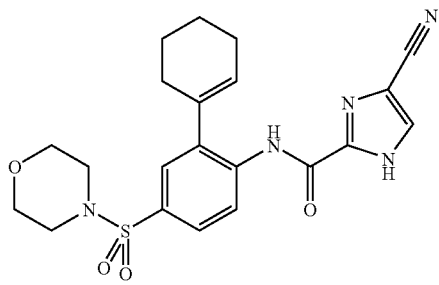

a) 2-Bromo-4-(morpholine-4-sulfonyl)-phenylamine

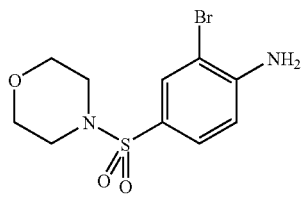

A solution of 250 mg (0.918 mmol) of 4-(4-nitro-benzenesulfonyl)-morpholine in MeOH (15 mL) was treated with 20 mg of 10% Pd/C (Degussa type E101-NE/W, Aldrich, 50% by weight water) under H$_2$ (1 atm). The mixture was stirred at RT for 1.5 h and filtered through Celite. The filter cake was washed with MeOH, and the filtrate was concentrated in vacuo. The residue was taken up in CH$_2$Cl$_2$ (10 mL), cooled to 0° C., and treated with 124 mg (0.698 mmol) of NBS at that temperature for 25 min. The mixture was diluted with CH$_2$Cl$_2$ (15 mL) and washed with saturated aqueous NaHCO$_3$ (1×10 mL). The organic layer was dried (MgSO$_4$) and concentrated in vacuo. Silica gel chromatography of the residue on a 50-g Varian MegaBond Elut SPE column with 40-50% EtOAc-hexane afforded 50.0 mg (17%) of the title compound as a pale tan solid: Mass spectrum (ESI, m/z): Calcd. for C$_{10}$H$_{13}$N$_2$O$_3$SBr, 321.0 (M+H), found 320.9/322.8.

b) 2-Cyclohex-1-enyl-4-(morpholine-4-sulfonyl)-phenylamine

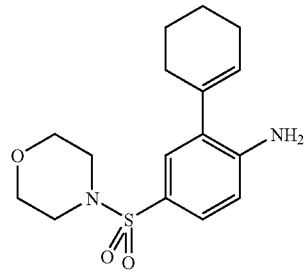

A solution of 50.0 mg (0.156 mmol) of 2-bromo-4-(morpholine-4-sulfonyl)-phenylamine (as prepared in the previous step) in toluene (4 mL) and EtOH (2 mL) was treated with 623 µL (1.25 mmol) of 2.0 M aqueous Na$_2$CO$_3$ and 20.6 mg (0.163 mmol) of cyclohex-1-enylboronic acid. The mixture was degassed via sonication, placed under Ar, treated with 12.6 mg (0.0109 mmol) of Pd(PPh$_3$)$_4$, and heated to 80° C. for 3.5 h. The mixture was cooled to RT, stirred for 16 h, diluted with EtOAc (10 mL) and washed with saturated aqueous NaHCO$_3$ (1×10 mL) and brine (1×10 mL). The organic layer was dried (MgSO$_4$) and concentrated in vacuo. Silica gel chromatography of the residue on a 25-g Varian MegaBond Elut SPE column with 25-50% EtOAc-hexane afforded 20.0 mg (40%) of the title compound as an off-white solid: Mass spectrum (ESI, m/z): Calcd. for C$_{16}$H$_{22}$N$_2$O$_3$S, 323.1 (M+H), found 323.1.

c) 4-Cyano-1-(2-trimethylsilanyl-ethoxymethyl)-1H-imidazole-2-carboxylic acid [2-cyclohex-1-enyl-4-(morpholine-4-sulfonyl)-phenyl]-amide

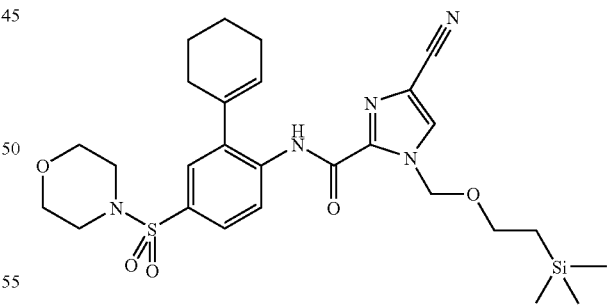

A suspension of 24.0 mg (0.0785 mmol) of 4-cyano-1-(2-trimethylsilanyl-ethoxymethyl)-1H-imidazole-2-carboxylate potassium salt (as prepared in Example 11, step (d)) in CH$_2$Cl$_2$ (5 mL) was treated with 6.40 µL (0.0785 mmol) of pyridine for 5 min. The mixture was cooled to 0° C., and 5.70 µL (0.0785 mmol) of SOCl$_2$ was added, allowed to warm to RT, and stirred for 30 min. A solution of 20.0 mg (0.0620 mmol) of 2-cyclohex-1-enyl-4-(morpholine-4-sulfonyl)-phenylamine (as prepared in the previous step) and triethylamine (12.0 µL, 0.0854 mmol) in CH$_2$Cl$_2$ (1 mL) was treated with the acid chloride solution and stirred at RT for 7 h. The mixture was diluted with CH$_2$Cl$_2$ (10 mL) and washed with water (1×10 mL). The organic layer was dried (MgSO$_4$) and concentrated in vacuo to afford 15.0 mg (37%) of the title compound as a tan solid: Mass spectrum (ESI, m/z): Calcd. for C$_{27}$H$_{37}$N$_5$O$_5$SSi, 572.2 (M+H), found 572.0.

d) 4-Cyano-1H-imidazole-2-carboxylic acid [2-cyclohex-1-enyl-4-(morpholine-4-sulfonyl)-phenyl]-amide A solution of 15.0 mg (0.0262 mmol) of 4-cyano-1-(2-trimethylsilanyl-ethoxymethyl)-1H-imidazole-2-carboxylic acid [2-cyclohex-1-enyl-4-(morpholine-4-sulfonyl)-phenyl]-amide (as prepared in the previous step) in CH$_2$Cl$_2$ (5 mL) was treated with MeOH (1 drop) and TFA (1 mL). The mixture was stirred at RT for 2 h, and the solvents were evaporated in vacuo. Purification of the residue by RP-HPLC (C18) with 10-80% CH$_3$CN in 0.1% TFA/H$_2$O over 30 min afforded 3.4 mg (29%) of the title compound as a white solid: $^1$H-NMR (CD$_3$OD; 400 MHz): δ 8.62 (d, 1H, J=8.8 Hz), 8.07 (s, 1H), 7.72 (dd, 1H, J=8.8, 2.0 Hz), 7.57 (d, 1H, J=2.0 Hz), 6.01-5.96 (m, 1H), 3.77-3.70 (m, 4H), 3.02-2.95 (m, 4H), 2.40-2.30 (m, 4H), 1.97-1.82 (m, 4H). Mass spectrum (ESI, m/z): Calcd. for C$_{21}$H$_{23}$N$_5$O$_4$S, 442.2 (M+H), found 441.9.

EXAMPLE 45

4-Cyano-1H-imidazole-2-carboxylic acid [(4,4-dimethyl-cyclohex-1-enyl)-4-sulfamoyl-phenyl]-amide

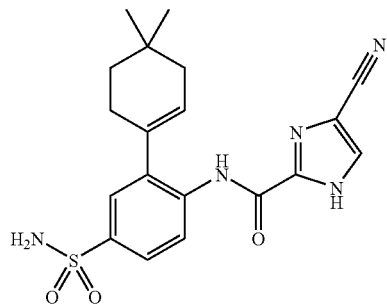

a) 4-Cyano-1-(2-trimethylsilanyl-ethoxymethyl)-1H-imidazole-2-carboxylic acid [4-tert-butylsulfamoyl-2-(4,4-dimethyl-cyclohex-1-enyl)-phenyl]-amide

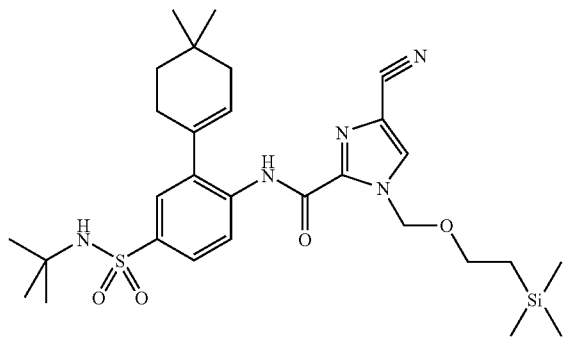

A solution of 300 mg (0.976 mmol) of 4-amino-3-bromo-N-tert-butyl-benzenesulfonamide (as prepared in Example 48, step (a)) in toluene (8 mL) and EtOH (4 mL) was treated with 253 mg (1.07 mmol) of 2-(4,4-dimethyl-cyclohex-1-enyl)-4,4,5,5-tetramethyl-[1,3,2]dioxaborolane and 3.90 mL (7.81 mmol) of 2.0 M Na$_2$CO$_3$. The mixture was degassed via sonication, placed under Ar, treated with 113 mg (0.0976 mmol) of Pd(PPh$_3$)$_4$, and heated to 80° C. for 6 h. The mixture was diluted with EtOAc (30 mL) and washed with water (2×20 mL). The organic layer was dried (MgSO$_4$) and concentrated in vacuo. Silica gel chromatography of the residue on a 50-g Varian MegaBond Elut SPE column with 1-4% MeOH—CH$_2$Cl$_2$ afforded 158 mg (48%) of 4-amino-N-tert-butyl-3-(4,4-dimethyl-cyclohex-1-enyl)-benzenesulfonamide as a colorless glassy solid. A suspension of 215 mg (0.704 mmol) 4-cyano-1-(2-trimethylsilanyl-ethoxymethyl)-1H-imidazole-2-carboxylate potassium salt (as prepared in Example 11, step (d)) in CH$_2$Cl$_2$ (10 mL) was treated with 60.0 μL (0.704 mmol) of pyridine for 5 min. The mixture was then treated with 51.4 μL (0.704 mmol) of SOCl$_2$ at RT for 30 min. A solution of 158 mg (0.0470 mmol) of 4-amino-N-tert-butyl-3-(4,4-dimethyl-cyclohex-1-enyl)-benzenesulfonamide (as prepared earlier in this step) in CH$_2$Cl$_2$ (5 mL) was treated with the acid chloride solution and stirred at RT for 17 h. The mixture was diluted with CH$_2$Cl$_2$ (30 mL) and washed with saturated aqueous NaHCO$_3$ (1×20 mL). The organic layer was dried (MgSO$_4$) and concentrated in vacuo. Silica gel chromatography of the residue on a 50-g Varian Mega-Bond Elut SPE column with 1% MeOH—CH$_2$Cl$_2$ afforded 100.0 mg (17%) of the title compound as a white solid: $^1$H-NMR (CDCl$_3$; 400 MHz): δ 9.95 (br s, 1H), 8.55 (d, 1H, J=8.8 Hz), 7.78 (dd, 1H, J=8.8, 2.4 Hz), 7.78 (s, 1H), 7.69 (d, 1H, J=2.4 Hz), 5.92 (s, 2H), 5.84-5.80 (m, 1H), 4.55 (br s, 1H), 3.68-3.62 (m, 2H), 2.32-2.24 (m, 2H), 2.14-2.08 (m, 2H), 1.63-1.56 (m, 2H), 1.23 (s, 9H), 1.11 (s, 6H), 1.00-0.94 (m, 2H), 0.00 (s, 9H).

b) 4-Cyano-1H-imidazole-2-carboxylic acid [(4,4-dimethyl-cyclohex-1-enyl)-4-sulfamoyl-phenyl]-amide A solution of 100 mg (0.171 mmol) of 4-cyano-1-(2-trimethylsilanyl-ethoxymethyl)-1H-imidazole-2-carboxylic acid [4-tert-butylsulfamoyl-2-(4,4-dimethyl-cyclohex-1-enyl)-phenyl]-amide (as prepared in the previous step) in CH$_2$Cl$_2$ (10 mL) was treated with 62.0 μL EtOH, 67.0 μL (0.616 mmol) of anisole, and TFA (750 μL) at RT for 18 h. EtOH (3 mL) was added, the mixture was concentrated, the residue was subjected again to the conditions above except that 900 μL of TFA was used, and then was subjected a third time with 1.70 mL of TFA. Solvents were evaporated in vacuo. Purification of the residue by RP-HPLC (C18) with 20-100% CH$_3$CN in 0.1% TFA/H$_2$O over 30 min afforded 27.7 mg (41%) of the title compound as a white solid: $^1$H-NMR (CD$_3$OD; 400 MHz): δ 8.40 (d, 1H, J=8.8 Hz), 7.92 (s, 1H), 7.71 (dd, 1H, J=8.8, 2.4 Hz), 7.62 (d, 1H, J=2.4 Hz), 5.80-5.73 (m, 1H), 2.30-2.21 (m, 2H), 2.08-1.99 (m, 2H), 1.60-1.50 (m, 2H), 1.02 (s, 6H).

EXAMPLE 46

4-Cyano-1H-imidazole-2-carboxylic acid [2-(4,4-dimethyl-cyclohex-1-enyl)-4-(2-sulfamoyl-ethyl)-phenyl]-amide

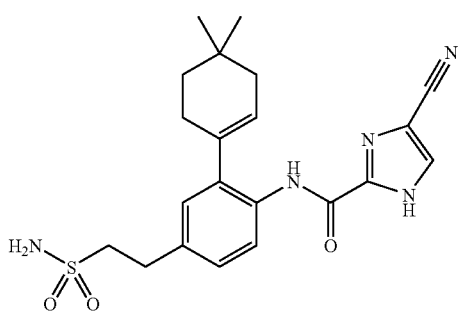

a) 2-[4-Amino-3-(4,4-dimethyl-cyclohex-1-enyl)-phenyl]-ethanesulfonic acid tert-butyl amide

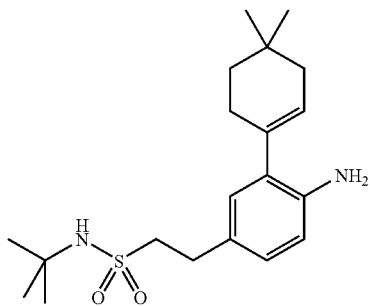

A solution of 380 mg (1.13 mmol) of 2-(4-amino-3-bromo-phenyl)-ethanesulfonic acid tert-butylamide (as prepared in Example 47, step (a)) in toluene (10 mL) and EtOH (5 mL) was treated with 321 mg (1.36 mmol) of 4,4-dimethylcyclohex-1-enylboronic acid and 4.53 mL (9.06 mmol) of 2.0 M aqueous Na$_2$CO$_3$. The mixture was degassed via sonication, placed under Ar, treated with 131 mg (0.113 mmol) of Pd(PPh$_3$)$_4$, and heated to 80° C. for 19 h. The mixture was diluted with EtOAc (30 mL) and washed with water (1×20 mL). The organic layer was dried (MgSO$_4$) and concentrated in vacuo. Silica gel chromatography of the residue on a 50-g Varian MegaBond Elut SPE column with 1% MeOH—CH$_2$Cl$_2$ afforded 267 mg (64%) of the title compound as an off-white solid: Mass spectrum (ESI, m/z): Calcd. for C$_{20}$H$_{32}$N$_2$O$_2$S, 365.2 (M+H), found 365.2.

b) 4-Cyano-1-(2-trimethylsilanyl-ethoxymethyl)-1H-imidazole-2-carboxylic acid [4-(2-(tert-butylsulfamoyl)-ethyl)-2-(4,4-dimethyl-cyclohex-1-enyl)-phenyl]-amide

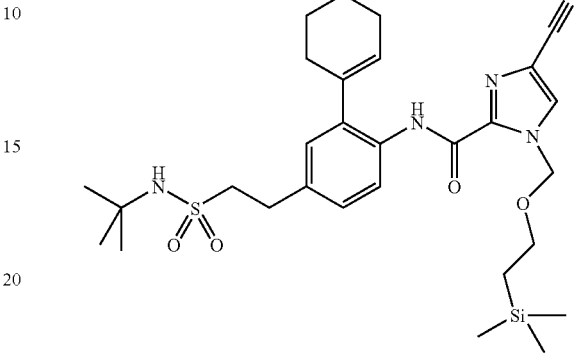

A solution of 267 mg (0.732 mmol) of 2-[4-amino-3-(4,4-dimethyl-cyclohex-1-enyl)-phenyl]-ethanesulfonic acid tert-butyl amide (as prepared in the previous step) in CH$_2$Cl$_2$ (10 mL) was treated with 512 mg (1.10 mmol) of PyBroP, 246 mg (0.806 mmol) of 4-cyano-1-(2-trimethylsilanyl-ethoxymethyl)-1H-imidazole-2-carboxylate potassium salt (as prepared in Example 11, step (d)) and 383 µL (2.20 mmol) of DIEA. The mixture was stirred at RT for 3 h, diluted with CH$_2$Cl$_2$ (20 mL), and washed with saturated aqueous NaHCO$_3$ (1×15 mL). The organic layer was dried (MgSO$_4$) and concentrated in vacuo. Silica gel chromatography of the residue on a 50-g Varian MegaBond Elut SPE column with 25% EtOAc-hexane afforded 311 mg (69%) of the title compound as a white solid: $^1$H-NMR (CDCl$_3$; 400 MHz): δ 9.73 (br s, 1H), 8.32 (d, 1H, J=8.4 Hz), 7.76 (s, 1H), 7.13 (dd, 1H, J=8.4, 2.0 Hz), 7.02 (d, 1H, J=2.0 Hz), 5.94 (s, 2H), 5.77-5.72 (m, 1H), 4.07 (br s, 1H), 3.69-3.62 (m, 2H), 3.35-3.27 (m, 2H), 3.14-3.06 (m, 2H), 2.31-2.23 (m, 2H), 2.12-2.07 (m, 2H), 1.58 (t, 2H, J=6.4 Hz), 1.34 (s, 9H), 1.10 (s, 6H), 1.00-0.94 (m, 2H).

c) 4-Cyano-1H-imidazole-2-carboxylic acid [2-(4,4-dimethyl-cyclohex-1-enyl)-4-(2-sulfamoyl-ethyl)-phenyl]-amide A solution of 311 mg (0.506 mmol) of 4-cyano-1-(2-trimethylsilanyl-ethoxymethyl)-1H-imidazole-2-carboxylic acid [4-(2-tert-butylsulfamoyl-ethyl)-2-(4,4-dimethyl-cyclohex-1-enyl)-phenyl]-amide (as prepared in the previous step) in CH$_2$Cl$_2$ (6 mL) was treated with EtOH (175 µL), anisole (80.0 µL), and TFA (1.8 mL). Additional TFA (0.5 mL each) was added at 3.5 and at 26 h. The mixture stirred at RT for a total of 48 h. MeOH (3 mL) was added, the mixture was concentrated in vacuo, and the residue was purified by RP-HPLC (C18) with 20-100% CH$_3$CN in 0.1% TFA/H$_2$O over 30 min to afford 70.5 mg (32%) of the title compound as a white solid: $^1$H-NMR (CD$_3$OD; 400 MHz): δ 8.17 (d, 1H, J=8.0 Hz), 8.01 (s, 1H), 7.21 (dd, 1H, J=8.0, 2.0 Hz), 7.13 (d, 1H, J=2.0 Hz), 5.79-5.73 (m, 1H), 3.40-3.34 (m, 1H), 3.16-3.07 (m, 2H), 2.37-2.29 (m, 2H), 2.13-2.07 (m, 2H), 1.65-1.57 (m, 2H), 1.10 (s, 6H). Mass spectrum (ESI, m/z): Calcd. for $C_{21}H_{25}N_5O_3S$, 428.2 (M+H), found 428.1.

EXAMPLE 47

4-Cyano-1H-imidazole-2-carboxylic acid [2-cyclohex-1-enyl-4-(2-sulfamoyl-ethyl)-phenyl]-amide trifluoroacetic acid salt

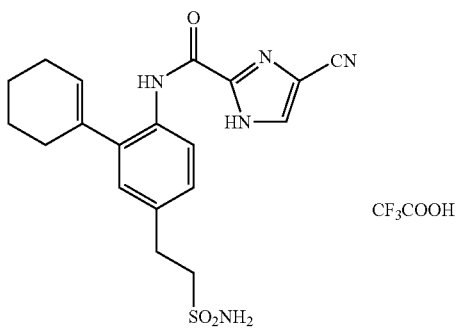

a) 2-(4-Amino-3-bromo-phenyl)-ethanesulfonic acid tert-butylamide

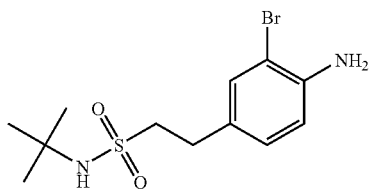

To a solution of tert-BuNH$_2$ (15.6 mL, 148 mmol) in THF (50 mL) at 0° C., 2-(4-nitro-phenyl)-ethanesulfonyl chloride (WO 2006010079, 1.9 g, 7.6 mmol) was added portionwise. The resulting mixture was stirred for 24 h at RT. The solvent was removed in vacuo and the residue was taken up in DCM (50 mL) and cold 0.5 N HCl (50 mL). The organic layer was separated, dried (Na$_2$SO$_4$) and concentrated to obtain 2-(4-nitro-phenyl)-ethanesulfonic acid tert-butylamide (1.3 g, 62%) which was used directly without further purification.

2-(4-Nitro-phenyl)-ethanesulfonic acid tert-butylamide (as prepared in the step above, 633 mg, 2.21 mmol) was hydrogenated under balloon pressure in EtOH (20 mL) using 10% Pd/C (100 mg) for 12 h. The reaction mixture was filtered through Celite and concentrated to obtain 2-(4-amino-phenyl)-ethanesulfonic acid tert-butylamide (536 mg, 95%) which was used directly without further purification.

4-[2-(2-Methyl-propane-2-sulfonyl)-ethyl]-phenylamine (as prepared in the step above, 536 mg, 2.09 mmol) was dissolved in CH$_3$CN/DCM (2:1) (10 mL) and cooled to 0° C. NBS (345 mg, 1.93 mmol) was added portionwise. The reaction mixture was stirred at RT for 15 min and concentrated in vacuo. The residue obtained was taken up in DCM (20 mL) and washed with satd NaHCO$_3$ (10 mL) and 10% Na$_2$S$_2$O$_3$ (10 mL). The organic layer was separated, dried and concentrated to obtain 2-(4-amino-3-bromo-phenyl)-ethanesulfonic acid tert-butylamide (665 mg, 95%). Mass spectrum (ESI, m/z): Calcd. for $C_{12}H_{19}BrN_2O_2S$, 335.0, 336.0 (M+H), found 335.2, 336.2.

b) 2-(4-Amino-3-cyclohex-1-enyl-phenyl)-ethanesulfonic acid tert-butylamide

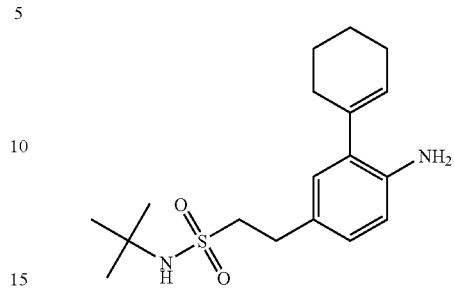

The title compound was prepared according to the Suzuki coupling procedure of Example 44, step (b) using cyclohex-1-enyl boronic acid (117 mg, 0.931 mmol) and 2-(4-amino-3-bromo-phenyl)-ethanesulfonic acid tert-butylamide (as prepared in the previous step, 250 mg, 0.745 mmol) and purified on silica (20% EtOAc/hexanes) (228 mg, 91%). $^1$H-NMR (CDCl$_3$; 400 MHz): δ 6.87 (dd, 1H, J=8.0, 2.1 Hz), 6.82 (d, 1H, J=2.1 Hz), 6.64 (d, 1H, J=8.0 Hz), 5.72 (br s, 1H), 4.12 (s, 1H), 3.82 (br s, 2H), 3.28 (m, 2H), 2.96 (m, 2H), 2.19-2.23 (m, 4H), 1.62-1.82 (m, 4H), 1.31 (s, 9H).

c) 4-Cyano-1-(2-trimethylsilanyl-ethoxymethyl)-1H-imidazole-2-carboxylic acid [4-(2-tert-butylsulfamoyl-ethyl)-2-cyclohex-1-enyl-phenyl]-amide

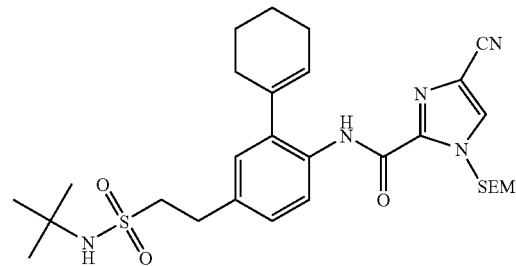

To a suspension of 4-cyano-1-(2-trimethylsilanyl-ethoxymethyl)-1H-imidazole-2-carboxylic acid, potassium salt (as prepared in Example 11, step (d), 228 mg, 0.746 mmol) and pyridine (66 µL, 0.81 mmol) in DCM (5 mL), SOCl$_2$ (60 µL, 0.81 mmol) was added at 0° C. The resulting mixture was stirred at RT for 1 h and transferred to a mixture of 2-(4-amino-3-cyclohex-1-enyl-phenyl)-ethanesulfonic acid tert-butylamide (as prepared in the previous step, 228 mg, 0.670 mg) and pyridine (66 µL, 0.81 mmol) in DCM (5 mL) at 0° C. The resulting mixture was stirred at RT over night. Water (20 mL) was then added and organic layer was separated, dried (Na$_2$SO$_4$) and concentrated. The residue obtained was purified on silica (20-50% EtOAc/hexane) to obtain the title compound (271 mg, 68%). Mass spectrum (ESI, m/z): Calcd. for $C_{29}H_{43}N_5O_4SSi$, 586.2 (M+H), found 586.0.

d) 4-Cyano-1H-imidazole-2-carboxylic acid [2-cyclohex-1-enyl-4-(2-sulfamoyl-ethyl)-phenyl]-amide trifluoroacetic acid salt To a solution of 4-cyano-1-(2-trimethylsilanyl-ethoxymethyl)-1H-imidazole-2-carboxylic acid [4-(2-tert-butylsulfamoyl-ethyl)-2-cyclohex-1-enyl-phenyl]-amide (as the prepared in previous step, 275 mg, 0.470 mmol) in DCM (5 mL), EtOH (140 µL), anisole (51 µL) and TFA (1.5 mL) were added. The resulting solution was stirred at RT for 6 h. An additional 0.35 mL of TFA was added and the resulting mixture was stirred at RT overnight. The reaction mixture was concentrated and the residue was subjected to RP-HPLC eluting with 20% to 100% $CH_3CN$ in 0.1% $TFA/H_2O$ over 20 min on a C18 column to afford the title compound (26.6 mg, 11%). $^1$H-NMR (DMSO-$d_6$; 400 MHz): δ 9.72 (s, 1H), 8.31 (s, 1H), 7.85 (d, 1H, J=8.4 Hz), 7.17 (d, 1H, J=8.4 Hz), 7.10 (s, 1H), 6.82 (s, 2H), 5.72 (br s, 1H), 3.23 (m, 2H), 2.92 (m, 2H), 2.1-2.29 (m, 4H), 1.62-1.75 (m, 4H); Mass spectrum (ESI, m/z): Calcd. for $C_{19}H_{21}N_5O_3S$, 400.1 (M+H), found 400.1.

EXAMPLE 48

5-Cyano-1H-imidazole-2-carboxylic acid (2-cyclohex-1-enyl-4-sulfamoyl-phenyl)-amide trifluoroacetic acid salt

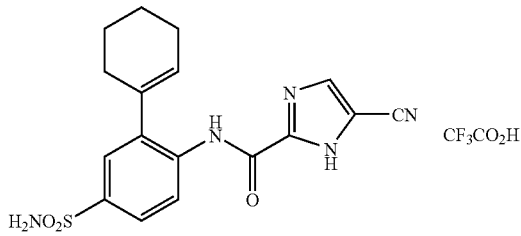

a) 4-Amino-N-tert-butyl-3-cyclohex-1-enyl-benzenesulfonamide

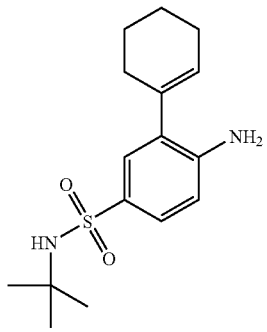

To a solution of 4-amino-N-tert-butyl-benzenesulfonamide (J. Med. Chem. (2003), 46(16), 3463-3475, 228 mg, 1.00 mmol) in DCM (10 mL), NBS (178 mg, 1.00 mmol) was added. The resulting mixture was stirred at RT for 30 min and washed with satd $NaHCO_3$ (10 mL) and 10% aq $Na_2S_2O_3$ (10 mL). The organic layer was separated, dried and concentrated to obtain 4-amino-3-bromo-N-tert-butyl-benzenesulfonamide (163 mg, 53%).

4-Amino-N-tert-butyl-3-cyclohex-1-enyl-benzenesulfonamide was prepared according to the Suzuki coupling procedure of Example 44, step (b) using cyclohex-1-enyl boronic acid (63 mg, 0.50 mmol) and 4-amino-3-bromo-N-tert-butyl-benzenesulfonamide (123 mg, 0.400 mmol, as prepared above) to obtain 4-amino-N-tert-butyl-3-cyclohex-1-enyl-benzenesulfonamide (87 mg, 70%) after purification on silica (30% EtOAc/hexanes). Mass spectrum (ESI, m/z): Calcd. for $C_{16}H_{24}N_2O_2S$, 309.1 (M+H), found 309.1 b) 5-Cyano-1-(2-trimethylsilanyl-ethoxymethyl)-1H-imidazole-2-carboxylic acid [2-cyclohex-1-enyl-4-(2-methyl-propane-2-sulfonylamino)-phenyl]-amide

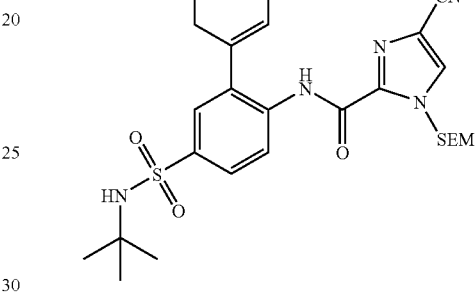

4-Amino-N-tert-butyl-3-cyclohex-1-enyl-benzenesulfonamide (as prepared in previous step, 276 mg, 0.896 mmol) was coupled with 4-cyano-1-(2-trimethylsilanyl-ethoxymethyl)-1H-imidazole-2-carboxylic acid, potassium salt (as prepared in Example 11, step (d) 328 mg, 0.896 mmol) as described in Example 47, step (c), to afford the title compound (319 mg, 64%) after purification on silica (20-50% EtOAc/hexane). $^1$H-NMR (CDCl$_3$; 400 MHz): δ 9.92 (s, 1H), 8.51 (d, 1H, J=8.6 Hz), 7.8 (s, 1H), 7.78 (dd, 1H, J=8.6, 2.2 Hz), 7.7 (d, 1H, J=2.2 Hz), 5.92 (s, 2H), 5.89 (br s, 1H), 4.85 (br s, 1H), 3.63 (m, 2H), 2.18-2.39 (m, 4H), 1.87-1.91 (m, 4H), 1.22 (s, 9H), 0.94 (m, 2H), 0.01 (s, 9H).\ c) 5-Cyano-1H-imidazole-2-carboxylic acid (2-cyclohex-1-enyl-4-sulfamoyl-phenyl)-amide trifluoroacetic acid salt To a solution of 5-cyano-1-(2-trimethylsilanyl-ethoxymethyl)-1H-imidazole-2-carboxylic acid [2-cyclohex-1-enyl-4-(2-methyl-propane-2-sulfonylamino)-phenyl]-amide (as prepared in previous step, 319 mg, 0.572 mmol) in DCM (5 mL), EtOH (170 µL), anisole (65 µL) and TFA (1.8 mL) were added. The resulting solution was stirred at RT for 6 h. An additional 0.45 mL of TFA was added and the resulting mixture was stirred at RT overnight. The reaction mixture was concentrated and the residue was subjected to RP-HPLC eluting with 20% to 100% $CH_3CN$ in 0.1% $TFA/H_2O$ over 20 min on a C18 column to afford the title compound (70 mg, 25%). $^1$H-NMR (DMSO-$d_6$; 400 MHz): δ 9.91 (s, 1H), 8.35 (s, 1H), 8.15 (d, 1H, J=8.5 Hz), 7.73 (dd, 1H, J=8.5, 2.2 Hz), 7.63 (d, 1H, J=2.2 Hz), 7.3 (s, 2H), 5.83 (br s, 1H), 2.1-2.3 (m, 4H), 1.62-1.73 (m, 4H); Mass spectrum (ESI, m/z): Calcd. for $C_{17}H_{17}N_5O_3S$, 372.1 (M+H), found 372.0.

EXAMPLE 49

5-Cyano-1H-imidazole-2-carboxylic acid (3-cyclohex-1-enyl-4'-dimethylsulfamoylbiphenyl-4-yl)-amide

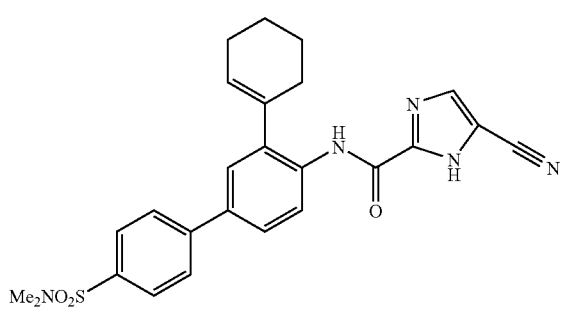

a) 4'-Amino-biphenyl-4-sulfonic acid dimethylamide

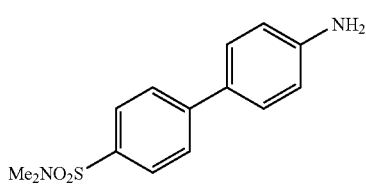

To a round bottom flask was added 4-bromo-N,N-dimethyl-benzenesulfonamide (as prepared in the previous step, 539 mg, 2.28 mmol), 4-aminophenylboronic acid (500 mg, 2.28 mmol), Pd(OAc)$_2$ (51 mg, 0.22 mmol), K$_3$PO$_4$ (967 mg, 4.56 mmol) and 2-(dicyclohexyl-phosphino)-biphenyl (319 mg, 0.910 mmol). The flask was charged with toluene (10 mL) and dioxane (10 mL) and heated to 90° C. under Ar. After 5 h the reaction was concentrated in vacuo and the residue was purified by a 10-g silica gel SPE-column eluting with DCM followed by 10% MeOH-DCM to afford 67 mg (10%) of the title compound as a tan solid. Mass spectrum (ESI, m/z): Calcd. for C$_{14}$H$_{16}$N$_2$O$_2$S, 277.0 (M+H), found 277.1.

b) 4'-Amino-3'-bromo-biphenyl-4-sulfonic acid dimethylamide

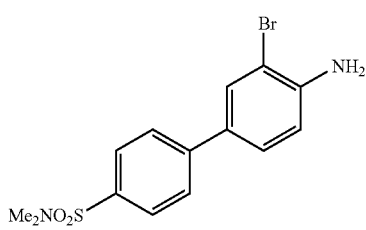

The title compound was prepared from 4'-amino-biphenyl-4-sulfonic acid dimethylamide (as prepared in the previous step, 337 mg, 1.21 mmol) according to the procedure in Example 16, step (b) (142 mg, 33%). Mass spectrum (ESI, m/z): Calcd. for C$_{14}$H$_{15}$BrN$_2$O$_2$S, 355.0 (M+H), found 354.8.

c) 4'-Amino-3'-cyclohex-1-enyl-biphenyl-4-sulfonic acid dimethylamide

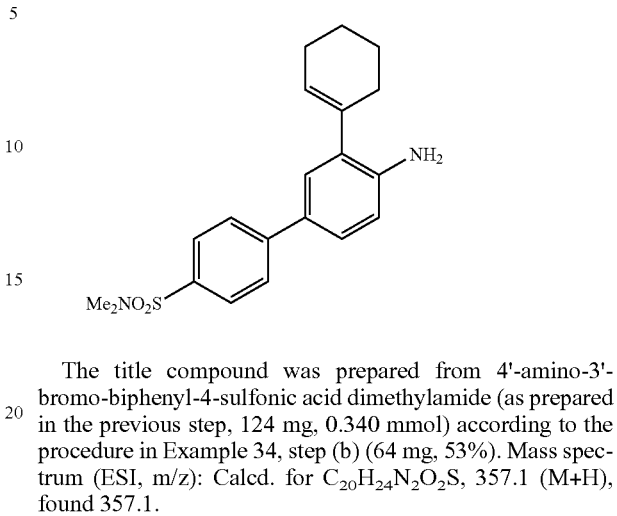

The title compound was prepared from 4'-amino-3'-bromo-biphenyl-4-sulfonic acid dimethylamide (as prepared in the previous step, 124 mg, 0.340 mmol) according to the procedure in Example 34, step (b) (64 mg, 53%). Mass spectrum (ESI, m/z): Calcd. for C$_{20}$H$_{24}$N$_2$O$_2$S, 357.1 (M+H), found 357.1.

d) 4-Cyano-1-(2-trimethylsilanyl-ethoxymethyl)-1H-imidazole-2-carboxylic acid (3-cyclohex-1-enyl-4'-dimethylsulfamoyl-biphenyl-4-yl)-amide

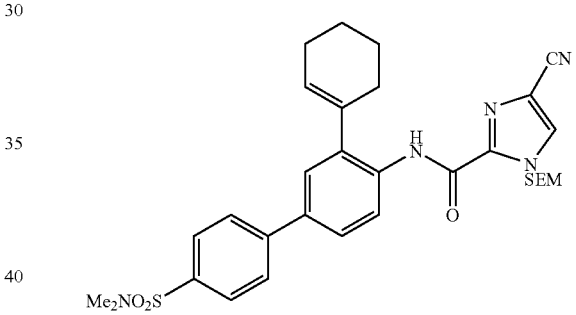

The title compound was prepared from 4'-amino-3'-cyclohex-1-enyl-biphenyl-4-sulfonic acid dimethylamide (as prepared in the previous step, 64 mg, 0.17 mmol), potassium 4-cyano-1-(2-trimethylsilanyl-ethoxymethyl)-1H-imidazole-2-carboxylate (as prepared in Example 11, step (d), 60 mg, 0.19 mmol), PyBroP (117 mg, 0.350 mmol) and DIEA (69 µL, 0.39 mmol) according to the procedure in Example 11, step (f) (84 mg, 70%). Mass spectrum (ESI, m/z): Calcd. for C$_{31}$H$_{39}$N$_5$O$_4$SSi, 606.2 (M+H), found 605.9.

e) 5-Cyano-1H-imidazole-2-carboxylic acid (3-cyclohex-1-enyl-4'-dimethylsulfamoyl-biphenyl-4-yl)-amide The title compound was prepared from 4-cyano-1-(2-trimethylsilanyl-ethoxymethyl)-1H-imidazole-2-carboxylic acid (3-cyclohex-1-enyl-4'-dimethylsulfamoyl-biphenyl-4-yl)-amide (as prepared in the previous step, 82 mg, 0.13 mmol) according to the procedure in Example 11, step (g) (47 mg, 76%). $^1$H-NMR (DMSO-d$_6$; 400 MHz): δ 9.82 (s, 1H), 8.35 (d, 1H, J=1.2 Hz), 8.18 (m 1H), 7.95 (d, 2H, J=8.3 Hz), 7.78 (d, 2H, J=7.9 Hz), 7.70 (m, 1H), 7.59 (s, 1H), 5.85 (m, 1H), 2.63 (s, 6H), 2.30-2.18 (m, 4H), 1.77-1.67 (m, 4H). Mass spectrum (ESI, m/z): Calcd. for C$_{25}$H$_{25}$N$_5$O$_3$S, 476.1 (M+H), found 476.0.

EXAMPLE 50

5-Cyano-1H-imidazole-2-carboxylic acid [2-(4,4-dimethyl-cyclohex-1-enyl)-4-(6-methoxy-pyridin-3-yl)-phenyl]-amide

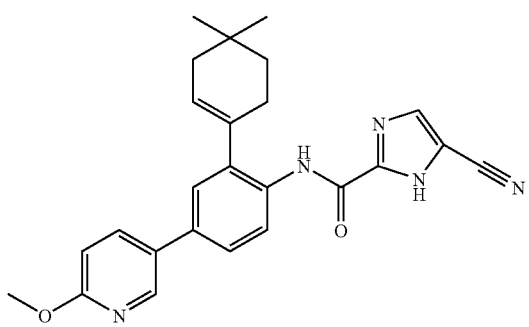

a) 2-Methoxy-5-(4-nitro-phenyl)-pyridine

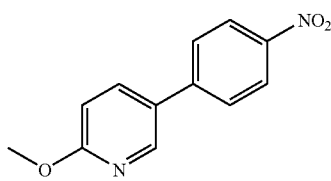

The title compound was prepared from 4,4,5,5-tetramethyl-2-(4-nitro-phenyl)-[1,3,2]dioxaborolane (899 mg, 3.60 mmol), 5-bromo-2-methoxy-pyridine (616 mg, 3.28 mmol) and Pd(PPh$_3$)$_4$ (380 mg, 0.360 mmol) according to the procedure in Example 44, step (b) (615 mg, 94%). Mass spectrum (ESI, m/z): Calcd. for C$_{12}$H$_{10}$N$_2$O$_3$, 231.0 (M+H), found 231.2.

b) 4-(6-Methoxy-pyridin-3-yl)-phenylamine

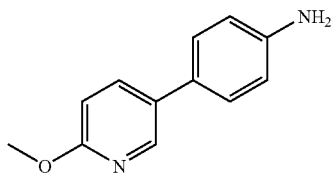

A mixture of 2-methoxy-5-(4-nitro-phenyl)-pyridine (as prepared in the previous step, 102 mg, 0.443 mmol) and 5% Pd—C (80 mg) was stirred under 1 atm H$_2$ in 4 mL of EtOH for 4 h and then filtered through Celite and concentrated in vacuo to afford 73 mg (82%) of the title compound. Mass spectrum (ESI, m/z): Calcd. for C$_{12}$H$_{12}$N$_2$O, 201.0 (M+H), found 201.3.

c) 2-Bromo-4-(6-methoxy-pyridin-3-yl)-phenylamine

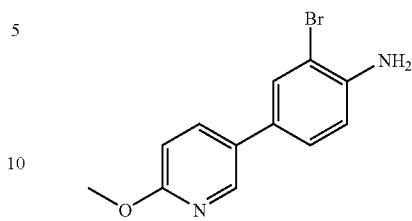

The title compound was prepared from 4-(6-methoxy-pyridin-3-yl)-phenylamine (as prepared in the previous step, 73 mg, 0.36 mmol) and NBS (65 mg, 0.36 mmol) according to the procedure in Example 16, step (b) (20 mg, 20%). Mass spectrum (ESI, m/z): Calcd. for Cl$_2$H$_{11}$BrN$_2$O, 279.0 (M+H), found 279.2.

d) 2-(4,4-Dimethyl-cyclohex-1-enyl)-4-(6-methoxy-pyridin-3-yl)-phenylamine

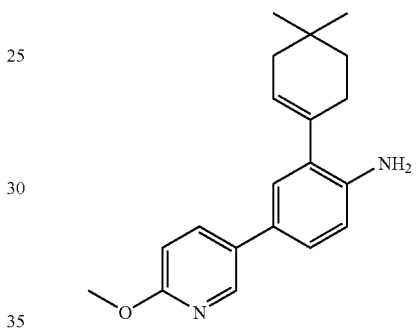

The title compound was prepared from 2-bromo-4-(6-methoxy-pyridin-3-yl)-phenylamine (as prepared in the previous step, 20 mg, 0.07 mmol), 4,4-dimethylcyclohexen-1-yl boronic acid (14 mg, 0.086 mmol), Pd(PPh$_3$)$_4$ (8.0 mg, 0.007 mmol) and 2M Na$_2$CO$_3$ (0.28 mL, 0.56 mmol) according to the procedure in Example 44, step (b) (16 mg, 76%). Mass spectrum (ESI, m/z): Calcd. for C$_{20}$H$_{24}$N$_2$O, 309.1 (M+H), found 309.2.

e) 4-Cyano-1-(2-trimethylsilanyl-ethoxymethyl)-1H-imidazole-2-carboxylic acid [2-(4,4-dimethyl-cyclohex-1-enyl)-4-(6-methoxy-pyridin-3-yl)-phenyl]-amide

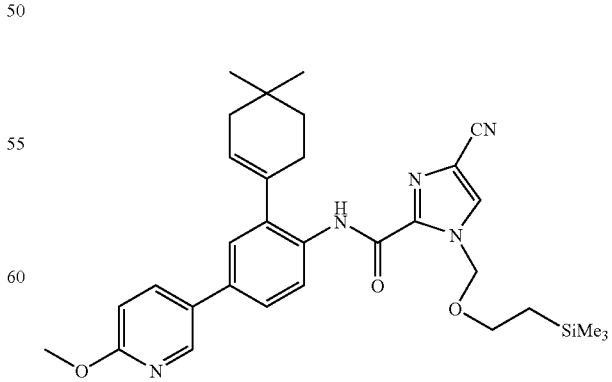

The title compound was prepared from 2-(4,4-dimethyl-cyclohex-1-enyl)$_4$-(6-methoxy-pyridin-3-yl)-phenylamine (as prepared in the previous step, 16.4 mg, 0.0530 mmol), potassium 4-cyano-1-(2-trimethylsilanyl-ethoxymethyl)-1H-imidazole-2-carboxylate (as prepared in Example 11, step (d), 23 mg, 0.074 mmol), PyBroP (40 mg, 0.084 mmol) and DIEA (23 μL, 0.13 mmol) according to the procedure in Example 11, step (f) (20 mg, 68%). Mass spectrum (ESI, m/z): Calcd. for $C_{31}H_{39}N_5O_3Si$, 558.2 (M+H), found 558.3.

f) 5-Cyano-1H-imidazole-2-carboxylic acid [2-(4,4-dimethyl-cyclohex-1-enyl)-4-(6-methoxy-pyridin-3-yl)-phenyl]-amide

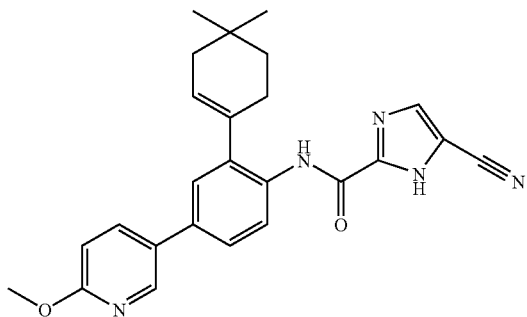

The title compound was prepared from 4-cyano-1-(2-trimethylsilanyl-ethoxymethyl)-1H-imidazole-2-carboxylic acid [2-(4,4-dimethyl-cyclohex-1-enyl)-4-(6-methoxy-pyridin-3-yl)-phenyl]-amide (as prepared in the previous step, 20 mg, 0.035 mmol) according to the procedure in Example 11, step (g) (15 mg, 100%). $^1$H-NMR (DMSO-d$_6$; 400 MHz): δ 9.78 (s, 1H), 8.47 (d, 1H, J=2.3 Hz), 8.26 (s, 1H), 8.12 (d, 1H, J=8.4 Hz), 8.02 (dd, 1H, J=8.4, 2.4 Hz), 7.60 (m, 1H), 7.48 (d, 1H, J=1.9 Hz), 6.90 (d, 1H, J=8.6 Hz), 5.72 (m, 1H), 3.19 (s, 3H), 2.29 (m, 2H), 1.97 (m, 2H), 1.50 (m, 2H), 1.00 (s, 6H). Mass Spectrum (ESI, m/z): Calcd. for $C_{25}H_{25}N_5O_2$, 428.2 (M+H), found 428.2.

EXAMPLE 51

5-Cyano-1H-imidazole-2-carboxylic acid [2-(dimethyl-cyclohex-1-enyl)-6-(1-hydroxy-1-methyl-ethyl)-pyridin-3-yl]-amide

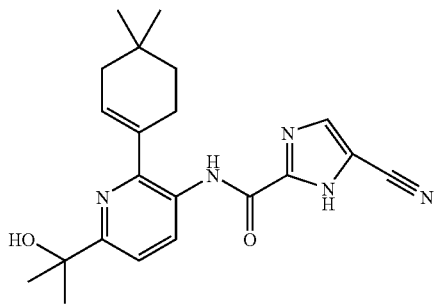

a) 6-Bromo-2-iodo-pyridin-3-ylamine

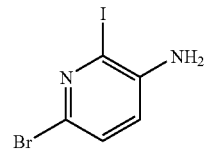

To a stirred solution of 6-bromo-pyridin-3-ylamine (10.2 g, 0.0580 mol) and Ag$_2$SO$_4$ (18.1 g, 0.0580 mol) in EtOH (150 mL) was added I$_2$ (7.59 g, 0.0580 mol) and the reaction was allowed to stir overnight. At this time hexane (200 mL) was added and the resultant mixture was filtered through Celite. The solvent was removed in vacuo, dissolved in CHCl$_3$ (200 mL), washed with aqueous saturated Na$_2$S$_2$O$_3$ (100 mL), water (1×100 mL), and dried (Na$_2$SO$_4$). The solvent was concentrated in vacuo and the residue was dissolved in hot EtOAc (100 mL), filtered and treated with hexanes (100 mL). Filtration gave 11.2 g (65%) of the title compound as a white crystalline material. $^1$H-NMR (CDCl$_3$; 400 MHz): δ 7.10 (d, 1H, J=8.2 Hz), 6.74 (d, 1H, J=8.2 Hz), 4.06 (br s, 2H).

b) 6-Bromo-2-(4,4-dimethyl-cyclohex-1-enyl)-pyridin-3-ylamine

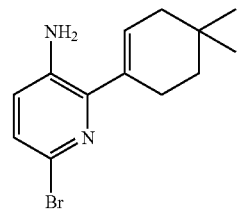

The title compound was prepared from 6-bromo-2-iodo-pyridin-3-ylamine (as prepared in the previous step, 348 mg, 1.17 mmol), 4,4-dimethylcyclohexen-1-yl boronic acid (198 mg, 1.28 mmol), Pd(PPh$_3$)$_4$ (135 mg, 0.117 mol) and 2M Na$_2$CO$_3$ (15.2 mL, 30.5 mmol) according to the procedure in Example 44, step (b) (417 mg, 46%). $^1$H-NMR (CDCl$_3$; 400 MHz): δ 7.06 (d, 1H, J=8.3 Hz), 6.85 (d, 1H, J=8.3 Hz), 5.95 (m, 1H), 3.86 (br s, 2H), 2.43-2.39 (m, 2H), 1.99-1.97 (m, 2H), 1.51 (t, 2H, J=6.4 Hz), 0.99 (s, 6H).

c) 4-Cyano-1-(2-trimethylsilanyl-ethoxymethyl)-1H-imidazole-2-carboxylic acid [6-bromo-2-(4,4-dimethyl-cyclohex-1-enyl)-pyridin-3-yl]-amide

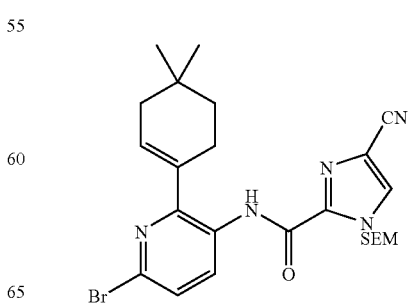

The title compound was prepared from 6-bromo-2-(4,4-dimethyl-cyclohex-1-enyl)-pyridin-3-ylamine (as prepared in the previous step, 60 mg, 0.21 mmol), potassium 4-cyano-1-(2-trimethylsilanyl-ethoxymethyl)-1H-imidazole-2-carboxylate (as prepared in Example 11, step (d), 91.0 mg, 0.290 mmol), PyBroP (157 mg, 0.330 mmol) and DIEA (91.0 µL, 0.520 mmol) according to the procedure in Example 11, step (f) (84 mg, 78%). $^1$H-NMR (CDCl$_3$; 400 MHz): δ 9.91 (s, 1H), 8.64 (d, 1H, J=8.6 Hz), 7.79 (s, 1H), 7.38 (d, 1H, J=8.6 Hz), 6.00 (m, 1H), 5.92 (s, 2H), 3.67 (m, 2H), 2.46 (m, 2H), 2.14 (m, 2H), 1.62 (t, 2H, J=6.3 Hz), 1.12 (s, 6H), 0.98 (m, 2H).

d) 4-Cyano-1-(2-trimethylsilanyl-ethoxymethyl)-1H-imidazole-2-carboxylic acid [2-(4,4-dimethyl-cyclohex-1-enyl)-6-(1-ethoxy-vinyl)-pyridin-3-yl]-amide

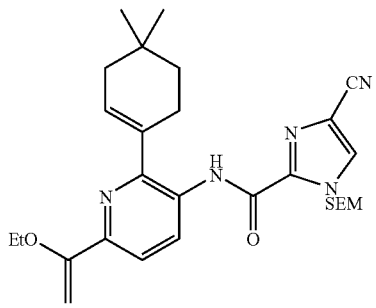

To a round bottom flask containing 4-cyano-1-(2-trimethylsilanyl-ethoxymethyl)-1H-imidazole-2-carboxylic acid [6-bromo-2-(4,4-dimethyl-cyclohex-1-enyl)-pyridin-3-yl]-amide (as prepared in the previous step, 32 mg, 0.060 mmol), Pd(PPh$_3$)$_4$ (7 mg, 0.006 mmol), and tributyl-(1-ethoxy-vinyl)-stannane (30 mg, 0.080 mmol) was added DMF (0.7 mL) and the resultant solution was allowed to stir at 100° C. overnight. The reaction was diluted with EtOAc (25 mL), washed with water (2×25 mL), dried (Na$_2$SO$_4$) and concentrated in vacuo. Purification of the residue by preparative TLC (20% EtOAc-hexanes) afforded 12 mg (43%) of the title compound as an oil. Mass spectrum (ESI, m/z): Calcd. for C$_{28}$H$_{39}$N$_5$O$_3$Si, 522.2 (M+H), found 522.3.

e) 5-Cyano-1H-imidazole-2-carboxylic acid [6-acetyl-2-(4,4-dimethyl-cyclohex-1-enyl)-pyridin-3-yl]-amide

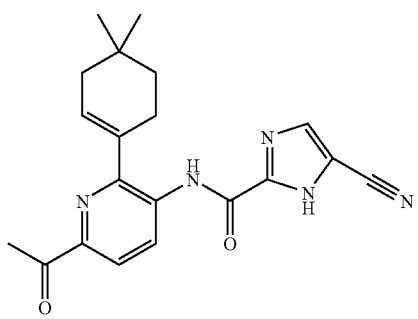

The title compound was prepared from 5-cyano-1-(2-trimethylsilanyl-ethoxymethyl)-1H-imidazole-2-carboxylic acid [2-(4,4-dimethyl-cyclohex-1-enyl)-6-(1-ethoxy-vinyl)-pyridin-3-yl]-amide (as prepared in the previous step, 12 mg, 0.023 mmol) according to the procedure in Example 11, step (g) (4.4 mg, 52%). Mass spectrum (ESI, m/z): Calcd. for C$_{20}$H$_{21}$N$_5$O$_2$, 364.1 (M+H), found 364.1.

f) 5-Cyano-1H-imidazole-2-carboxylic acid [2-(dimethyl-cyclohex-1-enyl)-6-(1-hydroxy-1-methyl-ethyl)-pyridin-3-yl]-amide To a solution of 5-cyano-1H-imidazole-2-carboxylic acid [6-acetyl-2-(4,4-dimethyl-cyclohex-1-enyl)-pyridin-3-yl]-amide (as prepared in the previous step, 6 mg, 0.016 mmol) in THF (1 mL) was added MeMgBr (3 M in THF, 41 µL, 0.072 mmol). After 20 min another 2.5 equivalents of MeMgBr was added and the reaction was allowed to warm to room temperature and quenched with saturated aqueous NaHCO$_3$ (2 mL). The slurry was filtered through a 5-g Sep-Pak SPE column and concentrated in vacuo. The crude product was purified by silica gel chromatography (250-mg, 3-mL Supelco Si tube, gradient CHCl$_3$-2% CHCl$_3$-MeOH) to afford 2.6 mg (43%) of the title compound as a white solid. $^1$H-NMR (CD$_3$OD; 400 MHz): δ 8.44 (d, 1H, J=8.5 Hz), 7.90 (s, 1H), 7.42 (d, 1H, J=8.5 Hz), 5.86 (s, 1H), 2.39-2.37 (m, 2H), 1.99-1.94 (m, 2H), 1.51 (t, 1H, J=6.3 Hz), 1.43 (s, 6H), 0.99 (s, 6H). Mass spectrum (ESI, m/z): Calcd. for C$_{21}$H$_{25}$N$_5$O$_2$, 380.2 (M+H), found 380.1.

EXAMPLE 52

5-Cyano-1H-imidazole-2-carboxylic acid [2-(4,4-dimethyl-cyclohex-1-enyl)-4-(1H-tetrazol-5-ylmethyl)-phenyl]-amide

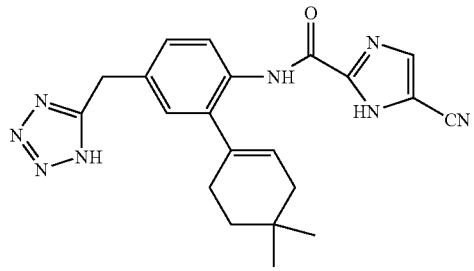

a) (4-Amino-3-bromo-phenyl)-acetonitrile

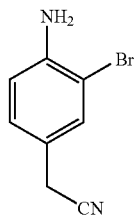

A solution of 4-aminophenylacetonitrile (1.45 g, 10.9 mmol) in acetonitrile (10 mL) at 0° C. was treated with NBS (1.95 g, 10.9 mmol) in acetonitrile (10 mL) dropwise via an addition funnel. The reaction was allowed to warm to room temperature and then concentrated in vacuo. The crude product was dissolved in EtOAc (50 mL), washed with saturated aqueous NaHCO$_3$ (2×50 mL) and dried (Na$_2$SO$_4$). Removal of the solvent in vacuo afforded the title compound (2.12 g, 92%) as a reddish solid. Mass spectrum (ESI, m/z): Calcd. for C$_8$H$_7$BrN$_2$, 210.9 (M+H), found 211.0.

b) [4-Amino-3-(4,4-dimethyl-cyclohex-1-enyl)-phenyl]-acetonitrile

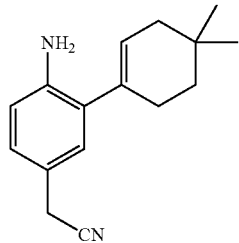

The title compound was prepared from (4-amino-3-bromophenyl)-acetonitrile (as prepared in the previous step, 805 mg, 3.81 mmol), 4,4-dimethylcyclohexen-1-yl boronic acid (705 mg, 4.57 mmol), Pd(PPh$_3$)$_4$ (440 mg, 0.380 mmol), and 2M Na$_2$CO$_3$ (15.2 mL, 30.5 mmol) according to the procedure in Example 34, step (b) (417 mg, 46%). $^1$H—NMR (CDCl$_3$; 400 MHz): δ 6.89 (1H, dd, J=8.1, 2.0 Hz), 6.84 (1H, d, J=2.0 Hz), 6.59 (d, 1H, J=8.1 Hz), 5.60 (m, 1H), 3.71 (br s, 2H), 2.19-2.15 (m, 2H), 1.90-1.88 (m, 2H), 1.45-1.42 (m, 2H), 0.92 (s, 6H).

c) 2-(4,4-Dimethyl-cyclohex-1-enyl)-4-(1-trimethyl-stannanyl-1H-tetrazol-5-ylmethyl)-phenylamine

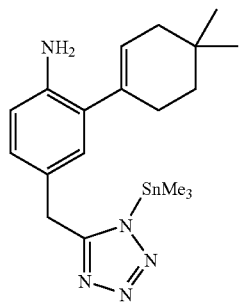

A mixture of [4-amino-3-(4,4-dimethyl-cyclohex-1-enyl)-phenyl]-acetonitrile (as prepared in the previous step, 417 mg, 1.73 mmol) and azidotrimethylstannane (428 mg, 2.08 mmol) in toluene (8 mL) was heated at reflux for 40 h. The reaction was allowed to cool to room temperature and then filtered. The precipitate was washed with 20 mL of toluene and dried under vacuum to afford 410 mg (53%) of the title compound as a white solid. Mass spectrum (ESI, m/z): Calcd. for C$_{16}$H$_{21}$N$_5$, 284.1 (M-SnMe$_3$+2H), found 284.1.

d) 4-Cyano-1-(2-trimethylsilanyl-ethoxymethyl)-1H-imidazole-2-carboxylic acid [2-(4,4-dimethyl-cyclohex-1-enyl)-4-(1H-tetrazol-5-ylmethyl)-phenyl]-amide

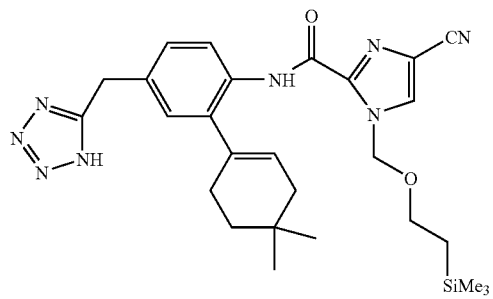

The title compound was prepared from 2-(4,4-dimethyl-cyclohex-1-enyl)-4-(1-trimethylstannanyl-1H-tetrazol-5-yl-methyl)-phenylamine (as prepared in the previous step, 280 mg, 0.626 mmol), potassium 4-cyano-1-(2-trimethylsilanyl-ethoxymethyl)-1H-imidazole-2-carboxylate (as prepared in Example 11, step (d), 267 mg, 1.56 mmol), PyBroP (466 mg, 1.00 mmol) and DIEA (273 μL, 1.56 mmol) according to the procedure in Example 11, step (f) (128 mg, 38%). $^1$H-NMR (CDCl$_3$; 400 MHz): δ9.72 (s, 1H), 8.27 (d, 1H, J=8.3 Hz), 7.76 (s, 1H), 7.19 (m, 1H), 7.12 (s, 1H), 5.94 (s, 2H), 5.70 (s, 1H), 4.29 (s, 2H), 3.66-3.64 (m, 2H), 2.27-2.25 (m, 2H), 2.07-2.06 (m, 2H), 1.56-1.51 (m, 2H), 1.09 (s, 6H), 0.99-0.94 (m, 2H), 0.01 (s, 9H).

e) 5-Cyano-1H-imidazole-2-carboxylic acid [2-(4,4-dimethyl-cyclohex-1-enyl)-4-(1H-tetrazol-5-ylmethyl)-phenyl]-amide The title compound was prepared from 4-cyano-1-(2-trimethylsilanyl-ethoxymethyl)-1H-imidazole-2-carboxylic acid [2-(4,4-dimethyl-cyclohex-1-enyl)-4-(1H-tetrazol-5-ylmethyl)-phenyl]-amide (as prepared in the previous step, 128 mg, 0.240 mmol) according to the procedure in Example 11, step (g) (21 mg, 22%). $^1$H-NMR (CD$_3$OD; 400 MHz): δ8.15 (d, 1H, J=8.1 Hz), 7.97 (s, 1H), 7.17 (d, 1H, J=8.1 Hz), 7.12 (s, 1H), 5.71 (s, 1H), 4.25 (s, 2H), 2.27 (m, 2H), 2.05 (m, 2H), 1.56 (t, 2H, J=6.2 Hz). Mass Spectrum (ESI, m/z): Calcd. for C$_{21}$H$_{22}$N$_8$O, 403.1 (M+H), found 403.0.

EXAMPLE 53

5-Cyano-1H-imidazole-2-carboxylic acid [4-[1-(2-dimethylamino-ethyl)-1H-tetrazol-5-ylmethyl]-2-(4,4-dimethyl-cyclohex-1-enyl)-phenyl]-amide trifluoroacetic acid salt

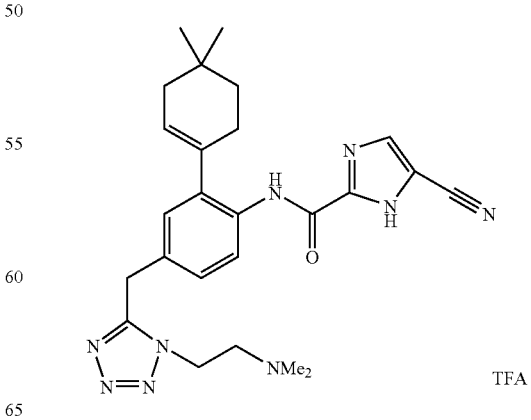

91 a) 5-Cyano-1-(2-trimethylsilanyl-ethoxymethyl)-1H-imidazole-2-carboxylic acid [4-[1-(2-dimethylamino-ethyl)-1H-tetrazol-5-ylmethyl]-2-(4,4-dimethyl-cyclohex-1-enyl)-phenyl]-amide

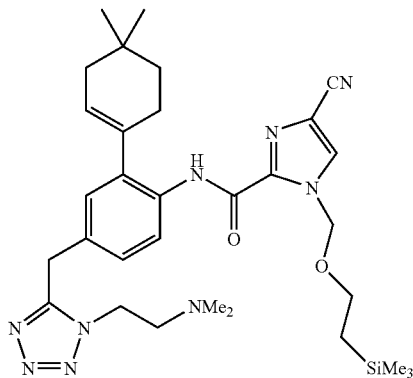

A solution of 4-cyano-1-(2-trimethylsilanyl-ethoxymethyl)-1H-imidazole-2-carboxylic acid [2-(4,4-dimethyl-cyclohex-1-enyl)-4-(1H-tetrazol-5-ylmethyl)-phenyl]-amide (as prepared in Example 52, step (d), 78 mg, 0.14 mmol) and (2-chloro-ethyl)-dimethyl-amine hydrochloride (63 mg, 0.43 mmol) in DMF (1 mL) was treated with DIEA (128 µL, 0.73 mmol) and then heated at 100° C. for 1 h. The reaction was allowed to cool to room temperature, diluted with EtOAc (25 mL) and then washed with water (2×10 mL). The organic phase was dried ($Na_2SO_4$) and concentrated in vacuo. Purification by preparative TLC (10% MeOH—$CHCl_3$) afforded 19 mg (22%) of the title compound. Mass spectrum (ESI, m/z): Calcd. for $C_{31}H_{45}N_9O_2Si$, 604.3 (M+H), found 604.1.

b) 5-Cyano-1H-imidazole-2-carboxylic acid [4-[1-(2-dimethylamino-ethyl)-1H-tetrazol-5-ylmethyl]-2-(4,4-dimethyl-cyclohex-1-enyl)-phenyl]-amide trifluoroacetic acid salt The title compound was prepared from 4-cyano-1-(2-trimethylsilanyl-ethoxymethyl)-1H-imidazole-2-carboxylic acid [4-[1-(2-dimethylamino-ethyl)-1H-tetrazol-5-ylmethyl]-2-(4,4-dimethyl-cyclohex-1-enyl)-phenyl]-amide (as prepared in the previous step, 19 mg, 0.031 mmol) according to the procedure in Example 11, step (g) (18 mg, 99%). $^1$H-NMR ($CD_3OD$; 400 MHz): δ 8.20 (dd, 1H, J=7.5, 1.3 Hz), 7.99 (s, 1H), 7.20-7.19 (m, 2H), 5.74 (m, 1H), 4.79 (t, 2H, J=6.1 Hz), 4.39 (s, 2H), 3.64 (t, 2H, J=6.1 Hz), 2.96 (s, 6H), 2.31-2.27 (m, 2H), 2.05 (m, 2H), 1.57 (t, 2H, J=6.3 Hz), 1.07 (s, 6H). Mass spectrum (ESI, m/z): Calcd. for $C_{25}H_{31}N_9O$, 474.2 (M+H), found 474.0.

92

EXAMPLE 54

5-Cyano-1H-imidazole-2-carboxylic acid [4-[2-(2-dimethylamino-ethyl)-2H-tetrazol-5-ylmethyl]-2-(4,4-dimethyl-cyclohex-1-enyl)-phenyl]-amide trifluoroacetic acid salt

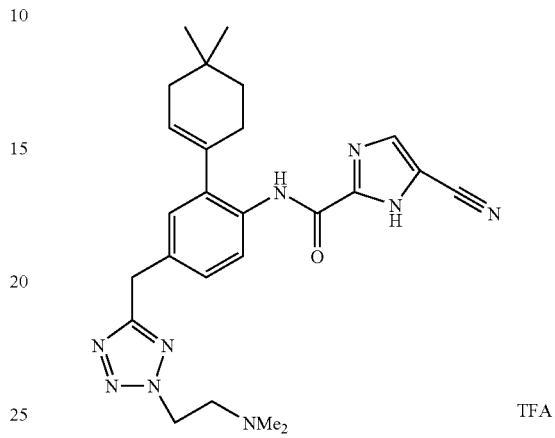

a) 4-Cyano-1-(2-trimethylsilanyl-ethoxymethyl)-1H-imidazole-2-carboxylic acid [4-[2-(2-dimethylamino-ethyl)-2H-tetrazol-5-ylmethyl]-2-(4,4-dimethyl-cyclohex-1-enyl)-phenyl]-amide

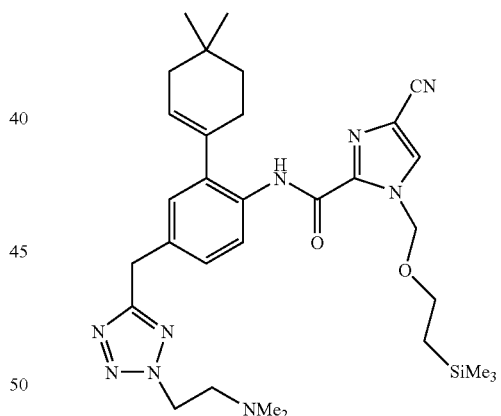

A solution of 4-cyano-1-(2-trimethylsilanyl-ethoxymethyl)-1H-imidazole-2-carboxylic acid [2-(4,4-dimethyl-cyclohex-1-enyl)-4-(1H-tetrazol-5-ylmethyl)-phenyl]-amide (as prepared in Example 42, step (b), 78 mg, 0.14 mmol) and (2-chloro-ethyl)-dimethyl-amine hydrochloride (63 mg, 0.43 mmol) in DMF (1 mL) was treated with DIEA (128 µL, 0.73 mmol) and then heated at 100° C. for 1 h. The reaction was allowed to cool to room temperature, diluted with EtOAc (25 mL) and then washed with water (2×10 mL). The organic phase was dried ($Na_2SO_4$) and concentrated in vacuo. Purification by preparative tlc (10% MeOH—$CHCl_3$) afforded 21 mg (24%) of the title compound. Mass spectrum (ESI, m/z): Calcd. for $C_{31}H_{45}N_9O_2Si$, 604.3 (M+H), found 604.1.

b) 5-Cyano-1H-imidazole-2-carboxylic acid [4-[2-(2-dimethylamino-ethyl)-2H-tetrazol-5-ylmethyl]-2-(4,4-dimethyl-cyclohex-1-enyl)-phenyl]-amide trifluoroacetic acid salt The title compound was prepared from 5-cyano-1-(2-trimethylsilanyl-ethoxymethyl)-1H-imidazole-2-carboxylic acid [4-[1-(2-dimethylamino-ethyl)-2H-tetrazol-5-ylmethyl]-2-(4,4-dimethyl-cyclohex-1-enyl)-phenyl]-amide (as prepared in the previous step, 21 mg, 0.031 mmol) according to the procedure in Example 11, step (g). (18.5 mg, 93%). $^1$H-NMR (CD$_3$OD; 400 MHz): δ 8.16 (1H, J=8.3 Hz), 7.98 (s, 1H), 7.23 (dd, 1H, J=8.3, 2.0 Hz), 7.17 (d, 1H, J=2.0 Hz), 5.71 (m, 1H), 5.13 (t, 2H, J=5.9 Hz), 4.25 (s, 2H), 2.98 (s, 6H), 2.28 (m, 2H), 2.06 (m, 2H), 1.57 (t, 2H, J=6.2 Hz), 1.07 (s, 6H). Mass spectrum (ESI, m/z): Calcd. for C$_{25}$H$_{31}$N$_9$O, 474.2 (M+H), found 474.0.

EXAMPLE 55

5-Cyano-1H-imidazole-2-carboxylic acid [2-cyclohex-1-enyl-4-(1H-tetrazol-5-ylmethyl)-phenyl]-amide

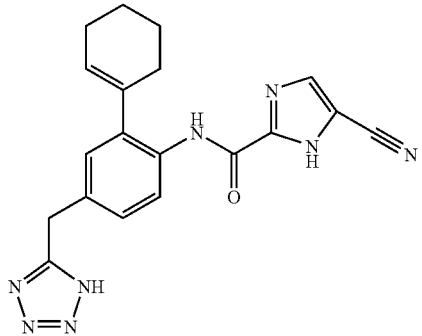

a) (4-Amino-3-cyclohex-1-enyl-phenyl)-acetonitrile

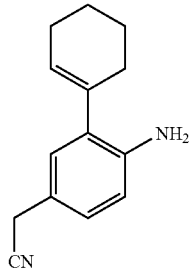

The title compound was prepared from (4-amino-3-bromophenyl)-acetonitrile (as prepared in Example 42, step (a), 668 mg, 3.16 mmol), cyclohexen-yl pinacol boronic ester (790 mg, 3.79 mmol), Pd(PPh$_3$)$_4$ (365 mg, 0.31 mmol), and 2M Na$_2$CO$_3$ (15.2 mL, 12.6 mmol) according to the procedure in Example 44, step (b) (226 mg, 34%). $^1$H-NMR (CDCl$_3$; 400 MHz): δ 6.88 (dd, 1H, J=8.1, 1.9 Hz), 6.84 (d, 1H, J=1.9 Hz), 6.58 (d, 1H, J=8.1 Hz), 5.67 (m, 1H), 3.73 (br s, 2H), 3.53 (s, 2H), 2.14-2.08 (m, 4H), 1.72-1.58 (m, 4H).

b) 2-Cyclohex-1-enyl-4-(1H-tetrazol-5-ylmethyl)-phenylamine

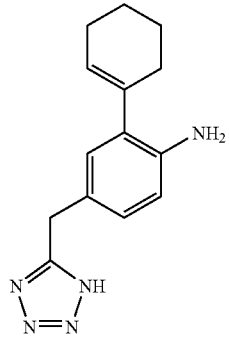

The title compound was prepared from (4-amino-3-cyclohex-1-enyl-phenyl)-acetonitrile (as prepared in the previous step, 103 mg, 0.485 mmol) and azidotrimethylstannane (105 mg, 0.510 mmol) in toluene (4 mL) according to the procedure in Example 52, step (c) and then further purified by preparative TLC (10% MeOH—CHCl$_3$) to afford 40 mg (39%) as a white solid. Mass spectrum (ESI, m/z): Calcd. for C$_{14}$H$_{17}$N$_5$, 256.1 (M+H), found 256.1.

c) 4-Cyano-1-(2-trimethylsilanyl-ethoxymethyl)-1H-imidazole-2-carboxylic acid [2-cyclohex-1-enyl-4-(1H-tetrazol-5-ylmethyl)-phenyl]-amide

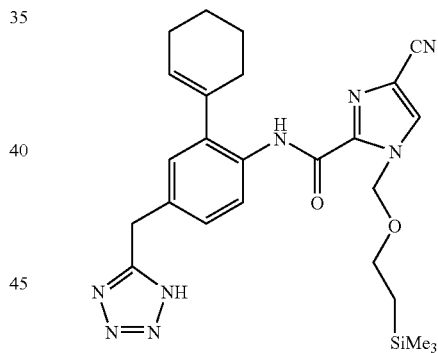

The title compound was prepared from 2-cyclohex-1-enyl-4-(1H-tetrazol-5-ylmethyl)-phenylamine (as prepared in the previous step, 40 mg, 0.15 mmol), potassium 4-cyano-1-(2-trimethylsilanyl-ethoxymethyl)-1H-imidazole-2-carboxylate (as prepared in Example 11, step (d), 67 mg, 0.21 mmol), PyBroP (116 mg, 0.249 mmol) and DIEA (68 μL, 0.39 mmol) according to the procedure in Example 11, step (f) (60 mg, 76%). Mass spectrum (ESI, m/z): Calcd. for C$_{25}$H$_{32}$N$_8$O$_2$Si, 505.2 (M+H), found 504.9.

d) 5-Cyano-1H-imidazole-2-carboxylic acid [2-cyclohex-1-enyl-4-(1H-tetrazol-5-ylmethyl)-phenyl]-amide The title compound was prepared from 4-cyano-1-(2-trimethylsilanyl-ethoxymethyl)-1H-imidazole-2-carboxylic acid [2-cyclohex-1-enyl-4-(1H-tetrazol-5-ylmethyl)-phenyl]-amide (as prepared in the previous step, 56 mg, 0.11 mmol)

according to the procedure in Example 11, step (g) (22 mg, 53%). $^1$H NMR (CD$_3$OD; 400 MHz): δ 8.16 (d, 1H, J=8.3 Hz), 8.00 (s, 1H), 7.19 (dd, 1H, J=8.3, 2.0 Hz), 7.12 (d, 1H, J=2.0 Hz), 5.81 (m, 1H), 4.28 (s, 2H), 2.27-2.23 (m, 4H), 1.93-1.76 (m, 4H). Mass spectrum (ESI, m/z): Calcd. for C$_{19}$H$_{18}$N$_8$O, 375.1 (M+H), found 375.1.

EXAMPLE 56

5-Cyano-1H-imidazole-2-carboxylic acid [2-(4,4-dimethyl-cyclohex-1-enyl)-4-(1H-tetrazol-5-yl)-phenyl]-amide

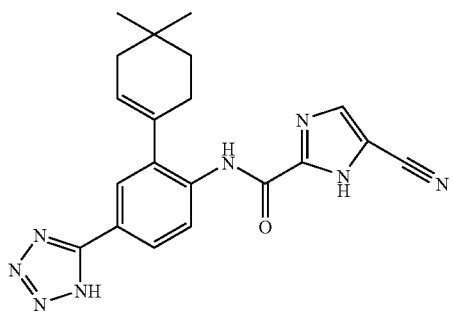

a) 4-Amino-3-bromo-benzonitrile

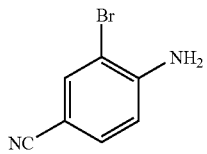

The title compound was prepared from 4-aminobenzonitrile (2.04 g, 17.2 mmol) and NBS (3.07 g, 17.2 mmol) according to the procedure in Example 16, step (b) (2.53 g, 75%). Mass Spectrum (ESI, m/z): Calcd. for C$_7$H$_5$BrN$_2$, 196.9 (M+H), found 196.7.

b) 4-Amino-3-(4,4-dimethyl-cyclohex-1-enyl)-benzonitrile

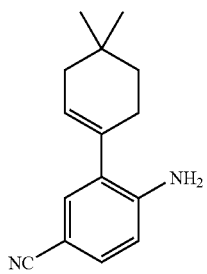

The title compound was prepared from 4-amino-3-bromo-benzonitrile (as prepared in the previous step, 1.0 g, 5.0 mmol), 4,4-dimethylcyclohexen-1-yl boronic acid (938 mg, 6.07 mmol), Pd(PPh$_3$)$_4$ (585 mg, 0.506 mmol) and 2M Na$_2$CO$_3$ (20.2 mL, 40.5 mmol) according to the procedure in Example 44, step (b) (284 mg, 25%). Mass spectrum (ESI, m/z): Calcd. for C$_{15}$H$_{18}$N$_2$, 227.1, found 227.3.

c) 2-(4,4-Dimethyl-cyclohex-1-enyl)-4-(1-trimethyl-stannanyl-1H-tetrazol-5-yl)-phenylamine

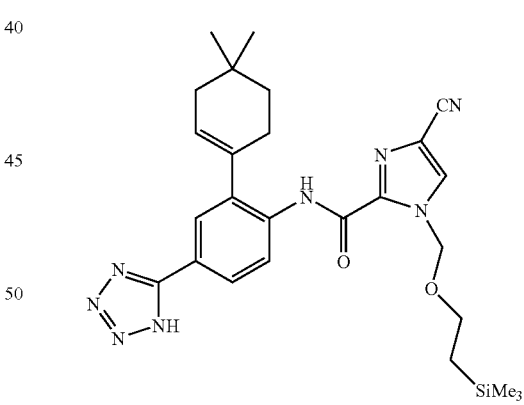

The title compound was prepared from 4-amino-3-(4,4-dimethyl-cyclohex-1-enyl)-benzonitrile (as prepared in the previous step, 245 mg, 1.08 mmol), and azidotrimethylstannane (246 mg, 1.19 mmol) according to the procedure in Example 52, step (c) (363 mg, 78%). Mass spectrum (ESI, m/z): Calcd. for C$_{15}$H$_{19}$N$_5$, 270.1 (M-SnMe$_3$+2H), found 270.1.

d) 4-Cyano-1-(2-trimethylsilanyl-ethoxymethyl)-1H-imidazole-2-carboxylic acid [2-(4,4-dimethyl-cyclohex-1-enyl)-4-(1H-tetrazol-5-yl)-phenyl]-amide The title compound was prepared from 2-(4,4-dimethyl-cyclohex-1-enyl)$_4$-(1-trimethylstannanyl-1H-tetrazol-5-yl)-phenylamine (as prepared in the previous step, 150 mg, 0.347 mmol), potassium 4-cyano-1-(2-trimethylsilanyl-ethoxymethyl)-1H-imidazole-2-carboxylate (as prepared in Example 11, step (d), 148 mg, 0.480 mmol), PyBroP (259 mg, 0.555 mmol) and DIEA (151 μL, 0.867 mmol) according to the procedure in Example 11, step (f) (103 mg, 57%). Mass spectrum (ESI, m/z): Calcd. for C$_{26}$H$_{34}$N$_8$O$_2$Si, 519.2, found 519.1 f) 5-Cyano-1H-imidazole-2-carboxylic acid [2-(4,4-dimethyl-cyclohex-1-enyl)-4-(1H-tetrazol-5-yl)-phenyl]-amide The title compound was prepared from 5-cyano-1-(2-trimethylsilanyl-ethoxymethyl)-1H-imidazole-2-carboxylic acid [2-(4,4-dimethyl-cyclohex-1-enyl)-4-(1H-tetrazol-5-yl)-phenyl]-amide (as prepared in the previous step, 103 mg, 0.198 mmol) according to the procedure in Example 11, step (g) (39.7 mg, 52%). $^1$H-NMR (DMSO-$d_6$; 400 MHz): δ 9.81 (s, 1H), 8.32 (s, 1H), 8.21 (d, 1H, J=8.4 Hz), 7.93 (m, 1H), 7.85 (d, 1H, J=1.1 Hz), 5.78 (m, 1H), 2.32-2.30 (m, 2H), 2.01 (m, 2H), 1.54 (t, 2H, J=6.0 Hz), 1.04 (s, 6H). Mass spectrum (ESI, m/z): Calcd. for $C_{20}H_{20}N_8O$, 389.1 (M+H), found 389.1.

EXAMPLE 57

5-Cyano-1H-imidazole-2-carboxylic acid [2-cyclohex-1-enyl-4-(1H-tetrazol-5-yl)-phenyl]-amide

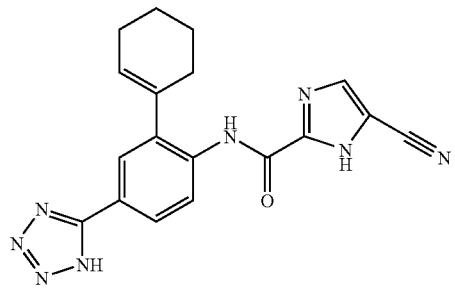

a) 4-Amino-3-cyclohex-1-enyl-benzonitrile

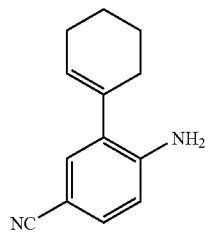

The title compound was prepared from 4-amino-3-bromo-benzonitrile (as prepared in Example 46, step (a), 466 mg, 2.36 mmol), cyclohexen-1-yl boronic acid (354 mg, 2.80 mmol), Pd(PPh$_3$)$_4$ (272 mg, 0.236 mmol), and 2M Na$_2$CO$_3$ (9.4 mL, 18 mmol) according to the procedure in Example 44, step (b) (245 mg, 52%). Mass spectrum (ESI, m/z): Calcd. for $C_{13}H_{14}N_2$, 199.1 (M+H), found 199.2.

b) 2-Cyclohex-1-enyl-4-(1-trimethylstannanyl-1H-tetrazol-5-yl)-phenylamine

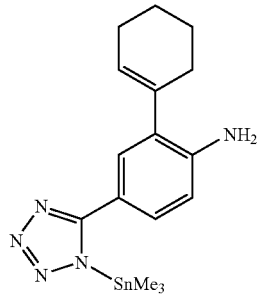

The title compound was prepared from 4-amino-3-cyclohex-1-enyl-benzonitrile (as prepared in the previous step, 245 mg, 0.123 mmol) and azidotrimethylstannane (267 mg, 1.29 mmol) according to the procedure in Example 52, step (c) (320 mg, 64%). Mass spectrum (ESI, m/z): Calcd. for $C_{13}H_{15}N_5$, 242.1 (M-SnMe$_3$+2H), found 242.2 (M+H).

c) 4-Cyano-1-(2-trimethylsilanyl-ethoxymethyl)-1H-imidazole-2-carboxylic acid [2-cyclohex-1-enyl-4-(1H-tetrazol-5-yl)-phenyl]-amide

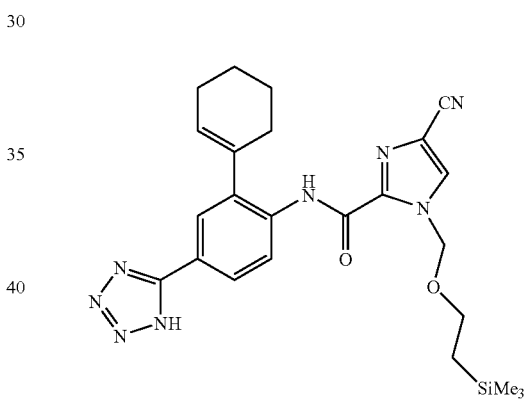

The title compound was prepared from 2-cyclohex-1-enyl-4-(1-trimethylstannanyl-1H-tetrazol-5-yl)-phenylamine (as prepared in the previous step), potassium 4-cyano-1-(2-trimethylsilanyl-ethoxymethyl)-1H-imidazole-2-carboxylate (as prepared in Example 11, step (d)), PyBroP and DIEA according to the procedure in Example 11, step (f). Mass spectrum (ESI, m/z): Calcd. for $C_{24}H_{30}N_8O_2Si$, 491.2, found 491.1.

e) 5-Cyano-1H-imidazole-2-carboxylic acid [2-cyclohex-1-enyl-4-(1H-tetrazol-5-yl)-phenyl]-amide The title compound was prepared from 4-cyano-1-(2-trimethylsilanyl-ethoxymethyl)-1H-imidazole-2-carboxylic acid [2-cyclohex-1-enyl-4-(1H-tetrazol-5-yl)-phenyl]-amide (as prepared in the previous step) according to the procedure in Example 11, step (g). $^1$H-NMR (DMF-$d_7$; 400 MHz): δ 10.07 (s, 1H), 8.55 (s, 1H), 8.46 (d, 1H, J=8.4 Hz), 8.18 (dd, 1H, J=8.4, 2.0 Hz), 8.07 (d, 1H, J=2.0 Hz), 6.09 (m, 1H), 2.47-2.39 (m, 4H), 2.00-1.88 (m, 4H). Mass spectrum (ESI, m/z): Calcd. for $C_{18}H_{16}N_8O$, 361.1, found 361.1.

EXAMPLE 58

5-Cyano-1-(2-dimethylamino-ethyl)-1H-imidazole-2-carboxylic acid {2-cyclohex-1-enyl-4-[1-(2-dimethylamino-ethyl)-1H-tetrazol-5-yl]-phenyl}-amide

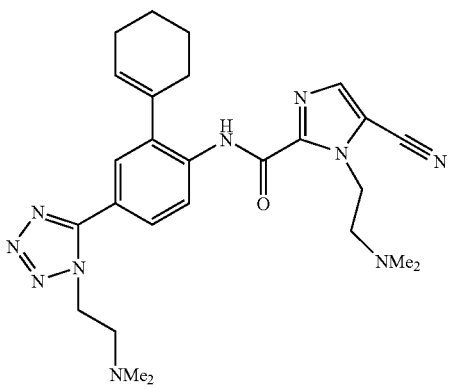

To a solution of 5-cyano-1H-imidazole-2-carboxylic acid [2-cyclohex-1-enyl-4-(1H-tetrazol-5-yl)-phenyl]-amide (as prepared in Example 57, step (e), 37 mg, 0.10 mmol) in DMF (0.5 mL) was added $K_2CO_3$ (42 mg, 0.30 mmol) followed by 2-chloro-ethyl-dimethyl-amine hydrochloride salt (18 mg, 0.12 mmol). The reaction was heated to 70° C. After 3 h, 2-chloro-ethyl-dimethyl-amine (14.6 mg, 0.102 mmol) was again added, followed by $K_2CO_3$ (28 mg, 0.20 mmol) and the resulting mixture heated to 100° C. After 1 h, 2-chloro-ethyl-dimethyl-amine (18 mg, 0.12 mmol) and DIEA (35 µL, 0.20) were added and the resulting mixture stirred at 100° C. overnight. The mixture was poured into EtOAc (20 mL) and washed with saturated aqueous $NaHCO_3$ (2×10 mL). The organic layer was dried ($Na_2SO_4$) and concentrated in vacuo. Purification of the residue by preparative TLC (15% MeOH—$CHCl_3$) afforded 10.7 mg (21%) of the title compound as a white solid. $^1$H-NMR ($CDCl_3$; 400 MHz): δ 9.85 (s, 1H), 8.44 (d, 1H, J=8.5 Hz), 7.98 (dd, 1H, J=8.5, 2.0 Hz), 7.89 (d, 1H, J=1.9 Hz), 7.66 (s, 1H), 5.84 (m, 1H), 4.67 (t, 2H, J=6.7 Hz), 4.60 (t, 2H, J=5.9 Hz), 2.92 (t, 2H, J=6.7 Hz), 2.68 (t, 2H, J=5.9 Hz), 2.25 (s, 6H), 2.22 (s, 6H), 1.81-1.73 (m, 8H). Mass spectrum (ESI, m/z): Calcd. for $C_{26}H_{34}N_{10}O$, 503.2, found 503.2.

EXAMPLE 59

[4-[(4-Cyano-1H-imidazole-2-carbonyl)-amino]-3-(4,4-dimethyl-cyclohex-1-enyl)-benzoyl]-L-glutamic acid

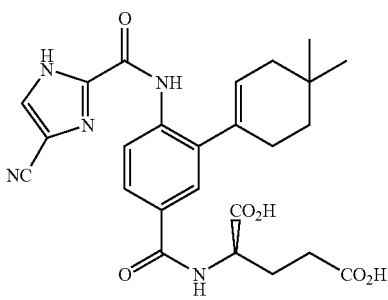

A flask was charged with 4-[(4-cyano-1H-imidazole-2-carbonyl)-amino]-3-(4,4-dimethyl-cyclohex-1-enyl)-benzoic acid (36 mg, 99 µmol)(prepared in Example 65), L-glutamic acid diethyl ester hydrochloride (26 mg, 120 µmol), N-(3-dimethylamino-propyl)-N'-ethylcarbodiimide (23 mg, 120 µmol), 1-hydroxybenzotriazole (13 mg, 99 µmol), DIEA (38 mg, 300 µmol) and 0.3 mL of DCM and stirred for 8 h at RT. The mixture was diluted with 20 mL EtOAc, washed with $NaHCO_3$ (2×20 mL) and brine (20 mL), and the organic layer was dried ($Na_2SO_4$) and concentrated. The residue was dissolved in 2 mL of EtOH and a 7 N aqueous KOH solution (43 µL, 300 µmol) was added and the reaction stirred for 8 h at RT. The pH was adjusted to 2 with a 2 N TFA solution and the title compound was purified by RP-HPLC eluting with a linear gradient of 30% to 50% acetonitrile in 0.1% TFA/$H_2O$ over 10 min on a C18 column giving 25 mg (52%) of a white solid. $^1$H-NMR ($CD_3OD$, 400 MHz): δ 8.35 (d, J=8.6 Hz, 1H), 7.92 (s, 1H), 7.72 (dd, J=8.6, 2.1 Hz, 1H), 7.66 (d, J=2.1 Hz, 1H), 5.74 (m, 1H), 4.54 (m, 1H), 2.39 (t, J=7.4 Hz, 2H), 2.30-2.16 (m, 3H), 2.07-1.95 (m, 3H), 1.54 (t, J=6.3 Hz, 2H), 1.03 (s, 6H). Mass spectrum (ESI, m/z): Calcd. for $C_{25}H_{27}N_5O_6$, 494.2 (M+H), found 494.1.

EXAMPLE 60

3H-Imidazole-2,4-dicarboxylic acid 4-amide 2-[2-(4,4-dimethyl-cyclohex-1-enyl)-phenyl]-amide)×

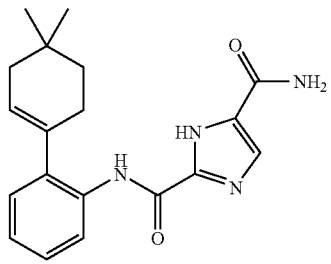

a) 4-Carbamoyl-1-(2-trimethylsilanyl-ethoxymethyl)-1H-imidazole-2-carboxylic acid

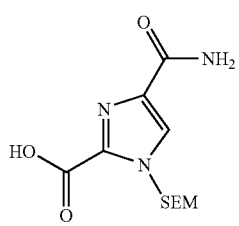

To a solution of 4-cyano-1-(2-trimethylsilanyl-ethoxymethyl)-1H-imidazole-2-carboxylic acid ethyl ester (prepared in Example 11, step (c))(2.0 g, 6.8 mmol) in 15 mL of EtOH was added 5 N NaOH (2.0 mL, 10 mmol) and the reaction stirred for 8 h at RT. The mixture was concentrated, then water (20 mL) and 2 N KOH (3.4 mL, 6.8 mmol) was added and the mixture heated to 90° C. for 1 h. The mixture was cooled in an ice bath and the pH adjusted to 4 with 3 N HCl and a white ppt collected by filtration and dried under vacuum to give 1.5 g (77%) of the title compound. Mass spectrum (ESI, m/z): Calcd. for $C_1, H_{19}N_3O_4Si$, 286.1 (M+H), found 285.8.

b) 2-(4,4-Dimethyl-cyclohex-1-enyl)-phenylamine

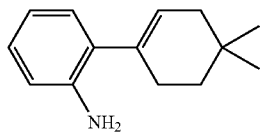

The title compound was prepared by Suzuki coupling of 2-bromoaniline and 4,4-dimethyl-1-cyclohexen-1-yl boronic acid according to the procedure in Example 44, step (b). Mass spectrum (ESI, m/z): Calcd. for $C_{14}H_{19}N$, 202.1 (M+H), found 202.1.

c) 3H-Imidazole-2,4-dicarboxylic acid 4-amide 2-{[2-(4,4-dimethyl-cyclohex-1-enyl)-phenyl]-amide}

The title compound was prepared by coupling 2-(4,4-dimethyl-cyclohex-1-enyl)-phenylamine (prepared in the previous step) and 4-carbamoyl-1-(2-trimethylsilanyl-ethoxymethyl)-1H-imidazole-2-carboxylic acid (as prepared in Example 43, step (a)) according to the procedure in Example 42, step (c), followed by SEM deprotection according to the procedure in Example 61, step (f). $^1$H-NMR (DMSO-$d_6$, 400 MHz): δ 13.83 (s, 1H), 9.61 (s, 1H), 8.23 (dd, J=7.5, 1.5 Hz, 1H), 7.87 (s, 1H), 7.53 (s, 1H), 7.38 (ddd, J=7.5, 7.5, 1.5 Hz, 1H), 7.30 (dd, J=7.5, 1.5 Hz, 1H), 7.22 (ddd, J=7.5, 7.5, 1.5 Hz, 1H), 7.02 (s, 1H), 5.80 (m, 1H), 2.33 (m, 2H), 2.08 (m, 2H), 1.58 (t, J=6.2 Hz, 2H), 1.08 (s, 6H). Mass spectrum (ESI, m/z): Calcd. for $C_{19}H_{22}N_4O_2$, 339.2 (M+H), found 339.2.

EXAMPLE 61

3H-Imidazole-2,4-dicarboxylic acid 2-amide 4-{[2-(4,4-dimethyl-cyclohex-1-enyl)-phenyl]-amide}

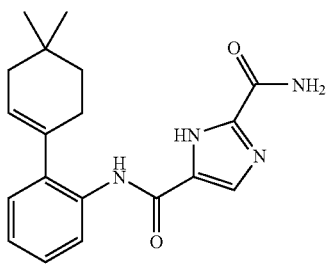

a) 1-(2-Trimethylsilanyl-ethoxymethyl)-1H-imidazole-2-carbaldehyde

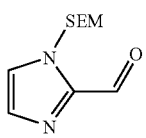

A mixture of 1H-imidazole-2-carbaldehyde (1.1 g, 11 mmol), potassium carbonate (3.0 g, 23 mmol), and SEM-Cl (2.4 mL, 14 mmol) in 10 mL of acetone was heated to 60° C. for 8 h. The mixture was diluted with EtOAc (100 mL) and washed with NaHCO$_3$ (2×100 mL) and brine (100 mL) and the organic layer dried (Na$_2$SO$_4$) and concentrated. The title compound was purified by elution from a 20-g SPE column with 50% EtOAc to give 1.5 g (58%) of a colorless oil. $^1$H-NMR (CDCl$_3$, 400 MHz): δ 9.82 (s, 1H), 7.38 (d, J=1.0 Hz, 1H), 7.34 (d, J=1.0 Hz, 1H), 5.78 (s, 2H), 3.55 (m, 2H), 0.94 (m, 2H), −0.02 (s, 9H).

b) 1-(2-Trimethylsilanyl-ethoxymethyl)-1H-imidazole-2-carbonitrile

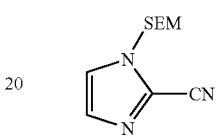

To a solution of 1-(2-trimethylsilanyl-ethoxymethyl)-1H-imidazole-2-carbaldehyde (1.5 g, 6.6 mmol) in 5 mL of MeOH was added hydroxylamine (0.6 mL, 9.1 mmol, 50% aqueous soln) and the reaction stirred for 10 min at RT and then concentrated. The residue was dissolved in 10 mL of DCM and 5 mL of pyridine and cooled in an ice bath. To this mixture was added trifluoroacetic anhydride (4.2 g, 20 mmol) and the reaction stirred for 8 h at RT. The mixture was concentrated and then dissolved in EtOAc (50 mL) and washed with NaHCO$_3$ (2×50 mL) and brine (50 mL). The organic layer was dried (Na$_2$SO$_4$) and concentrated to give 1.2 g (81%) of a brown oil of sufficient purity to use in the next step. $^1$H-NMR (CDCl$_3$, 400 MHz): δ 7.28 (s, 2H), 5.48 (s, 2H), 3.56 (m, 2H), 0.96 (m, 2H), 0.00 (s, 9H). Mass spectrum (APCI, m/z): Calcd. for $C_{10}H_{17}N_3OSi$, 224.1 (M+H), found 223.6.

c) 2-Cyano-3-(2-trimethylsilanyl-ethoxymethyl)-3H-imidazole-4-carboxylic acid ethyl ester

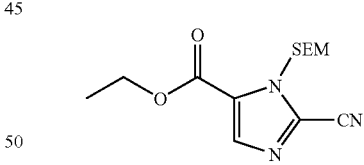

To a solution of 2,2,6,6-tetramethyl-piperidine (0.365 mL, 2.17 mmol) in 4 mL of THF at −50° C. was added n-BuLi (1.08 mL, 2.17 mmol, 2M in pentane) and the mixture allowed to stir for 10 min at 0° C. The mixture was cooled to −50° C. and a solution of 1-(2-trimethylsilanyl-ethoxymethyl)-1H-imidazole-2-carbonitrile (prepared in the previous step) (0.440 g, 1.97 mmol) in 2 mL of THF was added and the reaction stirred for 1 h at −50° C. and then ethyl chloroformate (0.210 mL, 2.17 mmol) was added. After 10 min at −50° C. the reaction was quenched with brine (20 mL) and extracted with EtOAc (2×20 mL) and the organic layer dried (Na$_2$SO$_4$) and concentrated. The title compound was eluted from a 20-g SPE column with 20% EtOAc/hexanes to give 0.280 g (48%) of a colorless oil. $^1$H-NMR (CDCl$_3$, 400 MHz): δ 7.81 (s, 1H), 5.89 (s, 2H), 4.40 (q, J=7.1 Hz, 2H), 3.65 (m, 2H), 1.41 (t, J=7.1 Hz, 3H), 0.96 (m, 2H), 0.00 (s, 9H). Mass spectrum (ESI, m/z): Calcd. for $C_{13}H_{21}N_3O_3Si$, 296.1 (M+H), found 295.5.

d) 2-Carbamoyl-3-(2-trimethylsilanyl-ethoxymethyl)-3H-imidazole-4-carboxylic acid

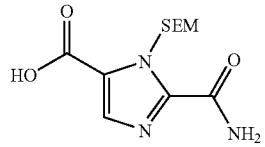

To a solution of 2-cyano-3-(2-trimethylsilanyl-ethoxymethyl)-3H-imidazole-4-carboxylic acid ethyl ester (prepared in the previous step)(0.28 g, 0.95 mmol) in 10 mL of 50% EtOH/H$_2$O was added a 2 N KOH soln (0.95 mL, 1.9 mmol) and the mixture stirred for 8 h at RT. The pH was adjusted to 4 with 3 N HCl and the ppt was collected and dried to give 0.24 g (88%) of a white solid. $^1$H-NMR (DMSO-d$_6$, 400 MHz): δ 13.39 (s, 1H), 8.19 (s, 1H), 7.90 (s, 1H), 7.76 (s, 1H), 6.29 (s, 2H), 3.57 (t, J=7.8 Hz, 2H), 0.87 (t, J=7.8 Hz, 2H), 0.00 (s, 9H). Mass spectrum (ESI, m/z): Calcd. for $C_{11}H_{19}N_3O_4Si$, 286.1 (M+H), found 285.8.

e) 3-(2-Trimethylsilanyl-ethoxymethyl)-3H-imidazole-2,4-dicarboxylic acid 2-amide 4-{[2-(4,4-dimethyl-cyclohex-1-enyl)-phenyl]-amide}

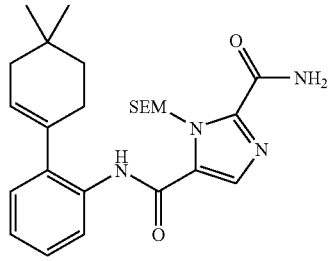

The title compound was prepared by coupling 2-carbamoyl-3-(2-trimethylsilanyl-ethoxymethyl)-3H-imidazole-4-carboxylic acid (prepared in the previous step) and 2-(4,4-dimethyl-cyclohex-1-enyl)-phenylamine (prepared in Example 60, step (b) according to the procedure in Example 42, step (c). Mass spectrum (ESI, m/z): Calcd. for $C_{25}H_{36}N_4O_3Si$, 469.2 (M+H), found 469.0.

f) 3H-Imidazole-2,4-dicarboxylic acid 2-amide 4-{[2-(4,4-dimethyl-cyclohex-1-enyl)-phenyl]-amide}

A solution of 3-(2-trimethylsilanyl-ethoxymethyl)-3H-imidazole-2,4-dicarboxylic acid 2-amide 4-{[2-(4,4-dimethyl-cyclohex-1-enyl)-phenyl]-amide} (90 mg, 0.19 mmol) (prepared in the previous step) in 0.5 mL of EtOH and 0.5 mL of 6 N aq HCl was heated to 80° C. for 3 h. The solution was cooled to RT and the ppt was filtered and washed with H$_2$O and cold MeOH to give 47 mg (72%) of a white solid. $^1$H-NMR (CD$_3$OD, 400 MHz): δ 8.24 (m, 1H), 7.84 (s, 1H), 7.30-7.10 (m, 3H), 5.74 (m, 1H), 2.31 (m, 2H), 2.09 (m, 2H), 1.60 (t, J=6.3 Hz, 2H), 1.10 (s, 6H). Mass spectrum (ESI, m/z): Calcd. for $C_{19}H_{22}N_4O_2$, 339.2 (M+H), found 339.2.

EXAMPLE 62

2-Cyano-3H-imidazole-4-carboxylic acid [2-(4,4-dimethyl-cyclohex-1-enyl)-phenyl]-amide

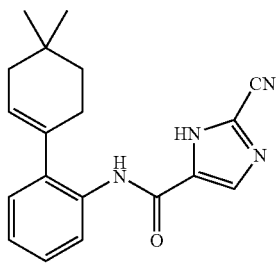

To a suspension of 3-(2-trimethylsilanyl-ethoxymethyl)-3H-imidazole-2,4-dicarboxylic acid 2-amide 4-{[2-(4,4-dimethyl-cyclohex-1-enyl)-phenyl]-amide} (80 mg, 0.17 mmol) (prepared in Example 61, step (e)) in 2 mL of toluene was added 0.4 mL of phosphorus oxychloride and the mixture heated to 80° C. for 30 min. The mixture was concentrated and the residue dissolved in EtOAc (20 mL) and washed with NaHCO$_3$ (2×20 mL) and brine (20 mL), and the organic layer dried (Na$_2$SO$_4$) and concentrated. The title compound was purified by elution from a 5-g SPE column with 2% MeOH/DCM to give 7.0 mg (13%) of a white solid. $^1$H-NMR (CD$_3$OD, 400 MHz): δ 8.24 (dd, J=7.6, 1.6 Hz, 1H), 7.94 (s, 1H), 7.27 (ddd, J=7.6, 7.6, 1.6 Hz, 1H), 7.18 (dd, J=7.6, 1.6 Hz, 1H), 7.12 (ddd, J=7.6, 7.6, 1.6 Hz, 1H), 5.74 (m, 1H), 2.31 (m, 2H), 2.09 (m, 2H), 1.60 (t, J=6.3 Hz, 2H), 1.10 (s, 6H). Mass spectrum (ESI, m/z): Calcd. for $C_{19}H_{20}N_4O_2$, 321.2 (M+H), found 321.2.

EXAMPLE 63

4-Cyano-1H-imidazole-2-carboxylic acid (4,4-dimethyl-3,4,5,6-tetrahydro-2H-[1,2']bipyridinyl-3'-yl)-amide trifluoroacetic acid salt

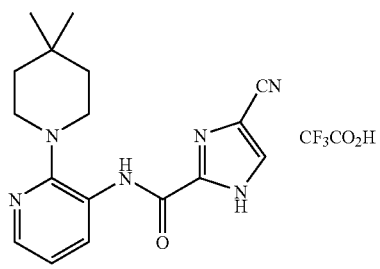

To a solution of 2-chloro-3-nitropyridine (4.74 g, 0.03 mol) in toluene (50 mL), Na$_2$CO$_3$ (3.39 g, 32.0 mmol) and 4,4-dimethylpiperidine (J. Org. Chem., 47(20), 3890, (1982), 3.3 g, 0.033 mmol) were added. The resulting mixture was stirred at 50° C. for 1 h and concentrated in vacuo. Water (20 mL) and EtOAc (50 mL) were then added. The organic layer was separated, dried and concentrated to afford 4,4-dimethyl-3'-nitro-3,4,5,6-tetrahydro-2H-[1,2']bipyridinyl which was directly subjected to catalytic hydrogenation as described in Example 47, step (a) to obtain 4,4-dimethyl-3,4,5,6-tetrahydro-2H-[1,2']bipyridinyl-3'-ylamine (4.1 g, 67%). Mass spectrum (ESI, m/z): Calcd. for $C_{12}H_{19}N_3$, 206.1 (M+H), found 206.2.

4,4-Dimethyl-3,4,5,6-tetrahydro-2H-[1,2']bipyridinyl-3'-ylamine (as prepared in above step) was coupled with 4-cyano-1-(2-trimethylsilanyl-ethoxymethyl)-1H-imidazole-2-carboxylic acid, potassium salt (as prepared in Example 11, step (d), as described in Example 32, step (c) to afford 4-cyano-1-(2-trimethylsilanyl-ethoxymethyl)-1H-imidazole-2-carboxylic acid (4,4-dimethyl-3,4,5,6-tetrahydro-2H-[1,2']bipyridinyl-3'-yl)-amide which was subjected to SEM deprotection as described in Example 47, step (d) to afford the title compound. $^1$H-NMR (DMSO-$d_6$; 400 MHz): δ 14.4 (s, 1H), 9.72 (s, 1H), 8.39 (m, 2H), 8.11 (dd, 1H, J=4.8, 1.7 Hz), 7.13 (dd, 1H, J=4.8, 1.7 Hz), 3.02 (m, 4H), 1.56 (m, 4H), 1.01 (s, 6H); Mass spectrum (ESI, m/z): Calcd. for $C_{17}H_{20}N_6O$, 325.1 (M+H), found 325.2.

EXAMPLE 64

5-Cyano-1H-imidazole-2-carboxylic acid (3-piperidin-1-yl-pyridazin-4-yl)-amide

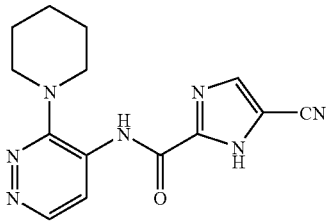

1-(1-Methylsulfanyl-2-nitro-vinyl)-piperidine (WO 2000016766, 202 mg, 1.00 mmol) was reacted with hydrazine (30 μL, 1.0 mmol) in EtOH to afford (2-nitro-1-piperidin-1-yl-vinyl)-hydrazine and which was converted to 4-nitro-3-piperidin-1-yl-pyridazine following procedures analogous to literature methods (Tett. Lett. 41, 3619, (1977)).

4-Nitro-3-piperidin-1-yl-pyridazine (as prepared in above step) was then subjected catalytic hydrogenation (as described in Example 47, step (a)) to afford 3-piperidin-1-yl-pyridazin-4-ylamine. Mass spectrum (ESI, m/z): Calcd. for $C_9H_{14}N_4$, 179.1 (M+H), found 178.9.

3-Piperidin-1-yl-pyridazin-4-ylamine (as prepared in above step) was coupled with 4-cyano-1-(2-trimethylsilanyl-ethoxymethyl)-1H-imidazole-2-carboxylic acid, potassium salt (as prepared in Example 11, step (d)), as described in Example 42, step (c) to afford 5-cyano-1-(2-trimethylsilanyl-ethoxymethyl)-1H-imidazole-2-carboxylic acid (3-piperidin-1-yl-pyridazin-4-yl)-amide which was subjected to SEM deprotection as described in Example 47, step (d) to afford the title compound. $^1$H-NMR (DMSO-$d_6$; 400 MHz): δ 9.79 (br s, 1H), 9.03 (d, 1H, J=4 Hz), 8.50 (s, 1H), 8.43 (d, 1H, J=4 Hz), 3.21 (m, 4H), 1.71-1.86 (m, 6H); Mass spectrum (ESI, m/z): Calcd. for $C_{14}H_{15}N_7O$, 298.1 (M+H), found 298.1.

EXAMPLE 65

4-[(4-Cyano-1H-imidazole-2-carbonyl)-amino]-3-(4,4-dimethyl-cyclohex-1-enyl)-benzoic acid

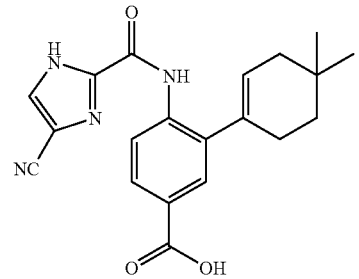

a) 4-[(4-Cyano-1H-imidazole-2-carbonyl)-amino]-3-(4,4-dimethyl-cyclohex-1-enyl)-benzoic acid ethyl ester

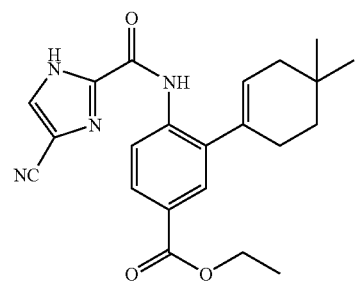

The title compound was prepared according to the procedure for Example 12 using ethyl cyanoformate as the electrophile. Mass spectrum (ESI, m/z): Calcd. for $C_{22}H_{24}N_4O_3$, 393.2 (M+H), found 393.2.

b) 4-[(4-Cyano-1H-imidazole-2-carbonyl)-amino]-3-(4,4-dimethyl-cyclohex-1-enyl)-benzoic acid To a solution of 4-[(4-cyano-1H-imidazole-2-carbonyl)-amino]-3-(4,4-dimethyl-cyclohex-1-enyl)-benzoic acid ethyl ester (50 mg, 0.13 mmol) in 1 mL of EtOH was added a 2 N aqueous solution of KOH (0.20 mL, 0.10 mmol) and the mixture heated to 60° C. for 6 h. The pH was adjusted to 2 with 2 N aq TFA and the title compound was purified by RP-HPLC eluting with a linear gradient of 30% to 50% acetonitrile in 0.1% TFA/$H_2O$ over 10 min on a C18 column giving 40 mg (87%) of a white solid. $^1$H-NMR (CD$_3$OD, 400 MHz): δ 8.48 (d, J=8.6 Hz, 1H), 8.04 (s, 1H), 7.96 (dd, J=8.6, 2.0 Hz, 1H), 7.85 (d, J=2.0 Hz, 1H), 5.85 (m, 1H), 2.40-2.32 (m, 2H), 2.17-2.13 (m, 2H), 1.66 (t, J=6.3 Hz, 2H), 1.15 (s, 6H). Mass spectrum (APCI, m/z): Calcd. for $C_{20}H_{20}N_4O_3$, 363.2 (M-H), found 363.4.

The following examples were produced according to procedures of previous examples as indicated below:

| Example No. | Name | Structure | Procedure Reference | Mass spectrum (ESI, m/z) |
|---|---|---|---|---|
| 66 | 4-Cyano-1H-imidazole-2-carboxylic acid[4-dimethylcarbamoyl-2-(4,4-dimethyl-cyclohex-1-enyl)-phenyl]-amide | 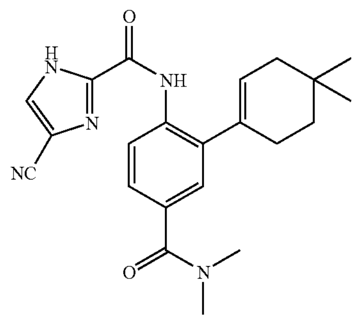 | Example 12 | Calcd. for $C_{22}H_{25}N_5O_2$, 392.2 (M + H), found 392.2 |
| 67 | 4-Cyano-1H-imidazole-2-carboxylic acid[2-(4,4-dimethyl-cyclohex-1-enyl)-phenyl]-amide | 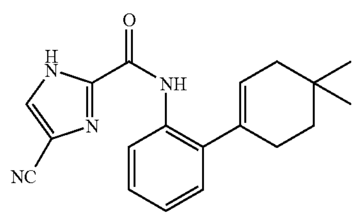 | Example 12 | Calc. for $C_{19}H_{20}N_4O$, 322.1 (M + H), found 322.1 |
| 68 | 5-Cyano-1H-imidazole-2-carboxylic acid[2-(4,4-dimethyl-cyclohex-1-enyl)-4-(1-hydroxy-ethyl)-phenyl]-amide | 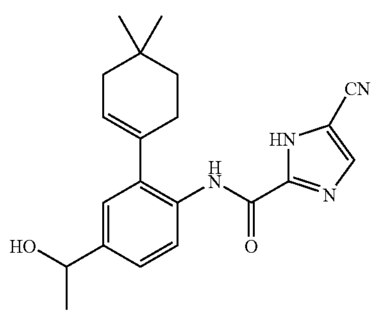 | Example 12 | Calcd. for $C_{21}H_{24}N_4O_2$ 365.2 (M + H), found 365.1 |

IV. Results

An autophosphorylation, fluorescence polarization competition immunoassay was used to determine the potency for c-fms inhibition exhibited by selected compounds of Formulae I and II. The assay was performed in black 96-well microplates (LJL BioSystems). The assay buffer used was 100 mM HEPES, pH 7.5, 1 mM DTT, 0.01% (v/v) Tween-20. Compounds were diluted in assay buffer containing 4% DMSO just prior to the assay. To each well, 5 μL of compound were added followed by the addition of 3 μL of a mix containing 33 nM c-fms (3DP) and 16.7 mM $MgCl_2$ (Sigma) in assay buffer. The kinase reaction was initiated by adding 2 μL of 5 mM ATP (Sigma) in assay buffer. The final concentrations in the assay were 10 nM c-fms, 1 mM ATP, 5 mM $MgCl_2$, 2% DMSO. Control reactions were ran in each plate: in positive and negative control wells, assay buffer (made 4% in DMSO) was substituted for the compound; in addition, positive control wells received 1.2 μL of 50 mM EDTA.

The plates were incubated at room temperature for 45 min. At the end of the incubation, the reaction was quenched with 1.2 μL of 50 mM EDTA (EDTA was not added to the positive control wells at this point; see above). Following a 5-min incubation, each well received 10 μL of a 1:1:3 mixture of anti-phosphotyrosine antibody, 10×, PTK green tracer, 10× (vortexed), FP dilution buffer, respectively (all from PanVera, cat. # P2837). The plate was covered, incubated for 30 min at room temperature and the fluorescence polarization was read on the Analyst. The instrument settings were: 485 nm excitation filter; 530 nm emission filter; Z height: middle of well; G factor: 0.93. Under these conditions, the fluorescence polarization values for positive and negative controls were approximately 300 and 150, respectively, and were used to define the 100% and 0% inhibition of the c-fms reaction. The reported $IC_{50}$ values are averages of three independent measurements.

Table 1 lists representative compounds of Formulae I and II of the invention.

TABLE 1

| COMPOUND | IC$_{50}$ (uM) | % Inhibition (at 10 μM) |
|---|---|---|
| [structure: 2-(4-(2-hydroxyethyl)piperidin-1-yl)phenyl 5-nitrofuran-2-carboxamide] | A | 100 |
| [structure: 5-(hydroxymethyl)-2-(4-methylpiperidin-1-yl)phenyl 5-cyanofuran-2-carboxamide] | A | 100 |
| [structure: 2-(4-methylpiperidin-1-yl)phenyl 5-cyanofuran-2-carboxamide] | A | 97 |
| [structure: 2-(piperidin-1-yl)phenyl 5-cyanofuran-2-carboxamide] | A | 99 |
| [structure: 2-(piperidin-1-yl)phenyl 4-nitro-1H-pyrrole-2-carboxamide] | A | 99 |
| [structure: 5-(hydroxymethyl)-2-(piperidin-1-yl)phenyl 5-nitrofuran-2-carboxamide] | A | 100 |

TABLE 1-continued

| COMPOUND | IC$_{50}$ (uM) | % Inhibition (at 10 μM) |
|---|---|---|
| 2-fluoro-6-piperidinyl-phenyl 5-cyano-furan-2-carboxamide | B | 61 |
| 2-(4-methylpiperidin-1-yl)phenyl 5-nitro-furan-2-carboxamide | A | 92 |
| 2-(4-(hydroxymethyl)piperidin-1-yl)phenyl 5-nitro-furan-2-carboxamide | A | 100 |
| 2-(4-hydroxypiperidin-1-yl)phenyl 5-nitro-furan-2-carboxamide | A | 98 |
| 2-(azepan-1-yl)phenyl 5-nitro-furan-2-carboxamide | A | 100 |
| 2-(piperidin-1-yl)phenyl 5-nitro-furan-2-carboxamide | A | 91 |

TABLE 1-continued
| COMPOUND | IC$_{50}$ (uM) | % Inhibition (at 10 μM) |
|---|---|---|
| 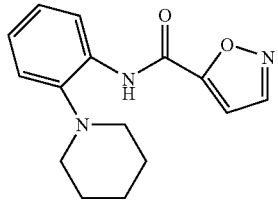 | A | 89 |
| 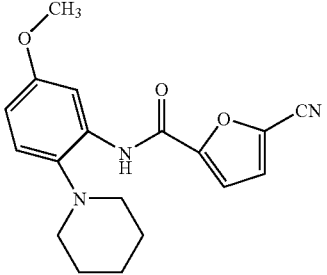 | A | 99* |
| 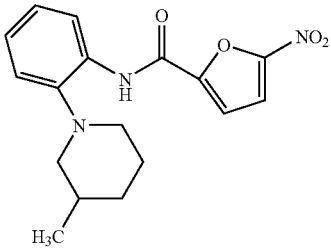 | A | 96 |
| 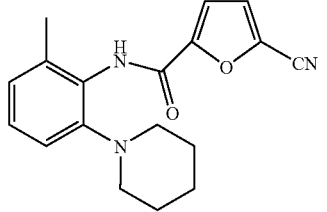 | B | 50 |
| 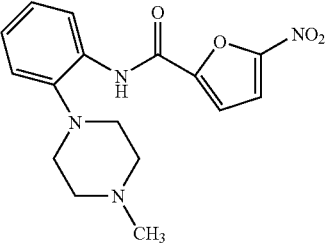 | A | 100 |
| 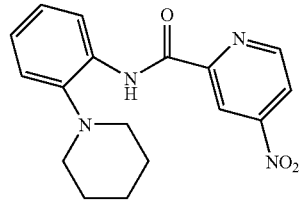 | B | 90 |

TABLE 1-continued

| COMPOUND | IC$_{50}$ (uM) | % Inhibition (at 10 μM) |
|---|---|---|
| (structure: 2-morpholinophenyl-NH-C(O)-furan-5-NO$_2$) | B | 89 |
| (structure: 2-piperidinophenyl-NH-C(O)-furan-5-Cl) | B | 88 |
| (structure: 2-(SCF$_2$CHFCl)phenyl-NH-C(O)-furan-5-NO$_2$) | B | 87 |
| (structure: 2-(2,6-dimethylmorpholino)phenyl-NH-C(O)-furan-5-NO$_2$) | B | 80 |
| (structure: 2-piperidinophenyl-NH-C(O)-phenyl-3-NO$_2$) | B | 77 |
| (structure: 2-piperidinophenyl-NH-C(O)-furan-5-Br) | B | 68 |
| (structure: 2-piperidinophenyl-NH-C(O)-thiophene-5-acetyl) | B | 60 |

TABLE 1-continued

| COMPOUND | IC$_{50}$ (uM) | % Inhibition (at 10 µM) |
|---|---|---|
| [structure: 2-(2,6-dimethylmorpholin-4-yl)phenyl 5-nitrofuran-2-carboxamide] | B | 72 |
| [structure: 2-(piperidin-1-yl)phenyl 4-nitro-1H-pyrazole-3-carboxamide] | B | 61 |
| [structure: 2-ethoxyphenyl 5-nitrofuran-2-carboxamide] | B | 56 |
| [structure: 2-(piperidin-1-yl)phenyl 5-carboxyfuran-2-carboxamide] | B | 24 |
| [structure: 2-(piperidin-1-yl)phenyl 5-formylfuran-2-carboxamide] | B | 86 |
| [structure: 2-(4-hydroxypiperidin-1-yl)phenyl 5-cyanofuran-2-carboxamide] | B | 90* |
| [structure: 2-(4-(2-hydroxyethyl)piperidin-1-yl)phenyl 5-cyanofuran-2-carboxamide] | A | 97* |

TABLE 1-continued
| COMPOUND | IC$_{50}$ (uM) | % Inhibition (at 10 μM) |
|---|---|---|
| 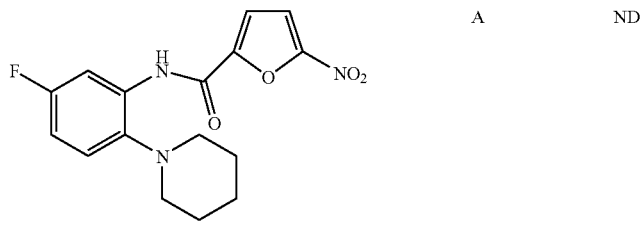 | A | ND |
| 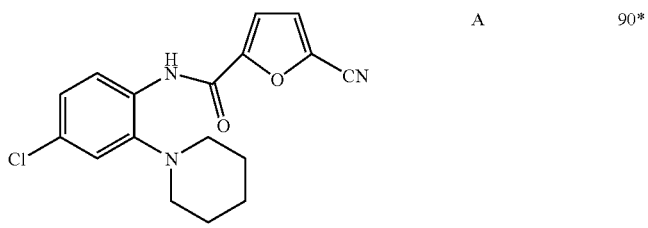 | A | 90* |
| 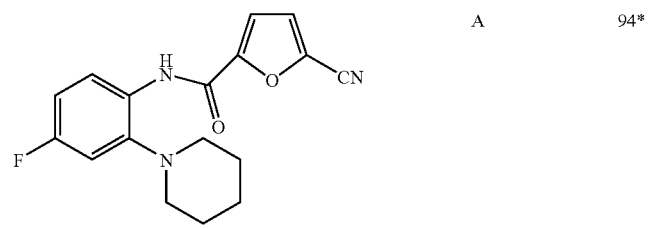 | A | 94* |
| 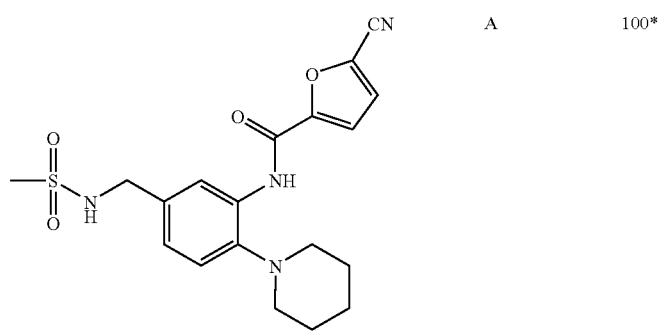 | A | 100* |
| 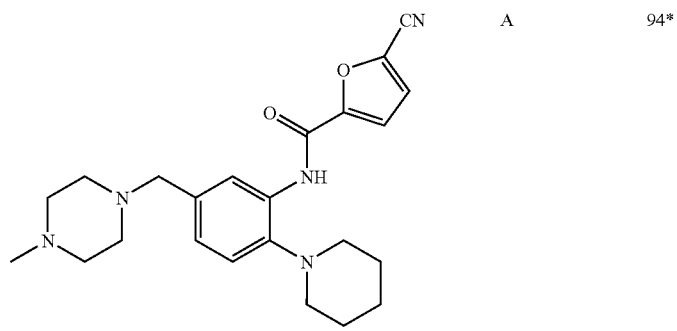 | A | 94* |

TABLE 1-continued

| COMPOUND | IC$_{50}$ (uM) | % Inhibition (at 10 μM) |
|---|---|---|
| (structure: 5-cyanofuran-2-carboxamide linked to phenyl bearing piperidine and CH$_2$NH-CH$_2$-CH(OH)-CH$_2$OH) | A | 93* |
| (structure: 5-cyanofuran-2-carboxamide linked to 5-cyano-2-piperidinylphenyl) | A | 95* |
| (structure: 3-nitro-1H-pyrazole-5-carboxamide linked to 2-piperidinylphenyl) | B | 50* |
| (structure: 5-cyanofuran-2-carboxamide linked to 2-[4-(hydroxymethyl)piperidin-1-yl]phenyl) | A | 93* |

A: <1 μM
B: >1 μM
*% Inhibition @ 2 μM
ND: not determined

In a similar fashion, IC-50's were determined for the compounds of Examples 11-68. Compounds of the preferred Examples 12, 13, 14, 15, 16, 17, 18, 19, 20, 21, 22, 34, 35, 36, 37, 38, 41, 42, 46, 47, 63, and 67 demonstrated activites below 1 μM.

The claimed invention is:

1. A compound of Formula II:

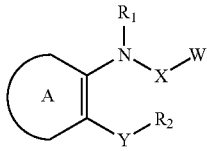

II or a hydrate, tautomer or pharmaceutically acceptable salt thereof, wherein A is phenyl, pyridinyl, pyridazinyl, or piperidinyl; wherein A can be optionally substituted with one or more of —$C_{1-6}$ alkyl, —$C_{2-6}$ alkenyl, amino, aminoalkyl, hydroxyalkyl, alkoxyalkyl, sulfonamidoalkyl, alkylsulfonamidoalkyl, guanidinoalkyl, heteroaryl, alkoxyheteroaryl, aminoheteroaryl, halogen, hydroxy, —$CF_3$, alkoxy, aryl, aminoaryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$; -arylNSO$_2R_a$; or -alkyl SO$_2NR_aR_b$;

$R_1$ is H;

X is —CO—;

Y is a direct link;

$R_2$ is cycloalkyl which is a saturated or partially unsaturated ring composed of from 3 to 8 carbon atoms, methylimidazolyl, piperidinyl, or methylpiperidinyl;

W is imidazolyl, optionally substituted with —$C_{1-6}$ alkyl, amino, aminoalkyl, alkylaminoalkyl, dialkylaminoalkyl, hydroxyalkyl, alkoxyalkyl, heteroaryl, halogen, hydroxy, —$CF_3$, alkoxy, aryl, aralkyl, heteroaralkyl, aryloxy, arylalkoxy, —$OCF_3$, —OCO-alkyl, —OCO-alkylamino, —OCO-alkylamido, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$;

and $R_a$ and $R_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

2. The compound of Formula II according to claim 1, wherein A is phenyl, pyridinyl, pyridazinyl, or piperidinyl; and A can be optionally substituted with one or more of —$C_{1-6}$ alkyl, —$C_{2-6}$ alkenyl, amino, aminoalkyl, hydroxyalkyl, alkoxyalkyl, sulfonamidoalkyl, alkylsulfonamidoalkyl, guanidinoalkyl, heteroaryl, alkoxyheteroaryl, aminoheteroaryl, halogen, hydroxy, —$CF_3$, alkoxy, aryl, aminoaryl, aralkyl, heteroaralkyl, aryloxy, arylalkoxy, —$OCF_3$, —OCO-alkyl, —$COR_a$, —CN, —C(NH)$NH_2$, —$COOR_a$, —$CONR_aR_b$, —$N(R_a)COR_b$, —$NO_2$, —$SO_2R_a$, —$SO_3R_a$ or —$SO_2NR_aR_b$; -arylNSO$_2R_a$; or -alkyl SO$_2NR_aR_b$;

$R_1$ is —H;

X is —CO—;

Y is a direct link;

$R_2$ is cyclohexenyl, dimethylcyclohexenyl, methylimidazolyl, piperidinyl, or methylpiperidinyl;

W is imidazolyl optionally substituted with one or two of the following: —$C_{1-6}$ alkyl, amino, aminoalkyl, alkylaminoalkyl, dialkylaminoalkyl, hydroxyalkyl, alkoxyalkyl, cyano, or —$CONR_aR_b$;

and $R_a$ and $R_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

3. The compound of Formula II according to claim 1, wherein A is phenyl, or pyridinyl; wherein A can be unsubstituted or optionally substituted with bromo, amino, aminoalkyl, hydroxyalkyl, alkoxyalkyl, pyridinyl, N-oxypyrindinyl, methoxy pyrindinyl, —$COR_a$, —$CONR_aR_b$, -arylNSO$_2R_a$; -alkyl SO$_2NR_aR_b$; —$SO_2R_a$, tetrazolyl, alkyltetrazolyl, or alkyltetrazolylalkyl $NR_aR_b$;

$R_1$ is —H;

X is —CO—;

Y is a direct link;

$R_2$ is cyclohexenyl, dimethylcyclohexenyl, methylimidazolyl, piperidinyl, or methylpiperidinyl;

W is imidazolyl optionally substituted with one or two of the following: —$C_{1-6}$ alkyl, amino, aminoalkyl, alkylaminoalkyl, dialkylaminoalkyl, hydroxyalkyl, alkoxyalkyl, cyano, or —$CONR_aR_b$;

and $R_a$ and $R_b$ are independently hydrogen, alkyl, carboxyl, alkylcarboxyl, hydroxyalkyl, cycloalkyl, haloalkyl, aryl, aralkyl, heteroaralkyl, heterocyclyl or heteroaryl.

4. The compound according to claim 1 which is 4-Cyano-1H-imidazole-2-carboxylic acid (4-bromo-2-cyclohex-1-enyl-phenyl)-amide; 4-Cyano-1H-imidazole-2-carboxylic acid [2-cyclohex-1-enyl-4-(1-hydroxy-1-methyl-ethyl)-phenyl]-amide; 4-Cyano-1H-imidazole-2-carboxylic acid [2-cyclohex-1-enyl-4-(1-methoxy-1-methyl-ethyl)-phenyl]-amide; 4-Cyano-1H-imidazole-2-carboxylic acid [4-(1-amino-1-methyl-ethyl)-2-cyclohex-1-enyl-phenyl]-amide, acetic acid salt; 4-Cyano-1H-imidazole-2-carboxylic acid [4-(6-amino-pyridin-3-yl)-2-cyclohex-1-enyl-phenyl]-amide, trifluoroacetic acid salt; 5-Cyano-1H-imidazole-2-carboxylic acid [2-cyclohex-1-enyl-4-(1-oxy-pyridin-4-yl)-phenyl]-amide; 5-Cyano-1H-imidazole-2-carboxylic acid (2-cyclohex-1-enyl-4-pyridin-4-yl-phenyl)-amide; 4-Cyano-1H-imidazole-2-carboxylic acid [2-cyclohex-1-enyl-4-(pyridin-3-yl)-phenyl]-amide; 4-Cyano-1H-imidazole-2-carboxylic acid [2-cyclohex-1-enyl-4-(1-oxy-pyridin-3-yl)-phenyl]-amide; 4-Cyano-1H-imidazole-2-carboxylic acid [2-cyclohex-1-enyl-4-(1-oxy-pyridin-2-yl)-phenyl]-amide; 4-Cyano-1H-imidazole-2-carboxylic acid (2-cyclohex-1-enyl-4-pyridin-2-yl-phenyl)-amide; 4-Cyano-1H-imidazole-2-carboxylic acid (2-cyclohex-1-enyl-4-isopropyl-phenyl)-amide; 4-Cyano-1H-imidazole-2-carboxylic acid (2-piperidin-1-yl-phenyl)-amide, trifluoroacetic acid salt; 4-Cyano-5-(1-hydroxy-1-methyl-ethyl)-1H-imidazole-2-carboxylic acid (4-bromo-2-cyclohex-1-enyl-phenyl)-amide; 4-Cyano-1H-imidazole-2-carboxylic acid (4-acetyl-2-cyclohex-1-enyl-phenyl)-amide; 4-Cyano-1H-imidazole-2-carboxylic acid (4-carbamoyl-2-cyclohex-1-enyl-phenyl)-amide; 4-Cyano-1H-imidazole-2-carboxylic acid [4-carbamoyl-2-(4,4-dimethyl-cyclohex-1-enyl)-phenyl]-amide; 4-Cyano-1H-imidazole-2-carboxylic acid (4'-amino-3-cyclohex-1-enyl-biphenyl-4-yl)-amide, trifluoroacetic acid salt; 4-Cyano-1H-imidazole-2-carboxylic acid (3-cyclohex-1-enyl-4'-methanesulfonylamino-biphenyl-4-yl)-amide; 4-Cyano-1H-imidazole-2-carboxylic acid (3-cyclohex-1-enyl-biphenyl-4-yl)-amide; 4-Cyano-1H-imidazole-2-carboxylic acid [5-acetyl-2-(4,4-dimethyl-cyclohex-1-enyl)-phenyl]-amide; 4-Cyano-1H-imidazole-2-carboxylic acid

[2-(4,4-dimethyl-cyclohex-1-enyl)-5-(1-hydroxy-1-methyl-ethyl)-phenyl]-amide; 4-Cyano-1H-imidazole-2-carboxylic acid [4-bromo-2-(4,4-dimethyl-cyclohex-1-enyl)-phenyl]-amide; 4-Cyano-1H-imidazole-2-carboxylic acid [2-(4,4-dimethyl-cyclohex-1-enyl)-4-(1-hydroxy-1-methyl-ethyl)-phenyl]-amide; 4-Cyano-1H-imidazole-2-carboxylic acid [2-cyclohex-1-enyl-4-(2-hydroxy-2-methyl-propyl)-phenyl]-amide; 4-Cyano-1H-imidazole-2-carboxylic acid [2-(4,4-dimethyl-cyclohex-1-enyl)-4-methanesulfonyl-phenyl]-amide; 5-Cyano-1H-imidazole-2-carboxylic acid [2-cyclohex-1-enyl-4-(2-hydroxy-ethyl)-phenyl]-amide; 5-Cyano-1H-imidazole-2-carboxylic acid [2-(4,4-dimethyl-cyclohex-1-enyl)-4-(2-hydroxy-ethyl)-phenyl]-amide; 5-Cyano-1H-imidazole-2-carboxylic acid (6-cyclohex-1-enyl-benzo[1,3]dioxol-5-yl)-amide; 5-Cyano-1H-imidazole-2-carboxylic acid [2-(3-methyl-3H-imidazol-4-yl)-phenyl]-amide trifluoroacetic acid salt; 4-Cyano-1H-imidazole-2-carboxylic acid [2-(4-methyl-piperidin-1-yl)-phenyl]-amide trifluoroacetic acid salt; 4-Cyano-1H-imidazole-2-carboxylic acid [2-(4,4-dimethyl-cyclohex-1-enyl)-pyridin-3-yl]-amide trifluoroacetic acid salt; 4-Cyano-1H-imidazole-2-carboxylic acid (2-cyclohex-1-enyl-pyridin-3-yl)-amide trifluoroacetic acid salt; 4-Cyano-1H-imidazole-2-carboxylic acid [2-cyclohex-1-enyl-4-(morpholine-4-sulfonyl)-phenyl]-amide; 4-Cyano-1H-imidazole-2-carboxylic acid [(4,4-dimethyl-cyclohex-1-enyl)-4-sulfamoyl-phenyl]-amide; 4-Cyano-1H-imidazole-2-carboxylic acid [2-(4,4-dimethyl-cyclohex-1-enyl)-4-(2-sulfamoyl-ethyl)-phenyl]-amide; 4-Cyano-1H-imidazole-2-carboxylic acid [2-cyclohex-1-enyl-4-(2-sulfamoyl-ethyl)-phenyl]-amide trifluoroacetic acid salt; 5-Cyano-1H-imidazole-2-carboxylic acid (2-cyclohex-1-enyl-4-sulfamoyl-phenyl)-amide trifluoroacetic acid salt; 5-Cyano-1H-imidazole-2-carboxylic acid (3-cyclohex-1-enyl-4'-dimethylsulfamoylbiphenyl-4-yl)-amide; 5-Cyano-1H-imidazole-2-carboxylic acid [2-(4,4-dimethyl-cyclohex-1-enyl)-4-(6-methoxy-pyridin-3-yl)-phenyl]-amide; 5-Cyano-1H-imidazole-2-carboxylic acid [2-(dimethyl-cyclohex-1-enyl)-6-(1-hydroxy-1-methyl-ethyl)-pyridin-3-yl]-amide; 5-Cyano-1H-imidazole-2-carboxylic acid [2-(4,4-dimethyl-cyclohex-1-enyl)-4-(1H-tetrazol-5-ylmethyl)-phenyl]-amide; 5-Cyano-1H-imidazole-2-carboxylic acid [4-[1-(2-dimethylamino-ethyl)-1H-tetrazol-5-ylmethyl]-2-(4,4-dimethyl-cyclohex-1-enyl)-phenyl]-amide trifluoroacetic acid salt; 5-Cyano-1H-imidazole-2-carboxylic acid [4-[2-(2-dimethylamino-ethyl)-2H-tetrazol-5-ylmethyl]-2-(4,4-dimethyl-cyclohex-1-enyl)-phenyl]-amide trifluoroacetic acid salt; 5-Cyano-1H-imidazole-2-carboxylic acid [2-cyclohex-1-enyl-4-(1H-tetrazol-5-ylmethyl)-phenyl]-amide; 5-Cyano-1H-imidazole-2-carboxylic acid [2-(4,4-dimethyl-cyclohex-1-enyl)-4-(1H-tetrazol-5-yl)-phenyl]-amide; 5-Cyano-1H-imidazole-2-carboxylic acid [2-cyclohex-1-enyl-4-(1H-tetrazol-5-yl)-phenyl]-amide; 5-Cyano-1-(2-dimethylamino-ethyl)-1H-imidazole-2-carboxylic acid {2-cyclohex-1-enyl-4-[1-(2-dimethylamino-ethyl)-1H-tetrazol-5-yl]-phenyl}-amide; [4-[(4-Cyano-1H-imidazole-2-carbonyl)-amino]-3-(4,4-dimethyl-cyclohex-1-enyl)-benzoyl]-L-glutamic acid; 3H-Imidazole-2,4-dicarboxylic acid 4-amide 2-{[2-(4,4-dimethyl-cyclohex-1-enyl)-phenyl]-amide}; 3H-Imidazole-2,4-dicarboxylic acid 2-amide 4-{[2-(4,4-dimethyl-cyclohex-1-enyl)-phenyl]-amide}; 2-Cyano-3H-imidazole-4-carboxylic acid [2-(4,4-dimethyl-cyclohex-1-enyl)-phenyl]-amide; 4-Cyano-1H-imidazole-2-carboxylic acid (4,4-dimethyl-3,4,5,6-tetrahydro-2H-[1,2]bipyridinyl-3'-yl)-amide trifluoroacetic acid salt; 5-Cyano-1H-imidazole-2-carboxylic acid (3-piperidin-1-yl-pyridazin-4-yl)-amide; 4-[(4-Cyano-1H-imidazole-2-carbonyl)-amino]-3-(4,4-dimethyl-cyclohex-1-enyl)-benzoic acid; 4-Cyano-1H-imidazole-2-carboxylic acid [4-dimethylcarbamoyl-2-(4,4-dimethyl-cyclohex-1-enyl)-phenyl]-amide; 4-Cyano-1H-imidazole-2-carboxylic acid [2-(4,4-dimethyl-cyclohex-1-enyl)-phenyl]-amide; and 5-Cyano-1H-imidazole-2-carboxylic acid [2-(4,4-dimethyl-cyclohex-1-enyl)-4-(1-hydroxy-ethyl)-phenyl]-amide.

5. The compound according to claim 4 which is
4-Cyano-1H-imidazole-2-carboxylic acid [2-cyclohex-1-enyl-4-(1-hydroxy-1-methyl-ethyl)-phenyl]-amide;
4-Cyano-1H-imidazole-2-carboxylic acid [2-cyclohex-1-enyl-4-(1-methoxy-1-methyl-ethyl)-phenyl]-amide;
4-Cyano-1H-imidazole-2-carboxylic acid [4-(1-amino-1-methyl-ethyl)-2-cyclohex-1-enyl-phenyl]-amide, acetic acid salt;
4-Cyano-1H-imidazole-2-carboxylic acid [4-(6-amino-pyridin-3-yl)-2-cyclohex-1-enyl-phenyl]-amide, trifluoroacetic acid salt;
5-Cyano-1H-imidazole-2-carboxylic acid [2-cyclohex-1-enyl-4-(1-oxy-pyridin-4-yl)-phenyl]-amide;
5-Cyano-1H-imidazole-2-carboxylic acid (2-cyclohex-1-enyl-4-pyridin-4-yl-phenyl)-amide;
4-Cyano-1H-imidazole-2-carboxylic acid [2-cyclohex-1-enyl-4-(1-oxy-pyridin-3-yl)-phenyl]-amide;
4-Cyano-1H-imidazole-2-carboxylic acid [2-cyclohex-1-enyl-4-(pyridin-3-yl)-phenyl]-amide;
4-Cyano-1H-imidazole-2-carboxylic acid [2-cyclohex-1-enyl-4-(1-oxy-pyridin-2-yl)-phenyl]-amide;
4-Cyano-1H-imidazole-2-carboxylic acid (2-cyclohex-1-enyl-4-pyridin-2-yl-phenyl)-amide;
4-Cyano-1H-imidazole-2-carboxylic acid (2-cyclohex-1-enyl-4-isopropyl-phenyl)-amide;
4-Cyano-1H-imidazole-2-carboxylic acid [2-(4,4-dimethyl-cyclohex-1-enyl)-4-(1-hydroxy-1-methyl-ethyl)-phenyl]-amide;
4-Cyano-1H-imidazole-2-carboxylic acid [2-cyclohex-1-enyl-4-(2-hydroxy-2-methyl-propyl)-phenyl]-amide;
4-Cyano-1H-imidazole-2-carboxylic acid [2-(4,4-dimethyl-cyclohex-1-enyl)-4-methanesulfonyl-phenyl]-amide;
5-Cyano-1H-imidazole-2-carboxylic acid [2-cyclohex-1-enyl-4-(2-hydroxy-ethyl)-phenyl]-amide;
5-Cyano-1H-imidazole-2-carboxylic acid [2-(4,4-dimethyl-cyclohex-1-enyl)-4-(2-hydroxy-ethyl)-phenyl]-amide;
4-Cyano-1H-imidazole-2-carboxylic acid [2-(4-methyl-piperidin-1-yl)-phenyl]-amide trifluoroacetic acid salt;
4-Cyano-1H-imidazole-2-carboxylic acid [2-(4,4-dimethyl-cyclohex-1-enyl)-pyridin-3-yl]-amide trifluoroacetic acid salt;
4-Cyano-1H-imidazole-2-carboxylic acid [2-(4,4-dimethyl-cyclohex-1-enyl)-4-(2-sulfamoyl-ethyl)-phenyl]-amide;
4-Cyano-1H-imidazole-2-carboxylic acid [2-cyclohex-1-enyl-4-(2-sulfamoyl-ethyl)-phenyl]-amide trifluoroacetic acid salt;
4-Cyano-1H-imidazole-2-carboxylic acid (4,4-dimethyl-3,4,5,6-tetrahydro-2H-[1,2]bipyridinyl-3'-yl)-amide trifluoroacetic acid salt;
and 4-Cyano-1H-imidazole-2-carboxylic acid [2-(4,4-dimethyl-cyclohex-1-enyl)-phenyl]-amide.

6. The compound according to claim 5 which is
4-Cyano-1H-imidazole-2-carboxylic acid [2-cyclohex-1-enyl-4-(1-hydroxy-1-methyl-ethyl)-phenyl]-amide;
4-Cyano-1H-imidazole-2-carboxylic acid [4-(1-amino-1-methyl-ethyl)-2-cyclohex-1-enyl-phenyl]-amide, acetic acid salt;

4-Cyano-1H-imidazole-2-carboxylic acid [4-(6-amino-pyridin-3-yl)-2-cyclohex-1-enyl-phenyl]-amide, trifluoroacetic acid salt;

5-Cyano-1H-imidazole-2-carboxylic acid (2-cyclohex-1-enyl-4-pyridin-4-yl-phenyl)-amide;

4-Cyano-1H-imidazole-2-carboxylic acid [2-cyclohex-1-enyl-4-(1-oxy-pyridin-3-yl)-phenyl]-amide;

4-Cyano-1H-imidazole-2-carboxylic acid (2-cyclohex-1-enyl-4-pyridin-2-yl-phenyl)-amide;

4-Cyano-1H-imidazole-2-carboxylic acid (2-cyclohex-1-enyl-4-isopropyl-phenyl)-amide;

4-Cyano-1H-imidazole-2-carboxylic acid [2-(4,4-dimethyl-cyclohex-1-enyl)-4-(1-hydroxy-1-methyl-ethyl)-phenyl]-amide;

4-Cyano-1H-imidazole-2-carboxylic acid [2-cyclohex-1-enyl-4-(2-hydroxy-2-methyl-propyl)-phenyl]-amide; and 5-Cyano-1H-imidazole-2-carboxylic acid [2-(4,4-dimethyl-cyclohex-1-enyl)-4-(2-hydroxy-ethyl)-phenyl]-amide.

7. A pharmaceutical composition, comprising a compound of claim 1 and a pharmaceutically acceptable carrier.

8. A pharmaceutical dosage form comprising a pharmaceutically acceptable carrier and from about 0.5 mg to about 10 g of at least one compound of claim 1.

9. A dosage form according to claim 8 adapted for parenteral or oral administration.

* * * * *